(12) United States Patent
Freimoser-Grundschober et al.

(10) Patent No.: US 12,215,155 B2
(45) Date of Patent: Feb. 4, 2025

(54) ANTIBODIES BINDING TO CD3 AND CD19

(71) Applicant: Hoffmann-La Roche Inc., Little Falls, NJ (US)

(72) Inventors: Anne Freimoser-Grundschober, Schlieren (CH); Maria Valeria Gonzalez Nicolini, Schlieren (CH); Ralf Hosse, Schlieren (CH); Alexander Knaupp, Penzberg (DE); Ekkehard Moessner, Schlieren (CH); Wolfgang Richter, Basel (CH); Halina Trochanowska, Schlieren (CH); Pablo Umaña, Schlieren (CH); Christian Klein, Schlieren (CH); Inja Waldhauer, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/446,032

(22) Filed: Aug. 8, 2023

(65) Prior Publication Data
US 2024/0132590 A1 Apr. 25, 2024

Related U.S. Application Data

(62) Division of application No. 17/350,111, filed on Jun. 17, 2021, now Pat. No. 11,780,920.

(30) Foreign Application Priority Data

Jun. 19, 2020 (EP) .................................. 20181056

(51) Int. Cl.
| | | |
|---|---|---|
| C07K 16/28 | (2006.01) | |
| A61K 39/00 | (2006.01) | |
| A61P 35/00 | (2006.01) | |
| C07K 16/30 | (2006.01) | |

(52) U.S. Cl.
CPC .......... *C07K 16/2809* (2013.01); *A61P 35/00* (2018.01); *C07K 16/30* (2013.01); *A61K 2039/505* (2013.01); *C07K 2317/52* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,571,894 A | 11/1996 | Wels et al. | |
| 5,587,458 A | 12/1996 | King | |
| 5,591,828 A | 1/1997 | Bosslet et al. | |
| 5,731,168 A | 3/1998 | Carter et al. | |
| 5,821,337 A | 10/1998 | Carter et al. | |
| 5,869,046 A | 2/1999 | Presta et al. | |
| 6,248,516 B1 | 6/2001 | Winter et al. | |
| 6,737,056 B1 | 5/2004 | Presta | |
| 6,809,185 B1 | 10/2004 | Schoonjans et al. | |
| 7,332,581 B2 | 2/2008 | Presta | |
| 7,695,936 B2 | 4/2010 | Carter et al. | |
| 8,227,577 B2 | 7/2012 | Klein et al. | |
| 8,242,247 B2 | 8/2012 | Klein et al. | |
| 8,703,132 B2 | 4/2014 | Imhof-Jung et al. | |
| 8,709,421 B2 | 4/2014 | Heiss et al. | |
| 8,796,424 B2 | 8/2014 | Croasdale et al. | |
| 8,969,526 B2 | 3/2015 | Baehner et al. | |
| 9,068,008 B2 | 6/2015 | Mossner et al. | |
| 9,266,938 B2 | 2/2016 | Ast et al. | |
| 9,266,967 B2 | 2/2016 | Klein et al. | |
| 9,382,323 B2 | 7/2016 | Brinkmann et al. | |
| 9,447,159 B2 | 9/2016 | Ast et al. | |
| 9,526,797 B2 | 12/2016 | Gerdes et al. | |
| 10,392,445 B2 | 8/2019 | Amann et al. | |
| 10,464,981 B2 | 11/2019 | Amann et al. | |
| 11,267,903 B2 | 3/2022 | Amann et al. | |
| 11,286,300 B2 | 3/2022 | Ferrara Koller et al. | |
| 2007/0111281 A1 | 5/2007 | Sondermann et al. | |
| 2008/0241152 A1 | 10/2008 | Alitalo et al. | |
| 2009/0252683 A1 | 10/2009 | Kischel et al. | |
| 2010/0015133 A1 | 1/2010 | Igawa et al. | |
| 2010/0150918 A1 | 6/2010 | Kufer et al. | |
| 2010/0316645 A1 | 12/2010 | Imhof-Jung et al. | |
| 2011/0293613 A1 | 12/2011 | Brinkmann et al. | |
| 2012/0225071 A1 | 9/2012 | Klein et al. | |
| 2012/0276125 A1 | 11/2012 | Ast et al. | |

(Continued)

FOREIGN PATENT DOCUMENTS

| | | |
|---|---|---|
| CA | 2896370 A1 | 9/2014 |
| CN | 103748114 A | 4/2014 |

(Continued)

OTHER PUBLICATIONS

U.S. Appl. No. 18/244,135, Hoffmann-La Roche Inc.
Almagro et al., "Humanization of antibodies," Front Biosci. 13:1619-33 (2008).
Atwell et al., "Stable Heterodimers from Remodeling the Domain Interface of a Homodimer using a Phage Display Library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. April 17-21, Washington, DC. 70(8 Suppl) Abstract 5621 (2010) (1 page).

(Continued)

*Primary Examiner* — Laura B Goddard
*Assistant Examiner* — Sarah A Alsomairy
(74) *Attorney, Agent, or Firm* — Clark & Elbing LLP; Karen L. Elbing

(57) ABSTRACT

The present invention generally relates to antibodies that bind to CD3 and CD19, e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

64 Claims, 19 Drawing Sheets

Specification includes a Sequence Listing.

(56) References Cited

U.S. PATENT DOCUMENTS

| | | |
|---|---|---|
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0200833 A1 | 7/2016 | Amann et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0340399 A1 | 11/2016 | Amann et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |
| 2018/0230215 A1 | 8/2018 | Hofer et al. |
| 2018/0282409 A1 | 10/2018 | Ferrara Koller et al. |
| 2019/0194291 A1 | 6/2019 | Bruenker et al. |
| 2019/0382507 A1 | 12/2019 | Amann et al. |
| 2020/0190206 A1 | 6/2020 | Ferrara Koller et al. |
| 2020/0199234 A1 | 6/2020 | Georges et al. |
| 2020/0247904 A1 | 8/2020 | Amann et al. |
| 2020/0270347 A1 | 8/2020 | Freimoser-Grundschober et al. |
| 2020/0317774 A1 | 10/2020 | Hofer et al. |
| 2020/0325238 A1 | 10/2020 | Bacac et al. |
| 2020/0347115 A1 | 11/2020 | Duerr et al. |
| 2021/0009656 A1 | 1/2021 | Bruenker et al. |
| 2021/0070882 A1 | 3/2021 | Bacac et al. |
| 2021/0163617 A1 | 6/2021 | Ferrara Koller et al. |
| 2021/0253724 A1 | 8/2021 | Claus et al. |
| 2021/0403562 A1 | 12/2021 | Freimoser-Grundschober et al. |
| 2022/0213199 A1 | 7/2022 | Bujotzek et al. |
| 2022/0259318 A1 | 8/2022 | Bujotzek et al. |
| 2023/0159642 A1 | 5/2023 | Bujotzek et al. |
| 2023/0277662 A1 | 9/2023 | Freimoser-Grundschober et al. |
| 2023/0416365 A1 | 12/2023 | Georges et al. |
| 2023/0416411 A1 | 12/2023 | Bruenker et al. |
| 2024/0042022 A1 | 2/2024 | Freimoser-Grundschober et al. |
| 2024/0043535 A1 | 2/2024 | Amann et al. |

FOREIGN PATENT DOCUMENTS

| | | |
|---|---|---|
| EP | 0404097 B1 | 9/1996 |
| EP | 1870459 A1 | 12/2007 |
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2008-543339 A | 12/2008 |
| JP | 2012-518404 A | 8/2012 |
| JP | 2018-529733 A | 10/2018 |
| RU | 2651776 C2 | 4/2018 |
| TW | 201726719 A | 8/2017 |
| WO | WO-91/03493 A1 | 3/1991 |
| WO | WO-1993/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2004/106381 A1 | 12/2004 |
| WO | WO-2005/012493 A2 | 2/2005 |
| WO | WO-2005044859 A2 | 5/2005 |
| WO | WO-2006/082515 A2 | 8/2006 |
| WO | WO-2006/121168 A1 | 11/2006 |
| WO | WO-2007/002223 A2 | 1/2007 |
| WO | WO-2007/024715 A2 | 3/2007 |
| WO | WO-2007/042261 A2 | 4/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2008/031056 A2 | 3/2008 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/095031 A2 | 8/2010 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | WO-2012/130831 A1 | 10/2012 |
| WO | WO-2012/158818 A2 | 11/2012 |
| WO | WO-2012/162067 A2 | 11/2012 |
| WO | WO-2013/019906 A1 | 2/2013 |
| WO | WO-2013/026831 A1 | 2/2013 |
| WO | WO-2013/026833 A1 | 2/2013 |
| WO | WO-2013/026837 A1 | 2/2013 |
| WO | WO-2013/096291 A2 | 6/2013 |
| WO | WO-2013/157953 A1 | 10/2013 |
| WO | WO-2013/157954 A1 | 10/2013 |
| WO | WO-2014/012085 A2 | 1/2014 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/081955 A1 | 5/2014 |
| WO | WO-2014/122251 A2 | 8/2014 |
| WO | WO-2014/131694 A1 | 9/2014 |
| WO | WO-2014/131711 A1 | 9/2014 |
| WO | WO-2014/131712 A1 | 9/2014 |

(56) References Cited

FOREIGN PATENT DOCUMENTS

| WO | WO-2014/141152 A2 | 9/2014 | |
|----|----|----|----|
| WO | WO-2014/151910 A1 | 9/2014 | |
| WO | WO-2014/153002 A1 | 9/2014 | |
| WO | WO-2014/122251 A3 | 10/2014 | |
| WO | WO-2014/141152 A3 | 12/2014 | |
| WO | WO-2014/191113 A1 | 12/2014 | |
| WO | WO-2015/006749 A2 | 1/2015 | |
| WO | WO-2014/191113 A8 | 2/2015 | |
| WO | WO-2015/006749 A3 | 3/2015 | |
| WO | WO-2015/048272 A1 | 4/2015 | |
| WO | WO-2015/101588 A1 | 7/2015 | |
| WO | WO-2015/150447 A1 | 10/2015 | |
| WO | WO-2016/020065 A1 | 2/2016 | |
| WO | WO-2016/036678 A1 | 3/2016 | |
| WO | WO-2016/075278 A1 | 5/2016 | |
| WO | WO-2016/079076 A1 | 5/2016 | |
| WO | WO-2016/079081 A1 | 5/2016 | |
| WO | WO-2016/156291 A1 | 10/2016 | |
| WO | WO-2016/179003 A1 | 11/2016 | |
| WO | WO-2017/055541 A1 | 4/2017 | |
| WO | WO-2017055314 A1 * | 4/2017 | ............. A61P 35/00 |
| WO | WO-2017/194438 A1 | 11/2017 | |
| WO | WO-2018/114748 A1 | 6/2018 | |
| WO | WO-2018/127473 A1 | 7/2018 | |
| WO | WO-2019/086499 A1 | 5/2019 | |
| WO | WO-2019/175071 A1 | 9/2019 | |
| WO | WO-2020/007817 A1 | 1/2020 | |
| WO | WO-2020/127618 A1 | 6/2020 | |
| WO | WO-2020/127619 A1 | 6/2020 | |
| WO | WO-2021/046536 A1 | 3/2021 | |
| WO | WO-2021/255138 A1 | 12/2021 | |
| WO | WO-2021/255143 A1 | 12/2021 | |
| WO | WO-2021/255146 A1 | 12/2021 | |

OTHER PUBLICATIONS

Carter, "Bispecific human IgG by design," J Immunol Methods. 248(1-2):7-15 (2001).

Chan et al., "Variable region domain exchange in human IgGs promotes antibody complex formation with accompanying structural changes and altered effector functions," Mol Immunol. 41(5):527-38 (2004).

Chelius et al., "Identification and Characterization of Deamidation Sites in the Conserved Regions of Human Immunoglobulin Gamma Antibodies," Anal Chem. 77(18):6004-11 (2005).

Claus et al., "Tumor-targeted 4-1BB agonists for combination with T cell bispecific antibodies as off-the-shelf therapy," available in PMC Apr. 24, 2020, published in final edited form as: Sci Transl Med. 11(496):eaav5989 (2019) (25 pages).

Cui et al., "Chemically programmed bispecific antibodies that recruit and activate T cells," J Biol Chem. 287(34):28206-14 (2012) (10 pages).

Edelman et al., "The covalent structure of an entire gammaG immunoglobulin molecule," Proc Natl Acad Sci U S A. 63(1):78-85 (1969).

Hoffman et al., "Blinatumomab, a bi-specific anti-CD19/CD3 BITER antibody for the treatment of acute lymphoblastic leukemia: perspectives and current pediatric applications," Front Oncol. 4(63):1-5 (2014).

Holliger et al., "Diabodies': small bivalent and bispecific antibody fragments," Proc Natl Acad Sci U S A. 90(14):6444-8 (1993).

Holliger et al., "Specific killing of lymphoma cells by cytotoxic T-cells mediated by a bispecific diabody," Protein Eng. 9(3):299-305 (1996).

Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).

Hudson et al., "Engineered antibodies," Nat Med. 9(1):129-34 (2003).

Husain et al., "Expanding the Boundaries of Biotherapeutics with Bispecific Antibodies," BioDrugs. 32(5):441-464 (2018).

Kipriyanov et al., "Bispecific CD3 x CD19 diabody for T cell-mediated lysis of malignant human B cells," Int J Cancer. 77(5):763-72 (1998).

Kipriyanov et al., "Bispecific Tandem Diabody for Tumor Therapy with Improved Antigen Binding and Pharmacokinetics," J Mol Biol. 293(1):41-56 (1999).

Klein et al., "Progress in overcoming the chain association issue in bispecific heterodimeric IgG antibodies," MAbs. 4(6):653-63 (2012).

Kontermann, "Dual targeting strategies with bispecific antibodies," MAbs. 4(2):182-97 (2012).

Li et al., "Preparation of a Humanized Anti-CD3 Antibody Containing Mutated Constant Region and Its Biological Activity," Chinese Journal of Biochemistry and Molecular Biology. 20(1):28-33 (2004).

Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).

Merchant et al., "An efficient route to human bispecific IgG," Nat Biotechnol. 16(7):677-81 (1998).

Miller et al., "Design, construction, and in vitro analyses of multivalent antibodies," J Immunol. 170(9):4854-61 (2003).

Moore et al., "A novel bispecific antibody format enables simultaneous bivalent and monovalent co-engagement of distinct target antigens," MAbs. 3(6):546-57 (2011).

Moore et al., "Application of dual affinity retargeting molecules to achieve optimal redirected T-cell killing of B-cell lymphoma," Blood. 117(17):4542-51 (2011) (11 pages).

Nagorsen et al., "Immunomodulatory therapy of cancer with T cell-engaging BiTE antibody blinatumomab," Exp Cell Res. 317(9):1255-60 (2011).

Oshimi et al., "Increased lysis of patient CD10-positive leukemic cells by T cells coated with anti-CD3 Fab' antibody cross-linked to anti-CD10 Fab' antibody," Blood. 77(5):1044-9 (1991) (7 pages).

Pessano et al., "The T3/T cell receptor complex: antigenic distinction between the two 20-kd T3 (T3-delta and T3-epsilon) subunits," EMBO J. 4(2):337-44 (1985).

Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).

Ridgway et al., "'Knobs-into-holes' engineering of antibody CH3 domains for heavy chain heterodimerization," Protein Eng. 9(7):617-21 (1996).

Riedle et al., "In vivo activation and expansion of T cells by a bi-specific antibody abolishes metastasis formation of human melanoma cells in SCID mice," Int J Cancer. 75(6):908-18 (1998).

Sakuishi et al., "Targeting Tim-3 and PD-1 pathways to reverse T cell exhaustion and restore anti-tumor immunity," J Exp Med. 207(10):2187-94 (2010).

Schaefer et al., "Immunoglobulin domain crossover as a generic approach for the production of bispecific IgG antibodies," Proc Natl Acad Sci U S A. 108(27):11187-92 (2011).

Seimetz et al., "Development and approval of the trifunctional antibody catumaxomab (anti-EpCAM x anti-CD3) as a targeted cancer immunotherapy," Cancer Treat Rev. 36(6):458-67 (2010).

Stubenrauch et al., "Impact of molecular processing in the hinge region of therapeutic IgG4 antibodies on disposition profiles in cynomolgus monkeys," Drug Metab Dispos. 38(1):84-91 (2010).

Sun et al., "Anti-CD20/CD3 T cell-dependent bispecific antibody for the treatment of B cell malignancies," Sci Transl Med. 7(287):287ra70 (2015) (11 pages).

Torisu-Itakura et al., "Redirected lysis of human melanoma cells by a MCSP/CD3-bispecific BiTE antibody that engages patient-derived T cells," J Immunother. 34(8):597-605 (2011).

Tutt et al., "Trispecific F(ab')3 derivatives that use cooperative signaling via the TCR/CD3 complex and CD2 to activate and redirect resting cytotoxic T cells," J Immunol. 147(1):60-9 (1991).

Weidle et al., "The intriguing options of multispecific antibody formats for treatment of cancer," Cancer Genomics Proteomics. 10(1):1-18 (2013).

(56) References Cited

OTHER PUBLICATIONS

Wolf et al., "BiTEs: bispecific antibody constructs with unique anti-tumor activity," Drug Discov Today. 10(18):1237-44 (2005).
Yokosuka et al., "Programmed cell death 1 forms negative costimulatory microclusters that directly inhibit T cell receptor signaling by recruiting phosphatase SHP2," J Exp Med. 209(6):1201-17 (2012).
Zhu et al., "Identification of heavy chain residues in a humanized anti-CD3 antibody important for efficient antigen binding and T cell activation," J Immunol. 155(4):1903-10 (1995).
English Translation of Search Report for Taiwanese Patent Application No. 110122112, dated Jun. 30, 2022 (2 pages).
International Search Report and Written Opinion for International Application No. PCT/EP2021/066346, mailed Sep. 7, 2021 (20 pages).
Office Action with Search Report for Taiwanese Patent Application No. 110122112, dated Jul. 4, 2022 (8 pages) (partial translation included).

\* cited by examiner

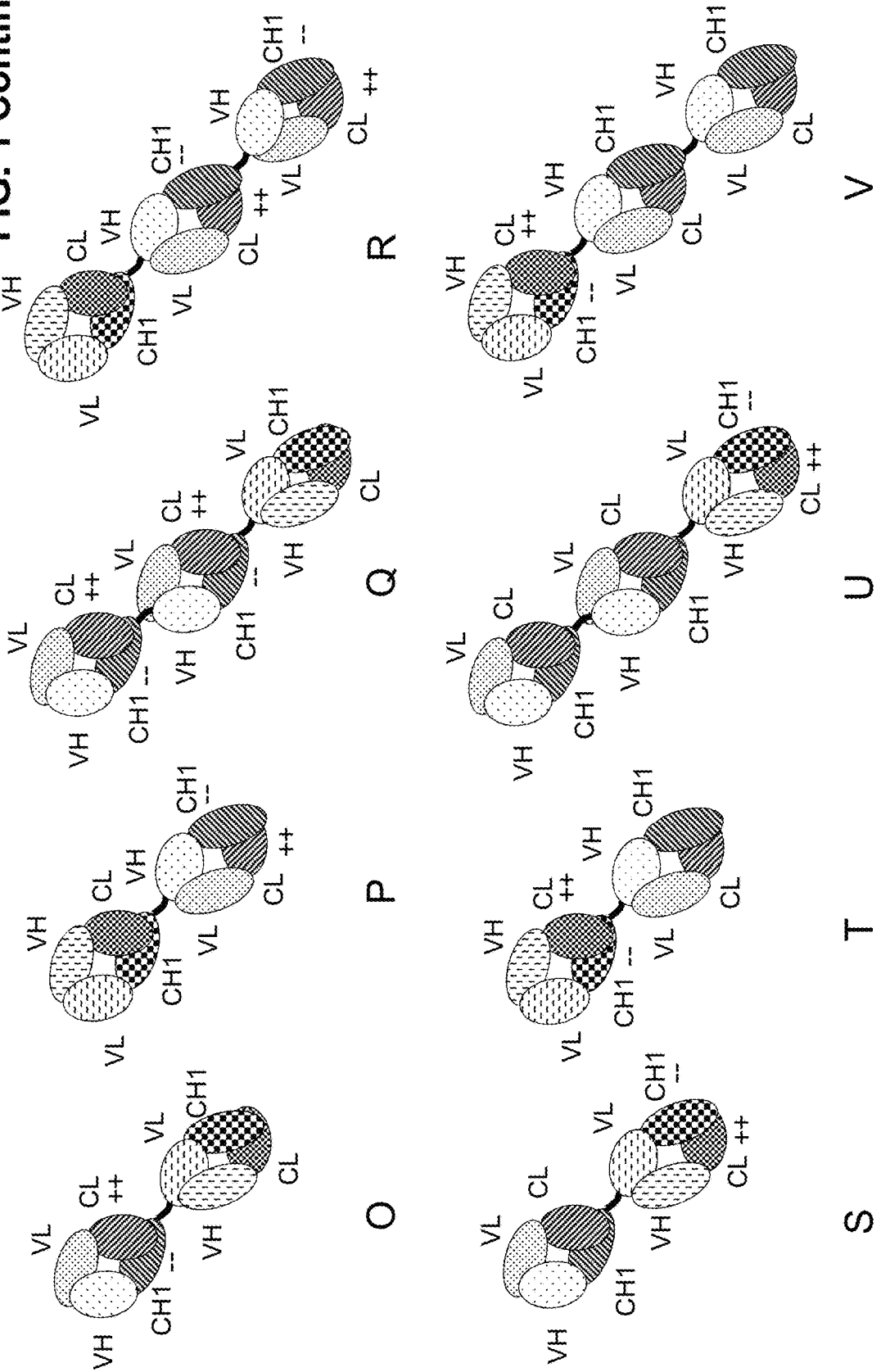

ANTIBODIES BINDING TO CD3 AND CD19

CROSS REFERENCE TO RELATED APPLICATIONS

This application claims benefit to U.S. application Ser. No. 17/350,111, filed Jun. 17, 2021, which claims benefit to European Patent Application No. 20181056.1, filed Jun. 19, 2020, the entire contents of which are incorporated herein by reference.

SEQUENCE LISTING

This application contains a Sequence Listing, which has been submitted electronically via Patent Center in XML format and is hereby incorporated by reference in its entirety. Said XML copy, created on Jul. 31, 2023, is named 51177-038002_Sequence_Listing_7_31_23.xml and is 56,377 bytes in size.

FIELD OF THE INVENTION

The present invention generally relates to antibodies that bind to CD3 and CD19, e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

CD3 (cluster of differentiation 3) is a protein complex composed of four subunits, the CD3γ chain, the CD3δ chain, and two CDR chains. CD3 associates with the T-cell receptor and the chain to generate an activation signal in T lymphocytes.

CD3 has been extensively explored as drug target. Monoclonal antibodies targeting CD3 have been used as immunosuppressant therapies in autoimmune diseases such as type I diabetes, or in the treatment of transplant rejection. The CD3 antibody muromonab-CD3 (OKT3) was the first monoclonal antibody ever approved for clinical use in humans, in 1985.

A more recent application of CD3 antibodies is in the form of bispecific antibodies, binding CD3 on the one hand and a target cell antigen such as CD19 on the other hand. The simultaneous binding of such an antibody to both of its targets will force a temporary interaction between target cell and T cell, causing activation of any cytotoxic T cell and subsequent lysis of the target cell. Bispecific antibodies binding to CD3 and CD19 are described e.g. in WO 2017/055314.

For therapeutic purposes, an important requirement that antibodies have to fulfill is sufficient stability both in vitro (for storage of the drug) an in vivo (after administration to the patient).

Modifications like asparagine deamidation are typical degradations for recombinant antibodies and can affect both in vitro stability and in vivo biological functions.

Given the tremendous therapeutic potential of antibodies, particularly bispecific antibodies for the activation of T cells, there is a need for CD3 antibodies, including multispecific antibodies, with optimized properties.

SUMMARY OF THE INVENTION

The present invention provides antibodies, including multispecific (e.g. bispecific) antibodies, that bind to CD3 and are resistant to degradation by e.g. asparagine deamidation and thus particularly stable as required for therapeutic purposes. The (multispecific) antibodies provided further combine good efficacy and produceability with low toxicity and favorable pharmacokinetic properties.

As is shown herein, the antibodies, including multispecific antibodies, that bind to CD3, provided by the present invention, retain more than about 90% binding activity to CD3 after 2 weeks at pH 7.4, 37° C., relative to the binding activity after 2 weeks at pH 6, −80° C., as determined by surface plasmon resonance (SPR).

In one aspect, the invention provides an antibody that binds to CD3 and CD19, wherein the antibody comprises (a) a first antigen binding domain that binds to CD3, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10; and (b) a second and optionally a third antigen binding domain that binds to CD19. In one aspect, the VH of the first antigen binding domain comprises an amino acid sequence that is at least about 95%, 96%, 97%, 98%, 99% or 100% identical to the amino acid sequence of SEQ ID NO: 7, and/or the VL of the first antigen binding domain comprises an amino acid sequence that is at least about 95%, 96%, 97%, 98%, 99% or 100% identical to the amino acid sequence of SEQ ID NO: 11.

In a further aspect, the invention provides an antibody that binds to CD3 and CD19, wherein the antibody comprises (a) a first antigen binding domain that binds to CD3 comprising a VH sequence of SEQ ID NO: 7 and a VL sequence of SEQ ID NO: 11; and (b) a second and optionally a third antigen binding domain that binds to CD19.

In one aspect, the first, the second and/or, where present, the third antigen binding domain is a Fab molecule.

In one aspect, the antibody comprises an Fc domain composed of a first and a second subunit. In one aspect the first antigen binding domain is a Fab molecule wherein the variable domains VL and VH or the constant domains CL and CH1, particularly the variable domains VL and VH, of the Fab light chain and the Fab heavy chain are replaced by each other.

In one aspect the second and, where present, the third antigen binding domain is a conventional Fab molecule.

In one aspect, the second and, where present, the third antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, the first and the second antigen binding domain are fused to each other, optionally via a peptide linker.

In one aspect, the first and the second antigen binding domain are each a Fab molecule and either (i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.

In one aspect, the first, the second and, where present, the third antigen binding domain are each a Fab molecule and the antibody comprises an Fc domain composed of a first and a second subunit; and wherein either (i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and the third antigen binding domain, where present, is fused at the C-terminus of the Fab heavy chain to the N-terminus of the second subunit of the Fc domain.

In one aspect, the Fc domain is an IgG, particularly an $IgG_1$, Fc domain. In one aspect the Fc domain is a human Fc domain. In one aspect, the Fc comprises a modification promoting the association of the first and the second subunit of the Fc domain. In one aspect, the Fc domain comprises one or more amino acid substitution that reduces binding to an Fc receptor and/or effector function.

In one aspect, the second and, where present, the third antigen binding domain comprises (i) a VH comprising a HCDR 1 of SEQ ID NO: 15, a HCDR 2 of SEQ ID NO: 16, and a HCDR 3 of SEQ ID NO: 17, and a VL comprising a LCDR 1 of SEQ ID NO: 19, a LCDR 2 of SEQ ID NO: 20 and a LCDR 3 of SEQ ID NO: 21; or (ii) a VH comprising a HCDR 1 of SEQ ID NO: 28, a HCDR 2 of SEQ ID NO: 29, and a HCDR 3 of SEQ ID NO: 30, and a VL comprising a LCDR 1 of SEQ ID NO: 32, a LCDR 2 of SEQ ID NO: 33 and a LCDR 3 of SEQ ID NO: 34. In one aspect, the second and, where present, the third antigen binding domain comprises (i) a VH comprising an amino acid sequence that is at least about 95%, 96%, 97%, 98%, 99% or 100% identical to the amino acid sequence of SEQ ID NO: 18, and/or a VL comprising an amino acid sequence that is at least about 95%, 96%, 97%, 98%, 99% or 100% identical to the amino acid sequence of SEQ ID NO: 22; or (ii) a VH comprising an amino acid sequence that is at least about 95%, 96%, 97%, 98%, 99% or 100% identical to the amino acid sequence of SEQ ID NO: 31, and/or a VL comprising an amino acid sequence that is at least about 95%, 96%, 97%, 98%, 99% or 100% identical to the amino acid sequence of SEQ ID NO: 35.

According to a further aspect of the invention there is provided an isolated polynucleotide encoding an antibody of the invention, and a host cell comprising the isolated polynucleotide of the invention.

In another aspect is provided a method of producing an antibody that binds to CD3 and CD19, comprising the steps of (a) culturing the host cell of the invention under conditions suitable for the expression of the antibody and optionally (b) recovering the antibody. The invention also encompasses an antibody that binds to CD3 and CD19 produced by the method of the invention. The invention further provides a pharmaceutical composition comprising the antibody of the invention and a pharmaceutically acceptable carrier.

Also encompassed by the invention are methods of using the antibody and pharmaceutical composition of the invention. In one aspect the invention provides an antibody or pharmaceutical composition according to the invention for use as a medicament. In one aspect is provided an antibody or pharmaceutical composition according to the invention for use in the treatment of a disease. Also provided is the use of an antibody or pharmaceutical composition according to the invention in the manufacture of a medicament, and the use of an antibody or pharmaceutical composition according to the invention in the manufacture of a medicament for the treatment of a disease. The invention also provides a method of treating a disease in an individual, comprising administering to said individual an effective amount of the antibody or pharmaceutical composition according to the invention. In certain aspects the disease is cancer. In other aspects the disease is an autoimmune disease.

DETAILED DESCRIPTION OF THE INVENTION

I. Definitions

Figure 1:
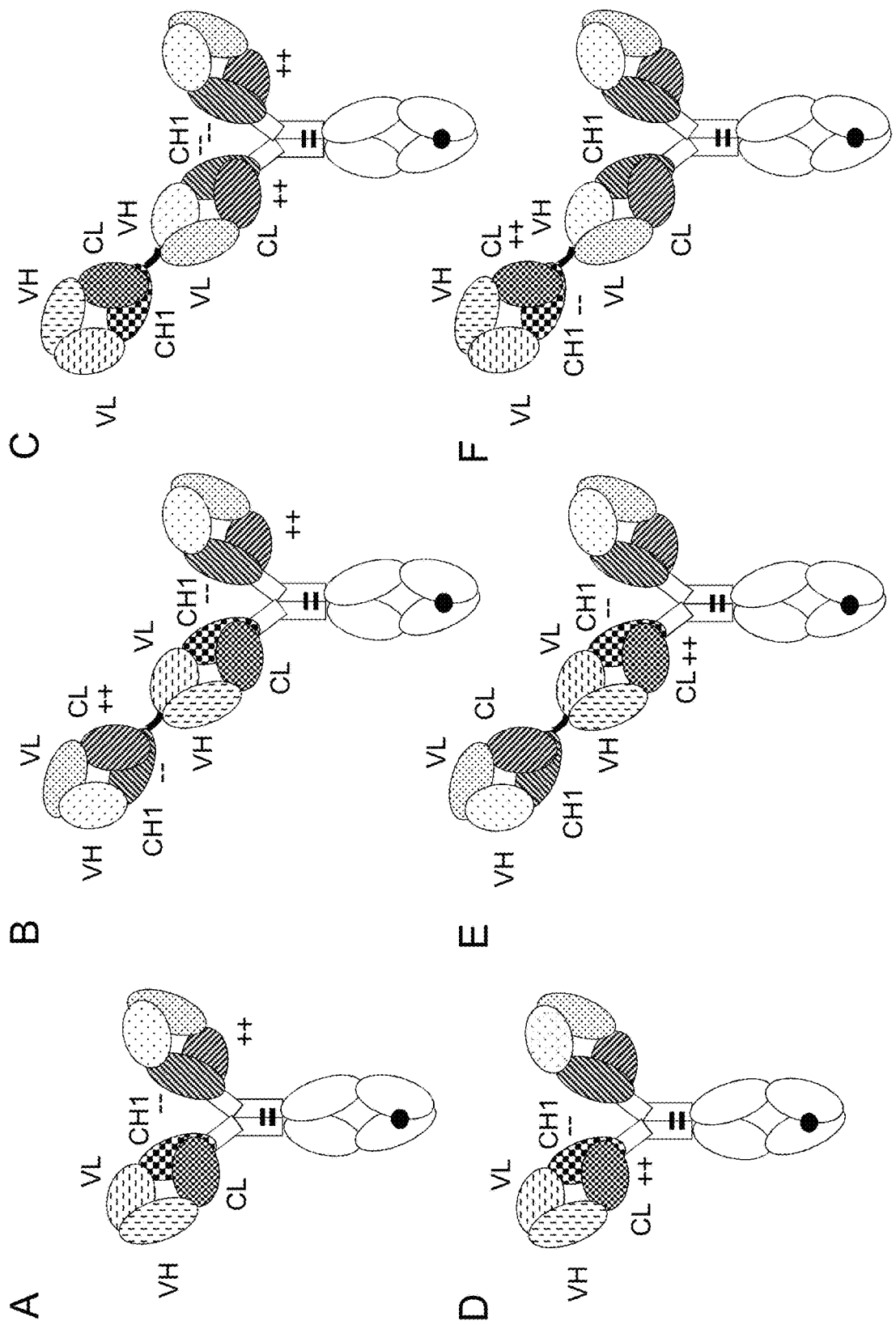
FIG. 1. Exemplary configurations of the (multispecific) antibodies of the invention. (A, D) Illustration of the "1+1 CrossMab" molecule. (B, E) Illustration of the "2+1 IgG Crossfab" molecule with alternative order of Crossfab and Fab components ("inverted"). (C, F) Illustration of the "2+1 IgG Crossfab" molecule. (G, K) Illustration of the "1+1 IgG Crossfab" molecule with alternative order of Crossfab and Fab components ("inverted"). (H, L) Illustration of the "1+1 IgG Crossfab" molecule. (I, M) Illustration of the "2+1 IgG Crossfab" molecule with two CrossFabs. (J, N) Illustration of the "2+1 IgG Crossfab" molecule with two CrossFabs and alternative order of Crossfab and Fab components ("inverted"). (0, S) Illustration of the "Fab-Crossfab" molecule. (P, T) Illustration of the "Crossfab-Fab" molecule. (Q, U) Illustration of the "(Fab)$_2$-Crossfab" molecule. (R, V) Illustration of the "Crossfab-(Fab)$_2$" molecule. (W, Y) Illustration of the "Fab-(Crossfab)$_2$" molecule. (X, Z) Illustration of the "(Crossfab)$_2$-Fab" molecule. Black dot: optional modification in the Fc domain promoting heterodimerization. ++, −−: amino acids of opposite charges optionally introduced in the CH1 and CL domains. Crossfab molecules are depicted as comprising an exchange of VH and VL regions, but may—in aspects wherein no charge modifications are introduced in CH1 and CL domains—alternatively comprise an exchange of the CH1 and CL domains.
Figure 1:
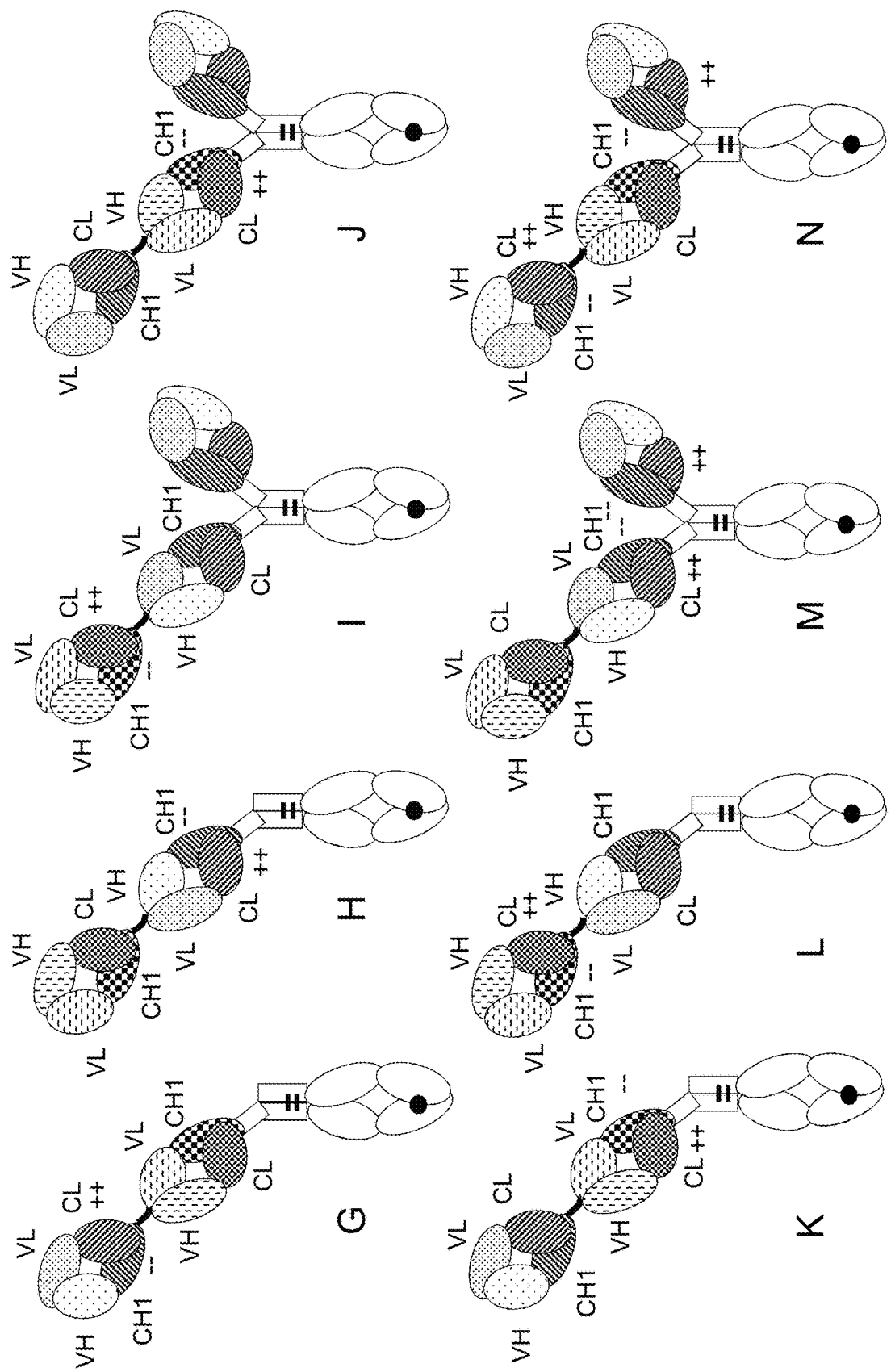
Figure 1:
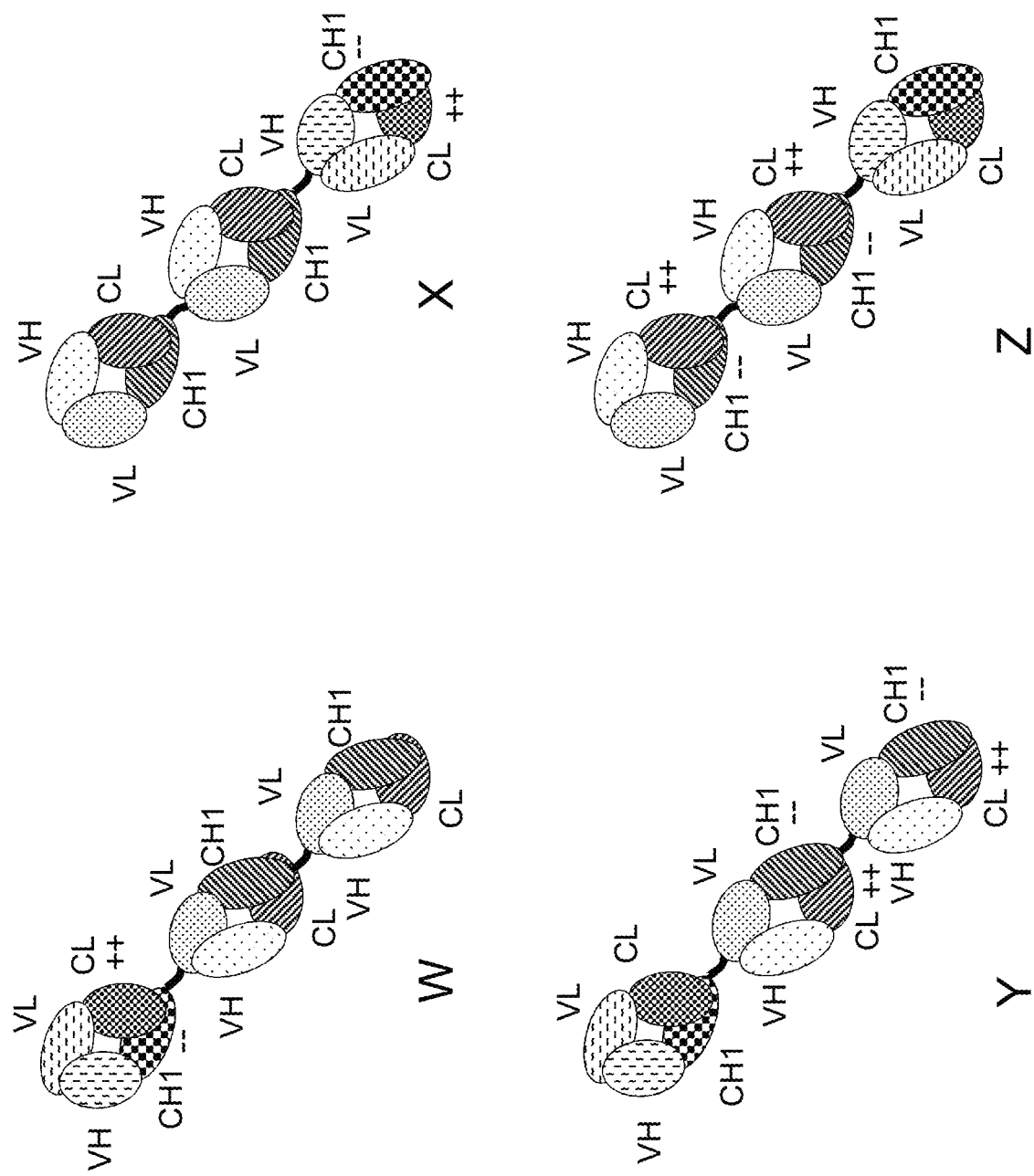

Terms are used herein as generally used in the art, unless otherwise defined in the following. As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one aspect, the extent of binding of an anti-CD3 antibody to an unrelated, non-CD3 protein is less than about 10% of the binding of the antibody to CD3 as measured, e.g., by surface plasmon resonance (SPR). In certain aspects, an antibody that binds to CD3 has a dissociation constant (K D) of ≤1 μM, ≤500 nM, ≤200 nM, or ≤100 nM. An antibody is said to "specifically bind" to CD3 when the antibody has a $K_D$ of 1 μM or less, as measured, e.g., by SPR. In certain aspects, an anti-CD3 antibody binds to an epitope of CD3 that is conserved among CD3 from different species.

Similarly, the terms "anti-CD19 antibody" and "an antibody that binds to CD19" refer to an antibody that is capable of binding CD19 with sufficient affinity such that the antibody is useful as a diagnostic and/or therapeutic agent in targeting CD19. In one aspect, the extent of binding of an anti-CD19 antibody to an unrelated, non-CD19 protein is less than about 10% of the binding of the antibody to CD19 as measured, e.g., by surface plasmon resonance (SPR). In certain aspects, an antibody that binds to CD19 has a dissociation constant ($K_D$) of ≤1 μM, ≤500 nM, ≤200 nM, or ≤100 nM. An antibody is said to "specifically bind" to CD19 when the antibody has a $K_D$ of 1 μM or less, as measured, e.g., by SPR. In certain aspects, an anti-CD19 antibody binds to an epitope of CD19 that is conserved among CD19 from different species.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv and scFab), single-domain antibodies, and multispecific antibodies formed from antibody fragments. For a review of certain antibody fragments, see Hollinger and Hudson, Nature Biotechnology 23:1126-1136 (2005).

The terms "full-length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC, affinity chromatography, size exclusion chromatography) methods. For review of methods for assessment of antibody purity, see, e.g., Flatman et al., *J. Chromatogr. B* 848:79-87 (2007). In some aspects, the antibodies provided by the present invention are isolated antibodies.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some aspects, some FR residues in a humanized antibody are substituted with corresponding residues from a non-human antibody (e.g., the antibody from which the CDR residues are derived), e.g., to restore or improve antibody specificity or affinity. A "humanized form" of an antibody, e.g. of a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain aspects, a human antibody is derived from a non-human transgenic mammal, for example a mouse, a rat, or a rabbit. In certain aspects, a human antibody is derived from a hybridoma cell line. Antibodies or antibody fragments isolated from human antibody libraries are also considered human antibodies or human antibody fragments herein.

The term "antigen binding domain" refers to the part of an antibody that comprises the area which binds to and is complementary to part or all of an antigen. An antigen binding domain may be provided by, for example, one or more antibody variable domains (also called antibody variable regions). In preferred aspects, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and complementarity determining regions (CDRs). See, e.g., Kindt et al., *Kuby Immunology*, 6$^{th}$ ed., W.H. Freeman & Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, hinge, CH2 and CH3), which is herein further clarified by referring to "numbering according to Kabat EU index" or "Kabat EU index numbering" in this case. The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); and
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system. "Framework" or "FR" refers to variable domain residues other than complementarity determining regions (CDRs). The FR of a variable domain generally consists of four FR domains: FR1, FR2, FR3, and FR4. Accordingly, the HVR and FR sequences generally appear in the following order in VH (or VL): FR1-HCDR1(LCDR1)-FR2-HCDR2(LCDR2)-FR3-HCDR3(LCDR3)-FR4. Unless otherwise indicated, CDR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes is 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence. A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3.

The term "immunoglobulin molecule" herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "Fc domain" or "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region (or a subunit of an Fc domain as defined herein) are denoted herein without C-terminal glycine-lysine dipeptide if not indicated otherwise. In one aspect, a heavy chain including an Fc region (subunit) as specified herein, comprised in an antibody according to the invention, comprises an additional C-terminal glycine-lysine dipeptide (G446 and K447, numbering according to Kabat EU index). In one aspect, a heavy chain including an Fc region (subunit) as specified herein, comprised in an antibody according to the invention, comprises an additional C-terminal glycine residue (G446, numbering according to Kabat EU index). Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, M D, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain. By "fused" is meant that the components (e.g. a Fab molecule and an Fc domain subunit) are linked by peptide bonds, either directly or via one or more peptide linkers.

The term "multispecific" means that the antibody is able to specifically bind to at least two distinct antigenic determinants. A multispecific antibody can be, for example, a bispecific antibody. Typically, a bispecific antibody comprises two antigen binding sites, each of which is specific for a different antigenic determinant. In certain aspects the multispecific (e.g. bispecific) antibody is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigenic determinant" or "antigen" refers to a site (e.g. a contiguous stretch of amino acids or a conformational configuration made up of different regions of non-contiguous amino acids) on a polypeptide macromolecule to which an antigen binding domain binds, forming an antigen binding domain-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). In a preferred aspect, the antigen is a human protein. "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one aspect, CD3 is human CD3, particularly the epsilon subunit of human CD3 (CD3c). The amino acid sequence of human CD3ε is shown in SEQ ID NO: 45 (without signal peptide). See also UniProt (www.uniprot.org) accession no. P07766 (version 209), or NCBI (www.ncbi.nlm.nih.gov/) RefSeq NP 000724.1. In another aspect, CD3 is cynomolgus (*Macaca fascicularis*) CD3, particularly cynomolgus CD3ε. The amino acid sequence of cynomolgus CD3ε is shown in SEQ ID NO: 46 (without signal peptide). See also NCBI GenBank no. BAB71849.1. In certain aspects the antibody of the invention binds to an epitope of CD3 that is conserved among the CD3 antigens from different species, particularly human and cynomolgus CD3. In preferred aspects, the antibody binds to human CD3.

A "target cell antigen" as used herein refers to an antigenic determinant presented on the surface of a target cell, for example a B-cell. Preferably, the target cell antigen is not CD3, and/or is expressed on a different cell than CD3. According to the invention, the target cell antigen is CD19, particularly human CD19.

"CD19" stands for cluster of differentiation 19 (also known as B-lymphocyte antigen CD19 or B-lymphocyte surface antigen B4) and refers to any native CD19 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD19 as well as any form of CD19 that results from processing in the cell. The term also encompasses naturally occurring variants of CD19, e.g., splice variants or allelic variants. In one aspect, CD19 is human CD19. See for the human protein UniProt (www.uniprot.org) accession no. P15391 (version 211), or NCBI (www.ncbi.nlm.nih.gov/) RefSeq NP_001761.3. In certain aspects the antibody of the invention binds to an epitope of CD19 that is conserved among the CD19 antigens from different species, particularly human and cynomolgus CD19. In preferred aspects, the antibody binds to human CD19.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., an antibody and an antigen). The affinity of a molecule X for its partner Y can generally be represented by the dissociation constant ($K_D$). Affinity can be measured by well-established methods known in the art, including those described herein. A preferred method for measuring affinity is Surface Plasmon Resonance (SPR).

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein preferably includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which may be non-identical in the sense that further components fused to each of the subunits (e.g. antigen binding domains) are not the same. In some aspects, the modification promoting the association of the first and the second subunit of the Fc domain comprises an amino acid mutation in the Fc domain, specifically an amino acid substitution. In a preferred aspect, the modification promoting the association of the first and the second subunit of the Fc domain comprises a separate amino acid mutation, specifically an amino acid substitution, in each of the two subunits of the Fc domain. The term "effector functions" refers to those biological activities attributable to the Fc region of an antibody, which vary with the antibody isotype. Examples of antibody effector functions include: C1 q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Preferred amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, $G_{329}$, G329, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, % amino acid sequence identity values are generated using the ggsearch program of the FASTA package version 36.3.8c or later with a BLOSUM50 comparison matrix. The FASTA program package was authored by W. R. Pearson and D. J. Lipman ("Improved Tools for Biological Sequence Analysis", PNAS 85 (1988) 2444-2448), W. R. Pearson ("Effective protein sequence comparison" Meth. Enzymol. 266 (1996) 227-258), and Pearson et. al. (Genomics 46 (1997) 24-36) and is publicly available from www.fasta.bioch.virginia.edu/fasta www2/fasta down.shtml or www.ebi.ac.uk/Tools/sss/fasta. Alternatively, a public server accessible at fasta.bioch.virginia.edu/fasta www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" or "nucleic acid molecule" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

An "isolated" nucleic acid molecule refers to a nucleic acid molecule that has been separated from a component of its natural environment. An isolated nucleic acid molecule includes a nucleic acid molecule contained in cells that ordinarily contain the nucleic acid molecule, but the nucleic acid molecule is present extrachromosomally or at a chromosomal location that is different from its natural chromosomal location.

"Isolated polynucleotide (or nucleic acid) encoding an antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one aspect, the host cell of the invention is a eukaryotic cell, particularly a mammalian cell. In one aspect, the host cell is not a cell within a human body.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human.

An "effective amount" of an agent, e.g., a pharmaceutical composition, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

II. Compositions and Methods

The invention provides antibodies that bind CD3 and CD19. The antibodies show superior stability, combined with other favorable properties for therapeutic application, e.g. with respect to efficacy and safety, pharmacokinetics, as well as produceability. Antibodies of the invention as useful, e.g., for the treatment of diseases such as cancer or autoimmune disease.

A. Anti-CD3/CD19 Antibodies

In one aspect, the invention provides antibodies that bind to CD3 and CD19. In one aspect, provided are isolated antibodies that bind to CD3 and CD19. In one aspect, the invention provides antibodies that specifically bind to CD3 and CD19. In certain aspects, the anti-CD3/CD19 antibodies retain more than about 90% binding activity to CD3 after 2 weeks at pH 7.4, 37° C., relative to the binding activity after 2 weeks at pH 6, −80° C., as determined by surface plasmon resonance (SPR).

In one aspect, the invention provides an antibody that binds to CD3 and CD19, wherein the antibody comprises (a) a first antigen binding domain that binds to CD3, comprising a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10.

In one aspect, the antibody is a humanized antibody. In one aspect, the first antigen binding domain is a humanized antigen binding domain (i.e. an antigen binding domain of a humanized antibody). In one aspect, the VH and/or the VL of the first antigen binding domain is a humanized variable region.

In one aspect, the VH and/or the VL of the first antigen binding domain comprises an acceptor human framework, e.g. a human immunoglobulin framework or a human consensus framework. In one aspect, the VH of the first antigen binding domain comprises one or more heavy chain framework sequence (i.e. the FR1, FR2, FR3 and/or FR4 sequence) of the heavy chain variable region sequence of SEQ ID NO: 7. In one aspect, the VH of the first antigen binding domain comprises an amino acid sequence that is at least about 95%, 96%, 97%, 98%, or 99% identical to the amino acid sequence of SEQ ID NO: 7. In one aspect, the VH of the first antigen binding domain comprises an amino acid sequence that is at least about 95% identical to the amino acid sequence of SEQ ID NO: 7. In one aspect, the VH of the first antigen binding domain comprises an amino acid sequence that is at least about 98% identical to the amino acid sequence of SEQ ID NO: 7. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 7. In certain aspects, substitutions, insertions, or deletions occur in regions outside the CDRs (i.e., in the FRs). In one aspect, the VH of the first antigen binding domain comprises the amino acid sequence of SEQ ID NO: 7. Optionally, the VH of the first antigen binding domain comprises the amino acid sequence of SEQ ID NO: 7, including post-translational modifications of that sequence.

In one aspect, the VL of the first antigen binding domain comprises one or more light chain framework sequence (i.e. the FR1, FR2, FR3 and/or FR4 sequence) of the light chain variable region sequence of SEQ ID NO: 11. In one aspect, the VL of the first antigen binding domain comprises an amino acid sequence that is at least about 95%, 96%, 97%, 98%, or 99% identical to the amino acid sequence of SEQ ID NO: 11. In one aspect, the VL of the first antigen binding domain comprises an amino acid sequence that is at least about 95% identical to the amino acid sequence of SEQ ID NO: 11. In one aspect, the VL of the first antigen binding domain comprises an amino acid sequence that is at least about 98% identical to the amino acid sequence of SEQ ID NO: 11. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to CD3. In certain aspects, a total of 1 to 10 amino acids have been substituted, inserted and/or deleted in the amino acid sequence of SEQ ID NO: 11. In certain aspects, substitutions, insertions, or deletions occur in regions outside the CDRs (i.e., in the FRs). In one aspect, the VL of the first antigen binding domain comprises the amino acid sequence of SEQ ID NO: 11. Optionally, the VL of the first antigen binding domain comprises the amino acid sequence of SEQ ID NO: 11, including post-translational modifications of that sequence.

In one aspect, the VH of the first antigen binding domain comprises an amino acid sequence that is at least about 95%, 96%, 97%, 98%, or 99% identical to the amino acid sequence of SEQ ID NO: 7, and the VL of the first antigen binding domain comprises an amino acid sequence that is at least about 95%, 96%, 97%, 98%, or 99% identical to the amino acid sequence of SEQ ID NO: 11. In one aspect, the VH of the first antigen binding domain comprises the amino acid sequence of SEQ ID NO: 7 and the VL of the first antigen binding domain comprises the amino acid sequence of SEQ ID NO: 11.

In a further aspect, the invention provides an antibody that binds to CD3 and CD19, wherein the antibody comprises a first antigen binding domain that binds to CD3 comprising a VH comprising the amino acid sequence of SEQ ID NO: 7 and a VL comprising the amino acid sequence of SEQ ID NO: 11.

In a further aspect, the invention provides an antibody that binds to CD3 and CD19, wherein the antibody comprises a first antigen binding domain that binds to CD3 comprising a VH sequence of SEQ ID NO: 7 and a VL sequence of SEQ ID NO: 11.

In another aspect, the invention provides an antibody that binds to CD3 and CD19, wherein the antibody comprises a first antigen binding domain that binds to CD3 comprising a VH comprising the heavy chain CDR sequences of the VH of SEQ ID NO: 7, and a VL comprising the light chain CDR sequences of the VL of SEQ ID NO: 11.

In a further aspect, the first antigen binding domain comprises the HCDR1, HCDR2 and HCDR3 amino acid sequences of the VH of SEQ ID NO: 7 and the LCDR1, LCDR2 and LCDR3 amino acid sequences of the VL of SEQ ID NO: 11.

In one aspect, the VH of the first antigen binding domain comprises the heavy chain CDR sequences of the VH of SEQ ID NO: 7 and a framework of at least 95%, 96%, 97%, 98% or 99% sequence identity to the framework sequence of the VH of SEQ ID NO: 7. In one aspect, the VH of the first antigen binding domain comprises the heavy chain CDR sequences of the VH of SEQ ID NO: 7 and a framework of at least 95% sequence identity to the framework sequence of the VH of SEQ ID NO: 7. In another aspect, the VH of the first antigen binding domain comprises the heavy chain CDR sequences of the VH of SEQ ID NO: 7 and a framework of at least 98% sequence identity to the framework sequence of the VH of SEQ ID NO: 7.

In one aspect, the VL of the first antigen binding domain comprises the light chain CDR sequences of the VL of SEQ ID NO: 11 and a framework of at least 95%, 96%, 97%, 98% or 99% sequence identity to the framework sequence of the VL of SEQ ID NO: 11. In one aspect, the VL of the first antigen binding domain comprises the light chain CDR sequences of the VL of SEQ ID NO: 11 and a framework of at least 95% sequence identity to the framework sequence of the VL of SEQ ID NO: 11. In another aspect, the VL of the first antigen binding domain comprises the light chain CDR sequences of the VL of SEQ ID NO: 11 and a framework of at least 98% sequence identity to the framework sequence of the VL of SEQ ID NO: 11.

In one aspect, the invention provides an antibody that binds to CD3 and CD19, wherein the antibody comprises a first antigen binding domain that binds to CD3 comprising a VH sequence as in any of the aspects provided above, and a VL sequence as in any of the aspects provided above. In one aspect, the antibody comprises a human constant region. In one aspect, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 52 and 53 (human kappa and lambda CL domains, respectively) and SEQ ID NO: 54 (human IgG$_1$ heavy chain constant domains CH1-CH2-CH3). In one aspect, the antibody comprises a light chain constant region comprising an amino acid sequence that is at least about 95%, 96%, 97%, 98%, 99% or 100% identical to the amino acid sequence of SEQ ID NO: 52 or SEQ ID NO: 53, particularly the amino acid sequence of SEQ ID NO: 52. In one aspect, the antibody comprises a heavy chain constant region comprising an amino acid sequence that is at least about 95%, 96%, 97%, 98%, 99% or 100% identical to the amino acid sequence of SEQ ID NO: 54. Particularly, the heavy chain constant region may comprise amino acid mutations in the Fc domain as described herein.

In one aspect, the first antigen binding domain comprises a human constant region. In one aspect, the first antigen binding moiety is a Fab molecule comprising a human constant region, particularly a human CH1 and/or CL domain. In one aspect, the first antigen binding domain comprises a light chain constant region comprising an amino acid sequence that is at least about 95%, 96%, 97%, 98%, 99% or 100% identical to the amino acid sequence of SEQ ID NO: 52 or SEQ ID NO: 53, particularly the amino acid sequence of SEQ ID NO: 52. Particularly, the light chain constant region may comprise amino acid mutations as described herein under "charge modifications" and/or may comprise deletion or substitutions of one or more (particularly two)N-terminal amino acids if in a crossover Fab molecule. In some aspects, the first antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 54. Particularly, the heavy chain constant region (specifically CH1 domain) may comprise amino acid mutations as described herein under "charge modifications". In one aspect, the antibody is a monoclonal antibody.

In one aspect, the antibody is an IgG, particularly an IgG$_1$, antibody. In one aspect, the antibody is a full-length antibody.

In another aspect, the antibody is an antibody fragment selected from the group of an Fv molecule, a scFv molecule, a Fab molecule, and a F(ab')$_2$ molecule; particularly a Fab molecule. In another aspect, the antibody fragment is a diabody, a triabody or a tetrabody.

In one aspect, the first antigen binding domain is a Fab molecule. In a preferred aspect the first antigen binding domain is a Fab molecule wherein the variable domains VL and VH or the constant domains CL and CH1, particularly the variable domains VL and VH, of the Fab light chain and the Fab heavy chain are replaced by each other (i.e. the first antigen binding domain is a crossover Fab molecule).

In a further aspect, the antibody according to any of the above aspects may incorporate any of the features, singly or in combination, as described in sections II. A. 1.-8. below.

In a preferred aspect, the antibody comprises an Fc domain, particularly an IgG Fc domain, more particularly an IgG$_1$ Fc domain. In one aspect the Fc domain is a human Fc domain. In one aspect, the Fc domain is a human IgG$_1$ Fc domain. The Fc domain is composed of a first and a second subunit and may incorporate any of the features, singly or in combination, described hereinbelow in relation to Fc domain variants (section II. A. 8.).

According to the invention, the antibody comprises a second and optionally a third antigen binding domain which binds to CD19 (i.e. the antibody is a multispecific antibody, as further described hereinbelow (section II. A. 7.).

1. Antibody Fragments

In certain aspects, an antibody provided herein is an antibody fragment.

In one aspect, the antibody fragment is a Fab, Fab', Fab'-SH, or F(ab')$_2$ molecule, in particular a Fab molecule as described herein. "Fab' molecule" differ from Fab molecules by the addition of residues at the carboxy terminus of the CH1 domain including one or more cysteines from the antibody hinge region. Fab'-SH are Fab' molecules in which the cysteine residue(s) of the constant domains bear a free thiol group. Pepsin treatment yields an F(ab')$_2$ molecule that has two antigen-binding sites (two Fab molecules) and a part of the Fc region.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab molecule. A "single chain Fab molecule" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab molecules are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

2. Humanized Antibodies

In certain aspects, an antibody provided herein is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., Methods 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. J. Immunol., 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

3. Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87:614-622 (2004); Kanda, Y. et al., Biotechnol. Bioeng., 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

4. Cysteine Engineered Antibody Variants

In certain aspects, it may be desirable to create cysteine engineered antibodies, e.g., THIOMAB™ antibodies, in which one or more residues of an antibody are substituted with cysteine residues. In preferred aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

5. Antibody Derivatives

In certain aspects, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

6. Immunoconjugates

The invention also provides immunoconjugates comprising an anti-CD3/CD19 antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in Pharmacol Review 68:3-19 (2016).

In another aspect, an immunoconjugate comprises an antibody of the invention conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody of the invention conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as $I^{123}$, $I^{131}$, $In^{111}$, $F^{19}$, $C^{13}$, $N^{15}$, $O^{17}$, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

7. Multispecific Antibodies

An antibody provided herein is a multispecific antibody, particularly a bispecific antibody. Multispecific antibodies are monoclonal antibodies that have binding specificities for at least two different antigenic determinants (e.g., two different proteins, or two different epitopes on the same protein). In certain aspects, the multispecific antibody has three or more binding specificities. According to the present invention, one of the binding specificities is for CD3 and the other specificity is for CD19.

Multispecific antibodies may be prepared as full length antibodies or antibody fragments. Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The multispecific antibody or antigen binding fragment thereof also includes a "Dual Acting FAb" or "DAF" comprising an antigen binding site that binds to CD3 as well as another different antigen, or two different epitopes of CD3 (see, e.g., US 2008/0069820 and WO 2015/095539).

Multi-specific antibodies may also be provided in an asymmetric form with a domain crossover in one or more binding arms of the same antigen specificity (so-called "CrossMab" technology), i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

A particular type of multispecific antibodies are bispecific antibodies designed to simultaneously bind to a surface antigen on a target cell, e.g., a B cell, and to an activating, invariant component of the T cell receptor (TCR) complex, such as CD3, for retargeting of T cells to kill target cells. Hence, the antibody provided herein is a multispecific antibody, particularly a bispecific antibody, wherein one of the binding specificities is for CD3 and the other is for CD19 as the target cell antigen.

Examples of bispecific antibody formats that may be useful for this purpose include, but are not limited to, the so-called "BITE" (bispecific T cell engager) molecules wherein two scFv molecules are fused by a flexible linker (see, e.g., WO 2004/106381, WO 2005/061547, WO 2007/042261, and WO 2008/119567, Nagorsen and Bauerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

Preferred aspects of the antibody of the present invention are described in the following. In one aspect, the invention provides an antibody that binds to CD3 and CD19, comprising a first antigen binding domain that binds to CD3, as described herein, and comprising a second and optionally a third antigen binding domain that binds to CD19.

According to preferred aspects of the invention, the antigen binding domains comprised in the antibody are Fab molecules (i.e. antigen binding domains composed of a heavy and a light chain, each comprising a variable and a constant domain). In one aspect, the first, the second and/or, where present, the third antigen binding domain is a Fab molecule. In one aspect, said Fab molecule is human. In a preferred aspect, said Fab molecule is humanized. In yet another aspect, said Fab molecule comprises human heavy and light chain constant domains.

Preferably, at least one of the antigen binding domains is a crossover Fab molecule. Such modification reduces mispairing of heavy and light chains from different Fab molecules, thereby improving the yield and purity of the (multispecific) antibody of the invention in recombinant production. In a preferred crossover Fab molecule useful for the (multispecific) antibody of the invention, the variable domains of the Fab light chain and the Fab heavy chain (VL and VH, respectively) are exchanged. Even with this domain exchange, however, the preparation of the (multispecific) antibody may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired (multispecific) antibody, charged amino acids with opposite charges may be introduced at specific amino acid positions in the CH1 and CL domains of either the Fab molecule binding to CD3, or the Fab molecule(s) binding to CD19, as further described herein. Charge modifications are made either in the conventional Fab molecule(s) comprised in the (multispecific) antibody (such as shown e.g. in FIGS. 1A-C, G-J), or in the VH/VL crossover Fab molecule(s) comprised in the (multispecific) antibody (such as shown e.g. in FIG. 1 D-F, K-N) (but not in both). In preferred aspects, the charge modifications are made in the conventional Fab molecule(s) comprised in the (multispecific) antibody (which in preferred aspects bind(s) to CD19).

In a preferred aspect according to the invention, the (multispecific) antibody is capable of simultaneous binding to CD3 and CD19. In one aspect, the (multispecific) antibody is capable of crosslinking a T cell and a target cell by simultaneous binding to CD3 and CD19. In an even more preferred aspect, such simultaneous binding results in lysis of the target cell, particularly a CD19-expressing target cell such as a B-cell. In one aspect, such simultaneous binding results in activation of the T cell. In other aspects, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one aspect, binding of the (multispecific) antibody to CD3 without simultaneous binding to CD19 does not result in T cell activation.

In one aspect, the (multispecific) antibody is capable of re-directing cytotoxic activity of a T cell to a target cell. In a preferred aspect, said re-direction is independent of MHC-mediated peptide antigen presentation by the target cell and and/or specificity of the T cell.

Preferably, a T cell according to any of the aspects of the invention is a cytotoxic T cell. In some aspects the T cell is a $CD4^+$ or a $CD8^+$ T cell, particularly a $CD8^+$ T cell.

a) First Antigen Binding Domain

The (multispecific) antibody of the invention comprises at least one antigen binding domain (the first antigen binding domain) that binds to CD3. In preferred aspects, CD3 is human CD3 (SEQ ID NO: 45) or cynomolgus CD3 (SEQ ID NO: 46) most particularly human CD3. In one aspect the first antigen binding domain is cross-reactive for (i.e. specifically binds to) human and cynomolgus CD3. In some aspects, CD3 is the epsilon subunit of CD3 (CD3 epsilon).

In a preferred aspect, the (multispecific) antibody comprises not more than one antigen binding domain that binds to CD3. In one aspect the (multispecific) antibody provides monovalent binding to CD3.

In one aspect, the antigen binding domain that binds to CD3 is an antibody fragment selected from the group of an Fv molecule, a scFv molecule, a Fab molecule, and a $F(ab')_2$ molecule. In a preferred aspect, the antigen binding domain that binds to CD3 is a Fab molecule.

In preferred aspects, the antigen binding domain that binds to CD3 is a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to CD19 is preferably a conventional Fab molecule. In aspects where there is more than one antigen binding domain, particularly Fab molecule, that binds to CD19 comprised in the (multispecific) antibody, the antigen binding domain that binds to CD3 preferably is a crossover Fab molecule and the antigen binding domain that bind to CD19 are conventional Fab molecules.

In alternative aspects, the antigen binding domain that binds to CD3 is a conventional Fab molecule. In such aspects, the antigen binding domain(s) that binds CD19 is a crossover Fab molecule as described herein, i.e. a Fab molecule wherein the variable domains VH and VL or the constant domains CH1 and CL of the Fab heavy and light chains are exchanged/replaced by each other. In aspects where there is more than one antigen binding domain, particularly Fab molecule, that binds to CD3 comprised in the (multi specific) antibody, the antigen binding domain that binds to CD19 preferably is a crossover Fab molecule and the antigen binding domains that bind to CD3 are conventional Fab molecules.

In preferred aspects, the first antigen binding domain is a Fab molecule wherein the variable domains VL and VH or the constant domains CL and CH1, particularly the variable domains VL and VH, of the Fab light chain and the Fab heavy chain are replaced by each other (i.e. according to such aspect, the first antigen binding domain is a crossover Fab molecule wherein the variable or constant domains of the Fab light chain and the Fab heavy chain are exchanged). In one such aspect, the second (and the third, if any) antigen binding domain is a conventional Fab molecule. In one aspect, not more than one antigen binding domain that binds to CD3 is present in the (multispecific) antibody (i.e. the antibody provides monovalent binding to CD3).

b) Second (and Third) Antigen Binding Domain

The (multispecific) antibody of the invention comprises at least one antigen binding domain (the second and optionally the third antigen binding domain), particularly a Fab molecule, that binds to CD19. The second antigen binding domain is able to direct the (multispecific) antibody to a target site, for example to a specific type of cell that expresses CD19.

In one aspect, the antigen binding domain that binds to CD19 is an antibody fragment selected from the group of an FIT molecule, a scFv molecule, a Fab molecule, and a $F(ab')_2$ molecule. In a preferred aspect, the antigen binding domain that binds to CD19 is a Fab molecule.

In certain aspects, the (multispecific) antibody comprises two antigen binding domains, particularly Fab molecules, that bind to CD19. In a preferred aspect, all of these antigen binding domains are identical, i.e. they have the same molecular format (e.g. conventional or crossover Fab molecule) and comprise the same amino acid sequences including the same amino acid substitutions in the CH1 and CL domain as described herein (if any). In one aspect, the (multispecific) antibody comprises not more than two antigen binding domains, particularly Fab molecules, that bind to CD19.

In preferred aspects, the antigen binding domain(s) that bind to CD19 is/are a conventional Fab molecule. In such aspects, the antigen binding domain(s) that binds to CD3 is a crossover Fab molecule as described herein, i.e. a Fab molecule wherein the variable domains VH and VL or the constant domains CH1 and CL of the Fab heavy and light chains are exchanged/replaced by each other.

In alternative aspects, the antigen binding domain(s) that bind to CD19 is/are a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to CD3 is a conventional Fab molecule.

In one aspect, the second (and, where present, third) antigen binding domain comprises a human constant region. In one aspect, the second (and, where present, third) antigen binding domain is a Fab molecule comprising a human constant region, particularly a human CH1 and/or CL domain. Exemplary sequences of human constant domains are given in SEQ ID NOs 52 and 53 (human kappa and lambda CL domains, respectively) and SEQ ID NO: 54 (human $IgG_1$ heavy chain constant domains CH1-CH2-CH3). In one aspect, the second (and, where present, third) antigen binding domain comprises a light chain constant region comprising an amino acid sequence that is at least about 95%, 96%, 97%, 98%, 99% or 100% identical to the amino acid sequence of SEQ ID NO: 52 or SEQ ID NO: 53, particularly the amino acid sequence of SEQ ID NO: 52. Particularly, the light chain constant region may comprise amino acid mutations as described herein under "charge modifications" and/or may comprise deletion or substitutions of one or more (particularly two)N-terminal amino acids if in a crossover Fab molecule. In some aspects, the second (and, where present, third) antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 54. Particularly, the heavy chain constant region (specifically CH1 domain) may comprise amino acid mutations as described herein under "charge modifications".

In one aspect, the second (and, where present, the third) antigen binding domain comprises a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody). In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, the third) antigen binding domain comprises one or more heavy chain framework sequence (i.e. the FR1, FR2, FR3 and/or FR4 sequence) of SEQ ID NO: 18. In one aspect, the VH of the second (and, where present, the third) antigen binding domain comprises an amino acid sequence that is at least about 95%, 96%, 97%, 98%, or 99% identical to the amino acid sequence of SEQ ID NO: 18. In one aspect, the VH of the second (and, where present, the third) antigen binding domain comprises an amino acid sequence that is at least about 95% identical to the amino acid sequence of SEQ ID NO: 18. In one aspect, the VH of the second (and, where present, the third) antigen binding domain comprises an amino acid sequence that is at least about 98% identical to the amino acid sequence of SEQ ID NO: 18. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to CD19. In certain aspects, a total of 1 to 10 amino acids have been substituted, inserted and/or deleted in the amino acid sequence of SEQ ID NO: 18. In certain aspects, substitutions, insertions, or deletions occur in regions outside the CDRs (i.e., in the FRs). In one aspect, the VH of the second (and, where present, the third) antigen binding domain comprises the amino acid sequence of SEQ ID NO: 18. Optionally, the VH of the second (and, where present, the third) antigen binding domain comprises the amino acid sequence of SEQ ID NO: 18, including post-translational modifications of that sequence.

In one aspect, the VL of the second (and, where present, the third) antigen binding domain comprises one or more light chain framework sequence (i.e. the FR1, FR2, FR3 and/or FR4 sequence) of SEQ ID NO: 22. In one aspect, the VL of the second (and, where present, the third) antigen binding domain comprises an amino acid sequence that is at least about 95%, 96%, 97%, 98%, or 99% identical to the amino acid sequence of SEQ ID NO: 22. In one aspect, the VL of the second (and, where present, the third) antigen binding domain comprises an amino acid sequence that is at least about 95% identical to the amino acid sequence of SEQ ID NO: 22. In one aspect, the VL of the second (and, where present, the third) antigen binding domain comprises an amino acid sequence that is at least about 98% identical to the amino acid sequence of SEQ ID NO: 22. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to CD19. In certain aspects, a total of 1 to 10 amino acids have been substituted, inserted and/or deleted in the amino acid sequence of SEQ ID NO: 22. In certain aspects, substitutions, insertions, or deletions occur in regions outside the CDRs (i.e., in the FRs). In one aspect, the VL of the second (and, where present, the third) antigen binding domain comprises the amino acid sequence of SEQ ID NO: 22. Optionally, the VL of the second (and, where present, the third) antigen binding domain comprises the amino acid sequence of SEQ ID NO: 22, including post-translational modifications of that sequence.

In one aspect, the VH of the second (and, where present, the third) antigen binding domain comprises an amino acid sequence that is at least about 95%, 96%, 97%, 98%, or 99% identical to the amino acid sequence of SEQ ID NO: 18, and the VL of the second (and, where present, the third) antigen binding domain comprises an amino acid sequence that is at least about 95%, 96%, 97%, 98%, or 99% identical to the amino acid sequence of SEQ ID NO: 22. In one aspect, the VH of the second (and, where present, the third) antigen binding domain comprises the amino acid sequence of SEQ ID NO: 18 and the VL of the second (and, where present, the third) antigen binding domain comprises the amino acid sequence of SEQ ID NO: 22.

In a further aspect, the second (and, where present, the third) antigen binding domain comprises a VH comprising the sequence of SEQ ID NO: 18 and a VL comprising the sequence of SEQ ID NO: 22.

In a further aspect, the second (and, where present, the third) antigen binding domain comprises a VH sequence of SEQ ID NO: 18 and a VL sequence of SEQ ID NO: 22.

In another aspect, the second (and, where present, the third) antigen binding domain comprises a VH comprising the heavy chain CDR sequences of the VH of SEQ ID NO: 18, and a VL comprising the light chain CDR sequences of the VL of SEQ ID NO: 22.

In a further aspect, the second (and, where present, the third) antigen binding domain comprises the HCDR1, HCDR2 and HCDR3 amino acid sequences of the VH of SEQ ID NO: 18 and the LCDR1, LCDR2 and LCDR3 amino acid sequences of the VL of SEQ ID NO: 22.

In one aspect, the VH of the second (and, where present, the third) antigen binding domain comprises the heavy chain CDR sequences of the VH of SEQ ID NO: 18 and a framework of at least 95%, 96%, 97%, 98% or 99% sequence identity to the framework sequence of the VH of SEQ ID NO: 18. In one aspect, the VH of the second (and, where present, the third) antigen binding domain comprises the heavy chain CDR sequences of the VH of SEQ ID NO: 18 and a framework of at least 95% sequence identity to the framework sequence of the VH of SEQ ID NO: 18. In another aspect, the VH of the second (and, where present, the third) antigen binding domain comprises the heavy chain CDR sequences of the VH of SEQ ID NO: 18 and a framework of at least 98% sequence identity to the framework sequence of the VH of SEQ ID NO: 18.

In one aspect, the VL of the second (and, where present, the third) antigen binding domain comprises the light chain CDR sequences of the VL of SEQ ID NO: 22 and a framework of at least 95%, 96%, 97%, 98% or 99% sequence identity to the framework sequence of the VL of SEQ ID NO: 22. In one aspect, the VL of the second (and, where present, the third) antigen binding domain comprises the light chain CDR sequences of the VL of SEQ ID NO: 22 and a framework of at least 95% sequence identity to the framework sequence of the VL of SEQ ID NO: 22. In another aspect, the VL of the second (and, where present, the third) antigen binding domain comprises the light chain CDR sequences of the VL of SEQ ID NO: 22 and a framework of at least 98% sequence identity to the framework sequence of the VL of SEQ ID NO: 22.

In another aspect, the second (and, where present, the third) antigen binding domain comprises a heavy chain variable region (VH) comprising a heavy chain complementary determining region (HCDR) 1 of SEQ ID NO: 28, a HCDR 2 of SEQ ID NO: 29, and a HCDR 3 of SEQ ID NO: 30, and a light chain variable region (VL) comprising a light chain complementarity determining region (LCDR) 1 of SEQ ID NO: 32, a LCDR 2 of SEQ ID NO: 33 and a LCDR 3 of SEQ ID NO: 34.

In one aspect, the second (and, where present, third) antigen binding domain is (derived from) a humanized antibody. In one aspect, the second (and, where present, third) antigen binding domain is a humanized antigen binding domain (i.e. an antigen binding domain of a humanized antibody). In one aspect, the VH and/or the VL of the second (and, where present, third) antigen binding domain is a humanized variable region.

In one aspect, the VH and/or the VL of the second (and, where present, third) antigen binding domain comprises an acceptor human framework, e.g. a human immunoglobulin framework or a human consensus framework.

In one aspect, the VH of the second (and, where present, the third) antigen binding domain comprises one or more heavy chain framework sequence (i.e. the FR1, FR2, FR3 and/or FR4 sequence) of SEQ ID NO: 31. In one aspect, the VH of the second (and, where present, the third) antigen binding domain comprises an amino acid sequence that is at least about 95%, 96%, 97%, 98%, or 99% identical to the amino acid sequence of SEQ ID NO: 31. In one aspect, the VH of the second (and, where present, the third) antigen binding domain comprises an amino acid sequence that is at least about 95% identical to the amino acid sequence of SEQ ID NO: 31. In one aspect, the VH of the second (and, where present, the third) antigen binding domain comprises an amino acid sequence that is at least about 98% identical to the amino acid sequence of SEQ ID NO: 31. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to CD19. In certain aspects, a total of 1 to 10 amino acids have been substituted, inserted and/or deleted in the amino acid sequence of SEQ ID NO: 31. In certain aspects, substitutions, insertions, or deletions occur in regions outside the CDRs (i.e., in the FRs). In one aspect, the VH of the second (and, where present, the third) antigen binding domain comprises the amino acid sequence of SEQ ID NO: 31. Optionally, the VH of the second (and, where present, the third) antigen binding domain comprises the amino acid sequence of SEQ ID NO: 31, including post-translational modifications of that sequence.

In one aspect, the VL of the second (and, where present, the third) antigen binding domain comprises one or more light chain framework sequence (i.e. the FR1, FR2, FR3 and/or FR4 sequence) of SEQ ID NO: 35. In one aspect, the VL of the second (and, where present, the third) antigen binding domain comprises an amino acid sequence that is at least about 95%, 96%, 97%, 98%, or 99% identical to the amino acid sequence of SEQ ID NO: 35. In one aspect, the VL of the second (and, where present, the third) antigen binding domain comprises an amino acid sequence that is at least about 95% identical to the amino acid sequence of SEQ ID NO: 35. In one aspect, the VL of the second (and, where present, the third) antigen binding domain comprises an amino acid sequence that is at least about 98% identical to the amino acid sequence of SEQ ID NO: 35. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to CD19. In certain aspects, a total of 1 to 10 amino acids have been substituted, inserted and/or deleted in the amino acid sequence of SEQ ID NO: 35. In certain aspects, substitutions, insertions, or deletions occur in regions outside the CDRs (i.e., in the FRs). In one aspect, the VL of the second (and, where present, the third) antigen binding domain comprises the amino acid sequence of SEQ ID NO: 35. Optionally, the VL of the second (and, where present, the third) antigen binding domain comprises the amino acid sequence of SEQ ID NO: 35, including post-translational modifications of that sequence.

In one aspect, the VH of the second (and, where present, the third) antigen binding domain comprises an amino acid sequence that is at least about 95%, 96%, 97%, 98%, or 99% identical to the amino acid sequence of SEQ ID NO: 31, and the VL of the second (and, where present, the third) antigen binding domain comprises an amino acid sequence that is at least about 95%, 96%, 97%, 98%, or 99% identical to the amino acid sequence of SEQ ID NO: 35. In one aspect, the VH of the second (and, where present, the third) antigen binding domain comprises the amino acid sequence of SEQ ID NO: 31 and the VL of the second (and, where present, the third) antigen binding domain comprises the amino acid sequence of SEQ ID NO: 35.

In a further aspect, the second (and, where present, the third) antigen binding domain comprises a VH comprising the sequence of SEQ ID NO: 31 and a VL comprising the sequence of SEQ ID NO: 35.

In a further aspect, the second (and, where present, the third) antigen binding domain comprises a VH sequence of SEQ ID NO: 31 and a VL sequence of SEQ ID NO: 35.

In another aspect, the second (and, where present, the third) antigen binding domain comprises a VH comprising the heavy chain CDR sequences of the VH of SEQ ID NO: 31, and a VL comprising the light chain CDR sequences of the VL of SEQ ID NO: 35.

In a further aspect, the second (and, where present, the third) antigen binding domain comprises the HCDR1, HCDR2 and HCDR3 amino acid sequences of the VH of SEQ ID NO: 31 and the LCDR1, LCDR2 and LCDR3 amino acid sequences of the VL of SEQ ID NO: 35.

In one aspect, the VH of the second (and, where present, the third) antigen binding domain comprises the heavy chain CDR sequences of the VH of SEQ ID NO: 31 and a framework of at least 95%, 96%, 97%, 98% or 99% sequence identity to the framework sequence of the VH of SEQ ID NO: 31. In one aspect, the VH of the second (and, where present, the third) antigen binding domain comprises the heavy chain CDR sequences of the VH of SEQ ID NO: 31 and a framework of at least 95% sequence identity to the framework sequence of the VH of SEQ ID NO: 31. In another aspect, the VH of the second (and, where present, the third) antigen binding domain comprises the heavy chain CDR sequences of the VH of SEQ ID NO: 31 and a framework of at least 98% sequence identity to the framework sequence of the VH of SEQ ID NO: 31.

In one aspect, the VL of the second (and, where present, the third) antigen binding domain comprises the light chain CDR sequences of the VL of SEQ ID NO: 35 and a framework of at least 95%, 96%, 97%, 98% or 99% sequence identity to the framework sequence of the VL of SEQ ID NO: 35. In one aspect, the VL of the second (and, where present, the third) antigen binding domain comprises the light chain CDR sequences of the VL of SEQ ID NO: 35 and a framework of at least 95% sequence identity to the framework sequence of the VL of SEQ ID NO: 35. In another aspect, the VL of the second (and, where present, the third) antigen binding domain comprises the light chain CDR sequences of the VL of SEQ ID NO: 35 and a framework of at least 98% sequence identity to the framework sequence of the VL of SEQ ID NO: 35.

c) Charge Modifications

The (multispecific) antibody of the invention may comprise amino acid substitutions in Fab molecules comprised therein which are particularly efficient in reducing mispairing of light chains with non-matching heavy chains (Bence-Jones-type side products), which can occur in the production of Fab-based multi specific antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired (multispecific) antibody compared to undesired side products, in particular Bence Jones-type side products occurring in multispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some aspects wherein the first and the second (and, where present, the third) antigen binding domain of the (multispecific) antibody are both Fab molecules, and in one of the antigen binding domains (particularly the first antigen binding domain) the variable domains VL and VH of the Fab light chain and the Fab heavy chain are replaced by each other,
  i) in the constant domain CL of the second (and, where present, the third) antigen binding domain the amino acid at position 124 is substituted by a positively charged amino acid (numbering according to Kabat), and wherein in the constant domain CH1 of the second (and, where present, the third) antigen binding domain the amino acid at position 147 or the amino acid at position 213 is substituted by a negatively charged amino acid (numbering according to Kabat EU index); or
  ii) in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index).

The (multispecific) antibody does not comprise both modifications mentioned under i) and ii). The constant domains CL and CH1 of the antigen binding domain having the VH/VL exchange are not replaced by each other (i.e. remain unexchanged).

In a more specific aspect,
  i) in the constant domain CL of the second (and, where present, the third) antigen binding domain the amino acid at position 124 is substituted independently by lysine (K), arginine (R) or histidine (H) (numbering according to Kabat), and in the constant domain CH1 of the second (and, where present, the third) antigen binding domain the amino acid at position 147 or the amino acid at position 213 is substituted independently by glutamic acid (E), or aspartic acid (D) (numbering according to Kabat EU index); or
  ii) in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index).

In one such aspect, in the constant domain CL of the second (and, where present, the third) antigen binding domain the amino acid at position 124 is substituted independently by lysine (K), arginine (R) or histidine (H) (numbering according to Kabat), and in the constant domain CH1 of the second (and, where present, the third) antigen binding domain the amino acid at position 147 or the amino acid at position 213 is substituted independently by glutamic acid (E), or aspartic acid (D) (numbering according to Kabat EU index).

In a further aspect, in the constant domain CL of the second (and, where present, the third) antigen binding domain the amino acid at position 124 is substituted independently by lysine (K), arginine (R) or histidine (H) (numbering according to Kabat), and in the constant domain CH1 of the second (and, where present, the third) antigen binding domain the amino acid at position 147 is substituted independently by glutamic acid (E), or aspartic acid (D) (numbering according to Kabat EU index). In a preferred aspect, in the constant domain CL of the second (and, where present, the third) antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second (and, where present, the third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more preferred aspect, in the constant domain CL of the second (and, where present, the third) antigen binding domain the amino acid at position 124 is substituted by lysine (K) (numbering according to Kabat) and the amino acid at position 123 is substituted by lysine (K) (numbering according to Kabat), and in the constant domain CH1 of the second (and, where present, the third) antigen binding domain the amino acid at position 147 is substituted by glutamic acid (E) (numbering according to Kabat EU index) and the amino acid at position 213 is substituted by glutamic acid (E) (numbering according to Kabat EU index).

In an even more preferred aspect, in the constant domain CL of the second (and, where present, the third) antigen binding domain the amino acid at position 124 is substituted by lysine (K) (numbering according to Kabat) and the amino acid at position 123 is substituted by arginine (R) (numbering according to Kabat), and in the constant domain CH1 of the second (and, where present, the third) antigen binding domain the amino acid at position 147 is substituted by glutamic acid (E) (numbering according to Kabat EU index) and the amino acid at position 213 is substituted by glutamic acid (E) (numbering according to Kabat EU index).

In preferred aspects, if amino acid substitutions according to the above aspects are made in the constant domain CL and the constant domain CH1 of the second (and, where present, the third) antigen binding domain, the constant domain CL of the second (and, where present, the third) antigen binding domain is of kappa isotype.

Alternatively, the amino acid substitutions according to the above aspects may be made in the constant domain CL and the constant domain CH1 of the first antigen binding domain instead of in the constant domain CL and the constant domain CH1 of the second (and, where present, the third) antigen binding domain. In preferred such aspects, the constant domain CL of the first antigen binding domain is of kappa isotype.

Accordingly, in one aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index). In a further aspect, in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index).

In still another aspect, in the constant domain CL of the first antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, in the constant domain CL of the first antigen binding domain the amino acid at position 124 is substituted by lysine (K) (numbering according to Kabat) and the amino acid at position 123 is substituted by lysine (K) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In another aspect, in the constant domain CL of the first antigen binding domain the amino acid at position 124 is substituted by lysine (K) (numbering according to Kabat) and the amino acid at position 123 is substituted by arginine (R) (numbering according to Kabat), and in the constant domain CH1 of the first antigen binding domain the amino acid at position 147 is substituted by glutamic acid (E) (numbering according to Kabat EU index) and the amino acid at position 213 is substituted by glutamic acid (E) (numbering according to Kabat EU index).

In a preferred aspect, the (multispecific) antibody of the invention comprises (a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10, and (b) a second and optionally a third antigen binding domain that binds CD19;

wherein in the constant domain CL of the second (and, where present, the third) antigen binding domain the amino acid at position 124 is substituted independently by lysine (K), arginine (R) or histidine (H) (numbering according to Kabat) (in a preferred aspect independently by lysine (K) or arginine (R)) and the amino acid at position 123 is substituted independently by lysine (K), arginine (R) or histidine (H) (numbering according to Kabat) (in a preferred aspect independently by lysine (K) or arginine (R)), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

d) Multispecific Antibody Formats

The (multispecific) antibody according to the present invention can have a variety of configurations. Exemplary configurations are depicted in FIG. 1.

In preferred aspects, the antigen binding domains comprised in the (multispecific) antibody are Fab molecules. In such aspects, the first, second, third etc. antigen binding domain may be referred to herein as first, second, third etc. Fab molecule, respectively.

In one aspect, the first and the second antigen binding domain of the (multispecific) antibody are fused to each other, optionally via a peptide linker. In preferred aspects, the first and the second antigen binding domain are each a Fab molecule. In one such aspect, the first antigen binding domain is fused at the C-terminus of the Fab heavy chain to the N-terminus of the Fab heavy chain of the second antigen binding domain. In another such aspect, the second antigen binding domain is fused at the C-terminus of the Fab heavy chain to the N-terminus of the Fab heavy chain of the first antigen binding domain. In aspects wherein either (i) the first antigen binding domain is fused at the C-terminus of the Fab heavy chain to the N-terminus of the Fab heavy chain of the second antigen binding domain or (ii) the second antigen binding domain is fused at the C-terminus of the Fab heavy chain to the N-terminus of the Fab heavy chain of the first antigen binding domain, additionally the Fab light chain of the first antigen binding domain and the Fab light chain of the second antigen binding domain may be fused to each other, optionally via a peptide linker.

A (multispecific) antibody with a single antigen binding domain (such as a Fab molecule) capable of specific binding to a second antigen, e.g. a target cell antigen such as CD19, (for example as shown in FIG. 1A, D, G, H, K, L) is useful, particularly in cases where internalization of the second antigen is to be expected following binding of a high affinity antigen binding domain. In such cases, the presence of more than one antigen binding domain specific for the second antigen may enhance internalization of the second antigen, thereby reducing its availability.

In other cases, however, it will be advantageous to have a (multispecific) antibody comprising two or more antigen binding domains (such as Fab molecules) specific for a second antigen, e.g. a target cell antigen such as CD19 (see examples shown in FIG. 1B, 1C, 1E, 1F, 1I, 1J, 1M or 1N), for example to optimize targeting to the target site or to allow crosslinking of target cell antigens.

Accordingly, in preferred aspects, the (multispecific) antibody according to the present invention comprises a third antigen binding domain.

In one aspect, the third antigen binding domain binds to CD19. In one aspect, the third antigen binding domain is a Fab molecule.

In one aspect, the third antigen domain is identical to the second antigen binding domain.

In some aspects, the third and the second antigen binding domain are each a Fab molecule and the third antigen binding domain is identical to the second antigen binding domain. Thus, in these aspects, the second and the third antigen binding domain comprise the same heavy and light chain amino acid sequences and have the same arrangement of domains (i.e. conventional or crossover). Furthermore, in these aspects, the third antigen binding domain comprises the same amino acid substitutions, if any, as the second antigen binding domain. For example, the amino acid substitutions described herein as "charge modifications" will be made in the constant domain CL and the constant domain CH1 of each of the second antigen binding domain and the third antigen binding domain. Alternatively, said amino acid substitutions may be made in the constant domain CL and the constant domain CH1 of the first antigen binding domain (which in preferred aspects is also a Fab molecule), but not in the constant domain CL and the constant domain CH1 of the second antigen binding domain and the third antigen binding domain.

Like the second antigen binding domain, the third antigen binding domain preferably is a conventional Fab molecule. Aspects wherein the second and the third antigen binding domains are crossover Fab molecules (and the first antigen binding domain is a conventional Fab molecule) are, however, also contemplated. Thus, in preferred aspects, the second and the third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other aspects, the second and the third antigen binding domains are each a crossover Fab molecule and the first antigen binding domain is a conventional Fab molecule. If a third antigen binding domain is present, in a preferred aspect the first antigen domain binds to CD3, and the second and third antigen binding domain bind to CD19.

In preferred aspects, the (multispecific) antibody of the invention comprises an Fc domain composed of a first and a second subunit. The first and the second subunit of the Fc domain are capable of stable association.

The (multispecific) antibody according to the invention can have different configurations, i.e. the first, second (and optionally third) antigen binding domain may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some aspects, the first and the second antigen binding domain are each a Fab molecule and the first antigen binding domain is fused at the C-terminus of the Fab heavy chain to the N-terminus of the first or the second subunit of the Fc domain. In such aspects, the second antigen binding domain may be fused at the C-terminus of the Fab heavy chain to the N-terminus of the Fab heavy chain of the first antigen binding domain or to the N-terminus of the other one of the subunits of the Fc domain. In preferred such aspects, the second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, the second antigen binding domain is a crossover Fab molecule and the first antigen binding domain is a conventional Fab molecule.

In one aspect, the first and the second antigen binding domain are each a Fab molecule, the first antigen binding domain is fused at the C-terminus of the Fab heavy chain to the N-terminus of the first or the second subunit of the Fc domain, and the second antigen binding domain is fused at the C-terminus of the Fab heavy chain to the N-terminus of the Fab heavy chain of the first antigen binding domain. In a specific aspect, the (multispecific) antibody essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 1G and 1K (with the first antigen binding domain in these examples being a VH/VL crossover Fab molecule). Optionally, the Fab light chain of the first Fab molecule and the Fab light chain of the second Fab molecule may additionally be fused to each other.

In another aspect, the first and the second antigen binding domain are each a Fab molecule and the first and the second antigen binding domain are each fused at the C-terminus of the Fab heavy chain to the N-terminus of one of the subunits of the Fc domain. In a specific aspect, the (multispecific) antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIGS. 1A and 1D (in these examples with the first antigen binding domain being a VH/VL crossover Fab molecule and the second antigen binding domain being a conventional Fab molecule). The first and the second Fab molecule may be fused to the Fc domain directly or through a peptide linker. In a preferred aspect the first and the second Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain.

In some aspects, the first and the second antigen binding domain are each a Fab molecule and the second antigen binding domain is fused at the C-terminus of the Fab heavy chain to the N-terminus of the first or the second subunit of the Fc domain. In such aspects, the first antigen binding domain may be fused at the C-terminus of the Fab heavy chain to the N-terminus of the Fab heavy chain of the first antigen binding domain or (as described above) to the N-terminus of the other one of the subunits of the Fc domain. In preferred such aspects, said second antigen binding domain is a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other.

In other such aspects, said second antigen binding domain is a crossover Fab molecule and the first antigen binding domain is a conventional Fab molecule.

In one aspect, the first and the second antigen binding domain are each a Fab molecule, the second antigen binding domain is fused at the C-terminus of the Fab heavy chain to the N-terminus of the first or the second subunit of the Fc domain, and the first antigen binding domain is fused at the C-terminus of the Fab heavy chain to the N-terminus of the Fab heavy chain of the second antigen binding domain. In a specific aspect, the (multispecific) antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 1H and 1L (in these examples with the first antigen binding domain being a VH/VL crossover Fab molecule and the second antigen binding domain being a conventional Fab molecule). Optionally, the Fab light chain of the first Fab molecule and the Fab light chain of the second Fab molecule may additionally be fused to each other.

In some aspects, a third antigen binding domain, particularly a third Fab molecule, is fused at the C-terminus of the Fab heavy chain to the N-terminus of the first or second subunit of the Fc domain. In preferred such aspects, said second and third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said second and third antigen binding domains are each a crossover Fab molecule and the first antigen binding domain is a conventional Fab molecule.

In a preferred such aspect, the first and the third antigen binding domain are each fused at the C-terminus of the Fab heavy chain to the N-terminus of one of the subunits of the Fc domain, and the second antigen binding domain is fused at the C-terminus of the Fab heavy chain to the N-terminus of the Fab heavy chain of the first Fab molecule. In a specific aspect, the (multispecific) antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1B and 1E (in these examples with the first antigen binding domain being a VH/VL crossover Fab molecule, and the second and the third antigen binding domain being a conventional Fab molecule), and FIGS. 1J and 1N (in these examples with the first antigen binding domain being a conventional Fab molecule, and the second and the third antigen binding domain being a VH/VL crossover Fab molecule). The first and the third Fab molecule may be fused to the Fc domain directly or through a peptide linker. In a preferred aspect, the first and the third Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another such aspect, the second and the third antigen binding domain are each fused at the C-terminus of the Fab heavy chain to the N-terminus of one of the subunits of the Fc domain, and the first antigen binding domain is fused at the C-terminus of the Fab heavy chain to the N-terminus of the Fab heavy chain of the second antigen binding domain. In a specific aspect, the (multi specific) antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1C and 1F (in these examples with the first antigen binding domain being a VH/VL crossover Fab molecule, and the second and the third antigen binding domain being a conventional Fab molecule) and in FIGS. 1I and 1M (in these examples with the first antigen binding domain being a conventional Fab molecule, and the second and the third antigen binding domain being a VH/VL crossover Fab molecule). The second and the third Fab molecule may be fused to the Fc domain directly or through a peptide linker. In a preferred aspect the second and the third Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In configurations of the (multispecific) antibody wherein a Fab molecule is fused at the C-terminus of the Fab heavy chain to the N-terminus of each of the subunits of the Fc domain through an immunoglobulin hinge region, the two Fab molecules, the hinge regions and the Fc domain essentially form an immunoglobulin molecule. In a preferred aspect the immunoglobulin molecule is an IgG class immunoglobulin. In an even more preferred aspect the immunoglobulin is an $IgG_1$ subclass immunoglobulin. In another aspect the immunoglobulin is an $IgG_4$ subclass immunoglobulin. In a further preferred aspect the immunoglobulin is a human immunoglobulin. In other aspects the immunoglobulin is a chimeric immunoglobulin or a humanized immunoglobulin. In one aspect, the immunoglobulin comprises a human constant region, particularly a human Fc region.

In some of the (multispecific) antibodies of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the (multispecific) antibody of the invention.

The antigen binding domains may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$, $G_4(SG_4)_n$ or $(G_4S)_nG_5$ peptide linkers. "n" is generally an integer from 1 to 10, typically from 2 to 4. In one aspect said peptide linker has a length of at least 5 amino acids, in one aspect a length of 5 to 100, in a further aspect of 10 to 50 amino acids. In one aspect said peptide linker is $(GxS)_n$ or $(GxS)_nG_m$ with G=glycine, S=serine, and (x=3, n=3, 4, 5 or 6, and m=0, 1, 2 or 3) or (x=4, n=1, 2, 3, 4 or 5 and m=0, 1, 2, 3, 4 or 5), in one aspect x=4 and n=2 or 3, in a further aspect x=4 and n=2, in yet a further aspect x=4, n=1 and m=5. In one aspect said peptide linker is $(G_4S)_2$. In another aspect, said peptide linker is $G_4SG_5$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 48 and 49). Another particularly suitable such linker comprises the sequence (D)-$G_4SG_5$ (SEQ ID NOs 50 and 51). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-$CH2$-$CH3$(-$CH4$)), and a polypeptide wherein the Fab heavy chain of the second Fab molecule shares a carboxy-terminal peptide bond with an Fc domain subunit ($VH_{(2)}$-$CH1_{(2)}$-$CH2$-$CH3$(-$CH4$)). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In certain aspects the polypeptides are covalently linked, e.g., by a disulfide bond.

In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-$CH2$-$CH3$(-$CH4$)), and a polypeptide wherein the Fab heavy chain of the second Fab molecule shares a carboxy-terminal peptide bond with an Fc domain subunit ($VH_{(2)}$-$CH1_{(2)}$-$CH2$-$CH3$(-$CH4$)). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In certain aspects the polypeptides are covalently linked, e.g., by a disulfide bond.

In some aspects, the (multispecific) antibody comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with an Fc domain subunit ($VL_{(1)}$-$CH1_{(1)}$-$VH_{(2)}$-$CH1_{(2)}$-$CH2$-$CH3$(-$CH4$)). In other aspects, the (multi specific) antibody comprises a polypeptide wherein the Fab heavy chain of the second Fab molecule shares a carboxy-terminal peptide bond with the Fab light chain variable region of the first Fab molecule which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with an Fc domain subunit ($VH_{(2)}$-$CH1_{(2)}$-$VL_{(1)}$-$CH1_{(1)}$-$CH2$-$CH3$(-$CH4$)). In some of these aspects the (multispecific) antibody further comprises a crossover Fab light chain polypeptide of the first Fab molecule, wherein the Fab heavy chain variable region of the first Fab molecule shares a carboxy-terminal peptide bond with the Fab light chain constant region of the first Fab molecule ($VH_{(1)}$-$CL_{(1)}$), and the Fab light chain polypeptide of the second Fab molecule ($VL_{(2)}$-$CL_{(2)}$). In others of these aspects the (multispecific) antibody further comprises a polypeptide wherein the Fab heavy chain variable region of the first Fab molecule shares a carboxy-terminal peptide bond with the Fab light chain constant region of the first Fab molecule which in turn shares a carboxy-terminal peptide bond with the Fab light chain polypeptide of the second Fab molecule ($VH_{(1)}$-$CL_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$), as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In some aspects, the (multispecific) antibody comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with an Fc domain subunit ($VH_{(1)}$-$CL_{(1)}$-$VH_{(2)}$-$CH1_{(2)}$-CH2-CH3(-CH4)). In other aspects, the (multi specific) antibody comprises a polypeptide wherein the Fab heavy chain of the second Fab molecule shares a carboxy-terminal peptide bond with the Fab heavy chain variable region of the first Fab molecule which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CH1_{(2)}$-$VH_{(1)}$-$CL_{(1)}$-CH2-CH3(-CH4)). In some of these aspects the (multispecific) antibody further comprises a crossover Fab light chain polypeptide of the first Fab molecule, wherein the Fab light chain variable region of the first Fab molecule shares a carboxy-terminal peptide bond with the Fab heavy chain constant region of the first Fab molecule ($VL_{(1)}$-$CH1_{(1)}$), and the Fab light chain polypeptide of the second Fab molecule ($VL_{(2)}$-$CL_{(2)}$). In others of these aspects the (multispecific) antibody further comprises a polypeptide wherein the Fab light chain variable region of the first Fab molecule shares a carboxy-terminal peptide bond with the Fab heavy chain constant region of the first Fab molecule which in turn shares a carboxy-terminal peptide bond with the Fab light chain polypeptide of the second Fab molecule ($VL_{(1)}$-$CH1_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$), as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In certain aspects, the (multispecific) antibody does not comprise an Fc domain. In preferred such aspects, said second and, if present, third antigen binding domains are each a conventional Fab molecule, and the first antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said second and, if present, third antigen binding domains are each a crossover Fab molecule and the first antigen binding domain is a conventional Fab molecule.

In one such aspect, the (multispecific) antibody essentially consists of the first and the second antigen binding domain, and optionally one or more peptide linkers, wherein the first and the second antigen binding domain are both Fab molecules and the second antigen binding domain is fused at the C-terminus of the Fab heavy chain to the N-terminus of the Fab heavy chain of the first antigen binding domain. Such a configuration is schematically depicted in FIGS. 1O and 1S (in these examples with the first antigen binding domain being a VH/VL crossover Fab molecule and the second antigen binding domain being a conventional Fab molecule).

In another such aspect, the (multispecific) antibody essentially consists of the first and the second antigen binding domain, and optionally one or more peptide linkers, wherein the first and the second antigen binding domain are both Fab molecules and the first antigen binding domain is fused at the C-terminus of the Fab heavy chain to the N-terminus of the Fab heavy chain of the second antigen binding domain. Such a configuration is schematically depicted in FIGS. 1P and 1T (in these examples with the first antigen binding domain being a VH/VL crossover Fab molecule and the second antigen binding domain being a conventional Fab molecule).

In some aspects, the second Fab molecule is fused at the C-terminus of the Fab heavy chain to the N-terminus of the Fab heavy chain of the first Fab molecule, and the (multispecific) antibody further comprises a third antigen binding domain, particularly a third Fab molecule, wherein said third Fab molecule is fused at the C-terminus of the Fab heavy chain to the N-terminus of the Fab heavy chain of the second Fab molecule. In certain such aspects, the (multispecific) antibody essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the C-terminus of the Fab heavy chain to the N-terminus of the Fab heavy chain of the second Fab molecule. Such a configuration is schematically depicted in FIGS. 1Q and 1U (in these examples with the first antigen binding domain being a VH/VL crossover Fab molecule and the second and the third antigen binding domain each being a conventional Fab molecule), or FIGS. 1X and 1Z (in these examples with the first antigen binding domain being a conventional Fab molecule and the second and the third antigen binding domain each being a VH/VL crossover Fab molecule).

In some aspects, the first Fab molecule is fused at the C-terminus of the Fab heavy chain to the N-terminus of the Fab heavy chain of the second Fab molecule, and the (multispecific) antibody further comprises a third antigen binding domain, particularly a third Fab molecule, wherein said third Fab molecule is fused at the N-terminus of the Fab heavy chain to the C-terminus of the Fab heavy chain of the second Fab molecule. In certain such aspects, the (multispecific) antibody essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the N-terminus of the Fab heavy chain to the C-terminus of the Fab heavy chain of the second Fab molecule. Such a configuration is schematically depicted in FIGS. 1R and 1V (in these examples with the first antigen binding domain being a VH/VL crossover Fab molecule and the second and the third antigen binding domain each being a conventional Fab molecule), or FIGS. 1W and 1Y (in these examples with the first antigen binding domain being a conventional Fab molecule and the second and the third antigen binding domain each being a VH/VL crossover Fab molecule).

In certain aspects the (multispecific) antibody according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region) ($VH_{(2)}$-$CH1_{(2)}$-$VL_{(1)}$-$CH1_{(1)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule ($VL_{(1)}$-$CH1_{(1)}$-$VH_{(2)}$-$CH1_{(2)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region) ($VH_{(2)}$-$CH1_{(2)}$-$VH_{(1)}$-$CL_{(1)}$. In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule ($VH_{(1)}$-$CL_{(1)}$-$VH_{(2)}$-$CH1_{(2)}$). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$).

In certain aspects the (multispecific) antibody according to the invention comprises a polypeptide wherein the Fab heavy chain of a third Fab molecule shares a carboxy-terminal peptide bond with the Fab heavy chain of the second Fab molecule, which in turn shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region) ($VH_{(3)}$-$CH1_{(3)}$-$VH_{(2)}$-$CH1_{(2)}$-$VL_{(1)}$-$CH1_{(1)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$). In certain aspects the (multispecific) antibody according to the invention comprises a polypeptide wherein the Fab heavy chain of a third Fab molecule shares a carboxy-terminal peptide bond with the Fab heavy chain of the second Fab molecule, which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region) ($VH_{(3)}$-$CH1_{(3)}$-$VH_{(2)}$-$CH1_{(2)}$-$VH_{(1)}$-$CL_{(1)}$). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$). In certain aspects the (multispecific) antibody according to the invention comprises a polypeptide wherein the Fab light chain variable region of the first Fab molecule shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with the Fab heavy chain of a third Fab molecule ($VL_{(1)}$-$CH1_{(1)}$-$VH_{(2)}$-$CH1_{(2)}$-$VH_{(3)}$-$CH1_{(3)}$). In some aspects the (multispecific) antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$). In certain aspects the (multispecific) antibody according to the invention comprises a polypeptide wherein the Fab heavy chain variable region of the first Fab molecule shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with the Fab heavy chain of a third Fab molecule ($VH_{(1)}$-$CL_{(1)}$-$VH_{(2)}$-$CH1_{(2)}$-$VH_{(3)}$-$CH1_{(3)}$). In some aspects the (multispecific) antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some aspects the (multispecific) antibody further comprises the Fab light chain polypeptide of a third Fab molecule ($VL_{(3)}$-$CL_{(3)}$). In certain aspects the (multispecific) antibody according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$-$VL_{(3)}$-$CH1_{(3)}$). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some aspects the (multispecific) antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain aspects the (multispecific) antibody according to the invention comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$-$VH_{(3)}$-$CL_{(3)}$). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some aspects the (multispecific) antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In certain aspects the (multispecific) antibody according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(3)}$-$CH1_{(3)}$-$VL_{(2)}$-$CH1_{(2)}$-$VH_{(1)}$-$CH1_{(1)}$). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some aspects the (multispecific) antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain aspects the (multispecific) antibody according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(3)}$-$CL_{(3)}$-$VH_{(2)}$-$CL_{(2)}$-$VH_{(1)}$-$CH1_{(1)}$). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some aspects the (multispecific) antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In one aspect, the invention provides a (multispecific) antibody comprising
- a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second antigen binding domain that binds to CD19, wherein the second antigen binding domain is a (conventional) Fab molecule;
- c) an Fc domain composed of a first and a second subunit; wherein
  - (i) the first antigen binding domain under a) is fused at the C-terminus of the Fab heavy chain to the N-terminus of the Fab heavy chain of the second antigen binding domain under b), and the second antigen binding domain under b) is fused at the C-terminus of the Fab heavy chain to the N-terminus of one of the subunits of the Fc domain under c), or
  - (ii) the second antigen binding domain under b) is fused at the C-terminus of the Fab heavy chain to the N-terminus of the Fab heavy chain of the first antigen binding domain under a), and the first antigen binding domain under a) is fused at the C-terminus of the Fab heavy chain to the N-terminus of one of the subunits of the Fc domain under c).

In a preferred aspect, the invention provides a (multispecific) antibody comprising
- a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second and a third antigen binding domain that bind to CD19, wherein the second and the third antigen binding domain are each a (conventional) Fab molecule; and
- c) an Fc domain composed of a first and a second subunit; wherein
  - (i) the first antigen binding domain under a) is fused at the C-terminus of the Fab heavy chain to the N-terminus of the Fab heavy chain of the second antigen binding domain under b), and the second antigen binding domain under b) and the third antigen binding domain under b) are each fused at the C-terminus of the Fab heavy chain to the N-terminus of one of the subunits of the Fc domain under c), or
  - (ii) the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In another aspect, the invention provides a (multispecific) antibody comprising
- a) a first antigen binding domain that binds to CD3, wherein the first antigen binding domain is a Fab molecule wherein the variable domains VL and VH or the constant domains CL and CH1 of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second antigen binding domain that binds to CD19, wherein the second antigen binding domain is a (conventional) Fab molecule;
- c) an Fc domain composed of a first and a second subunit; wherein
  - (i) the first antigen binding domain under a) and the second antigen binding domain under b) are each fused at the C-terminus of the Fab heavy chain to the N-terminus of one of the subunits of the Fc domain under c).

In all of the different configurations of the (multispecific) antibody according to the invention, the amino acid substitutions ("charge modifications") described herein, if present, may either be in the CH1 and CL domains of the second and (if present) the third antigen binding domain/Fab molecule, or in the CH1 and CL domains of the first antigen binding domain/Fab molecule. Preferably, they are in the CH1 and CL domains of the second and (if present) the third antigen binding domain/Fab molecule. In accordance with the concept of the invention, if amino acid substitutions as described herein are made in the second (and, if present, the third) antigen binding domain/Fab molecule, no such amino acid substitutions are made in the first antigen binding domain/Fab molecule. Conversely, if amino acid substitutions as described herein are made in the first antigen binding domain/Fab molecule, no such amino acid substitutions are made in the second (and, if present, the third) antigen binding domain/Fab molecule. Amino acid substitutions are preferably made in (multispecific) antibodies comprising a Fab molecule wherein the variable domains VL and VH1 of the Fab light chain and the Fab heavy chain are replaced by each other.

In preferred aspects of the (multispecific) antibody according to the invention, particularly wherein amino acid substitutions as described herein are made in the second (and, if present, the third) antigen binding domain/Fab molecule, the constant domain CL of the second (and, if present, the third) Fab molecule is of kappa isotype. In other aspects of the (multispecific) antibody according to the invention, particularly wherein amino acid substitutions as described herein are made in the first antigen binding domain/Fab molecule, the constant domain CL of the first antigen binding domain/Fab molecule is of kappa isotype. In some aspects, the constant domain CL of the second (and, if present, the third) antigen binding domain/Fab molecule and the constant domain CL of the first antigen binding domain/Fab molecule are of kappa isotype.

In one aspect, the invention provides a (multispecific) antibody comprising
- a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second antigen binding domain that binds to CD19, wherein the second antigen binding domain is a (conventional) Fab molecule;
- c) an Fc domain composed of a first and a second subunit;

wherein in the constant domain CL of the second antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein
- (i) the first antigen binding domain under a) is fused at the C-terminus of the Fab heavy chain to the N-terminus of the Fab heavy chain of the second antigen binding domain under b), and the second antigen binding domain under b) is fused at the C-terminus of the Fab heavy chain to the N-terminus of one of the subunits of the Fc domain under c), or
- (ii) the second antigen binding domain under b) is fused at the C-terminus of the Fab heavy chain to the N-terminus of the Fab heavy chain of the first antigen binding domain under a), and the first antigen binding domain under a) is fused at the C-terminus of the Fab heavy chain to the N-terminus of one of the subunits of the Fc domain under c).

In a preferred aspect, the invention provides a (multispecific) antibody comprising
- a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second and a third antigen binding domain that bind to CD19, wherein the second and third antigen binding domain are each a (conventional) Fab molecule; and
- c) an Fc domain composed of a first and a second subunit;

wherein in the constant domain CL of the second antigen binding domain under b) and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) and the third antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein
- (i) the first antigen binding domain under a) is fused at the C-terminus of the Fab heavy chain to the N-terminus of the Fab heavy chain of the second antigen binding domain under b), and the second antigen binding domain under b) and the third antigen binding domain under b) are each fused at the C-terminus of the Fab heavy chain to the N-terminus of one of the subunits of the Fc domain under c), or
- (ii) the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In another aspect, the invention provides a (multispecific) antibody comprising
- a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
- b) a second antigen binding domain that binds to CD19, wherein the second antigen binding domain is a (conventional) Fab molecule;
- c) an Fc domain composed of a first and a second subunit;

wherein in the constant domain CL of the second antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein the first antigen binding domain under a) and the second antigen binding domain under b) are each fused at the C-terminus of the Fab heavy chain to the N-terminus of one of the subunits of the Fc domain under c).

According to any of the above aspects, components of the (multispecific) antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$, $G_4(SG_4)_n$ or $(G_4S)_nG_5$ peptide linkers, wherein n is generally an integer from 1 to 10, typically from 2 to 4.

In a preferred aspect, the invention provides a (multispecific) antibody comprising
  a) a first antigen binding domain that binds CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
  b) a second and a third antigen binding domain that bind to CD19, wherein the second and the third antigen binding domain are each a (conventional) Fab molecule, and comprise a heavy chain variable region (VH) comprising a heavy chain complementary determining region (HCDR) 1 of SEQ ID NO: 15, a HCDR 2 of SEQ ID NO: 16, and a HCDR 3 of SEQ ID NO: 17, and a light chain variable region (VL) comprising a light chain complementarity determining region (LCDR) 1 of SEQ ID NO: 19, a LCDR 2 of SEQ ID NO: 20 and a LCDR 3 of SEQ ID NO: 21;
  c) an fc domain composed of a first and a second subunit; wherein
  in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein further
  the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a further preferred aspect, the invention provides a (multispecific) antibody comprising
  a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region comprising the amino acid sequence of SEQ ID NO: 7 and a light chain variable region comprising the amino acid sequence of SEQ ID NO: 11;
  b) a second and a third antigen binding domain that bind to CD19, wherein the second and the third antigen binding domain are each a (conventional) Fab molecule, and comprise a heavy chain variable region comprising the amino acid sequence of SEQ ID NO: 18 and a light chain variable region comprising the amino acid sequence of SEQ ID NO: 22;
  c) an Fc domain composed of a first and a second subunit; wherein
  in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index); and wherein further
  the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a further preferred aspect, the invention provides a (multispecific) antibody comprising
  a) a first antigen binding domain that binds CD3, wherein the first antigen binding domain is a Fab molecule wherein the variable domains VL and VH of the Fab light chain and the Fab heavy chain are replaced by each other, and comprises a heavy chain variable region (VH) comprising a heavy chain complementary determining region (HCDR) 1 of SEQ ID NO: 2, a HCDR 2 of SEQ ID NO: 3, and a HCDR 3 of SEQ ID NO: 5, and a light chain variable region (VL) comprising a light chain complementarity determining region (LCDR) 1 of SEQ ID NO: 8, a LCDR 2 of SEQ ID NO: 9 and a LCDR 3 of SEQ ID NO: 10;
  b) a second and a third antigen binding domain that bind to CD19, wherein the second and the third antigen binding domain are each a (conventional) Fab molecule, and comprise a heavy chain variable region (VH) comprising a heavy chain complementary determining region (HCDR) 1 of SEQ ID NO: 28, a HCDR 2 of SEQ ID NO: 29, and a HCDR 3 of SEQ ID NO: 30, and a light chain variable region (VL) comprising a light chain complementarity determining region (LCDR) 1 of SEQ ID NO: 32, a LCDR 2 of SEQ ID NO: 33 and a LCDR 3 of SEQ ID NO: 34;
  c) an Fc domain composed of a first and a second subunit; wherein
  in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In a yet further preferred aspect, the invention provides a (multispecific) antibody comprising a) a first antigen binding domain that binds to CD3, wherein the first antigen binding domain is a Fab molecule wherein the variable domains VL and VH of the Fab light chain and the Fab heavy chain are replaced by each other, and comprises a heavy chain variable region comprising the amino acid sequence of SEQ ID NO: 7 and a light chain variable region comprising the amino acid sequence of SEQ ID NO: 11;

b) a second and a third antigen binding domain that bind to CD19, wherein the second and the third antigen binding domain are each a (conventional) Fab molecule, and comprise a heavy chain variable region comprising the amino acid sequence of SEQ ID NO: 31 and a light chain variable region comprising the amino acid sequence of SEQ ID NO: 35;

c) an Fc domain composed of a first and a second subunit;

wherein in the constant domain CL of the second and the third antigen binding domain under b) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second and the third antigen binding domain under b) the amino acid at position 147 is substituted by glutamic acid (E) (numbering according to Kabat EU index) and the amino acid at position 213 is substituted by glutamic acid (E) (numbering according to Kabat EU index);

and wherein further the second antigen binding domain under b) is fused at the C-terminus of the Fab heavy chain to the N-terminus of the Fab heavy chain of the first antigen binding domain under a), and the first antigen binding domain under a) and the third antigen binding domain under b) are each fused at the C-terminus of the Fab heavy chain to the N-terminus of one of the subunits of the Fc domain under c).

In one aspect according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further aspect according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further aspect according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further aspect according to these aspects of the invention, the Fc domain is a human $IgG_1$ Fc domain.

In a preferred specific aspect, the (multispecific) antibody comprises a polypeptide comprising an amino acid sequence that is at least 95%, 96%, 97%, 98%, or 99% identical to the sequence of SEQ ID NO: 23 or SEQ ID NO: 39 (particularly SEQ ID NO: 39), a polypeptide comprising an amino acid sequence that is at least 95%, 96%, 97%, 98%, or 99% identical to the sequence of SEQ ID NO: 24, a polypeptide (particularly two polypeptides) comprising an amino acid sequence that is at least 95%, 96%, 97%, 98%, or 99% identical to the sequence of SEQ ID NO: 25, and a polypeptide comprising an amino acid sequence that is at least 95%, 96%, 97%, 98%, or 99% identical to the sequence of SEQ ID NO: 27. In a further preferred specific aspect, the (multispecific) antibody comprises a polypeptide comprising the amino acid sequence of SEQ ID NO: 23 or SEQ ID NO: 39 (particularly SEQ ID NO: 39), a polypeptide comprising the amino acid sequence of SEQ ID NO: 24, a polypeptide (particularly two polypeptides) comprising the amino acid sequence of SEQ ID NO: 25 and a polypeptide comprising the amino acid sequence of SEQ ID NO: 27.

In one aspect the invention provides a (multispecific) antibody that binds to CD3 and CD19, comprising a polypeptide comprising an amino acid sequence that is at least 95%, 96%, 97%, 98%, or 99% identical to the sequence of SEQ ID NO: 23 or SEQ ID NO: 39 (particularly SEQ ID NO: 39), a polypeptide comprising an amino acid sequence that is at least 95%, 96%, 97%, 98%, or 99% identical to the sequence of SEQ ID NO: 24, a polypeptide (particularly two polypeptides) comprising an amino acid sequence that is at least 95%, 96%, 97%, 98%, or 99% identical to the sequence of SEQ ID NO: 25, and a polypeptide comprising an amino acid sequence that is at least 95%, 96%, 97%, 98%, or 99% identical to the sequence of SEQ ID NO: 27. In one aspect the invention provides a (multispecific) antibody that binds to CD3 and CD19, comprising a polypeptide comprising the amino acid sequence of SEQ ID NO: 23 or SEQ ID NO: 39 (particularly SEQ ID NO: 39), a polypeptide comprising the amino acid sequence of SEQ ID NO: 24, a polypeptide (particularly two polypeptides) comprising the amino acid sequence of SEQ ID NO: 25 and a polypeptide comprising the amino acid sequence of SEQ ID NO: 27.

In a preferred specific aspect, the (multispecific) antibody comprises a polypeptide comprising an amino acid sequence that is at least 95%, 96%, 97%, 98%, or 99% identical to the sequence of SEQ ID NO: 36 or SEQ ID NO: 40 (particularly SEQ ID NO: 36), a polypeptide comprising an amino acid sequence that is at least 95%, 96%, 97%, 98%, or 99% identical to the sequence of SEQ ID NO: 37, a polypeptide (particularly two polypeptides) comprising an amino acid sequence that is at least 95%, 96%, 97%, 98%, or 99% identical to the sequence of SEQ ID NO: 38, and a polypeptide comprising an amino acid sequence that is at least 95%, 96%, 97%, 98%, or 99% identical to the sequence of SEQ ID NO: 27. In a further preferred specific aspect, the (multispecific) antibody comprises a polypeptide comprising the amino acid sequence of SEQ ID NO: 36 or SEQ ID NO: 40 (particularly SEQ ID NO: 36), a polypeptide comprising the amino acid sequence of SEQ ID NO: 37, a polypeptide (particularly two polypeptides) comprising the amino acid sequence of SEQ ID NO: 38 and a polypeptide comprising the amino acid sequence of SEQ ID NO: 27.

In one aspect the invention provides a (multispecific) antibody that binds to CD3 and CD19, comprising a polypeptide comprising an amino acid sequence that is at least 95%, 96%, 97%, 98%, or 99% identical to the sequence of SEQ ID NO: 36 or SEQ ID NO: 40 (particularly SEQ ID NO: 36), a polypeptide comprising an amino acid sequence that is at least 95%, 96%, 97%, 98%, or 99% identical to the sequence of SEQ ID NO: 37, a polypeptide (particularly two polypeptides) comprising an amino acid sequence that is at least 95%, 96%, 97%, 98%, or 99% identical to the sequence of SEQ ID NO: 38, and a polypeptide comprising an amino acid sequence that is at least 95%, 96%, 97%, 98%, or 99% identical to the sequence of SEQ ID NO: 27. In one aspect the invention provides a (multispecific) antibody that binds to CD3 and CD19, comprising a polypeptide comprising the amino acid sequence of SEQ ID NO: 36 or SEQ ID NO: 40 (particularly SEQ ID NO: 36), a polypeptide comprising the amino acid sequence of SEQ ID NO: 37, a polypeptide (particularly two polypeptides) comprising the amino acid sequence of SEQ ID NO: 38 and a polypeptide comprising the amino acid sequence of SEQ ID NO: 27.

8. Fc Domain Variants

In preferred aspects, the (multispecific) antibody of the invention comprises an Fc domain composed of a first and a second subunit.

The Fc domain of the (multispecific) antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one aspect, the (multispecific) antibody of the invention comprises not more than one Fc domain.

In one aspect, the Fc domain of the (multispecific) antibody is an IgG Fc domain. In a preferred aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further preferred aspect, the Fc domain is a human Fc domain. In an even more preferred aspect, the Fc domain is a human $IgG_1$ Fc domain. An exemplary sequence of a human $IgG_1$ Fc region is given in SEQ ID NO: 47.

a) Fc Domain Modifications Promoting Heterodimerization (Multispecific) antibodies according to the invention comprise different antigen binding domains, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of (multispecific) antibodies in recombinant production, it will thus be advantageous to introduce in the Fc domain of the (multispecific) antibody a modification promoting the association of the desired polypeptides.

Accordingly, in preferred aspects, the Fc domain of the (multispecific) antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the (multispecific) antibody which reduce heavy/light chain mispairing and Bence Jones-type side products.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a preferred aspect, in the CH3 domain of the first subunit of the Fc domain of the (multispecific) antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific aspect, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index). In a preferred aspect the antigen binding domain that binds to CD3 is fused (optionally via the second antigen binding domain, which binds to CD19, and/or a peptide linker) to the first subunit of the Fc domain (comprising the "knob" modification). Without wishing to be bound by theory, fusion of the antigen binding domain that binds CD3 to the knob-containing subunit of the Fc domain will (further) minimize the generation of antibodies comprising two antigen binding domains that bind to CD3 (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one aspect, the heterodimerization approach described in EP 1870459, is used alternatively. This approach is based on the introduction of charged amino acids with opposite charges at specific amino acid positions in the CH3/CH3 domain interface between the two subunits of the Fc domain. A particular aspect for the (multispecific) antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another aspect, the (multispecific) antibody of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another aspect, the (multispecific) antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said (multispecific) antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one aspect, the heterodimerization approach described in WO 2013/157953 is used alternatively. In one aspect, a first CH3 domain comprises amino acid mutation T366K and a second CH3 domain comprises amino acid mutation L351D (numberings according to Kabat EU index). In a further aspect, the first CH3 domain comprises further amino acid mutation L351K. In a further aspect, the second CH3 domain comprises further an amino acid mutation selected from Y349E, Y349D and L368E (particularly L368E) (numberings according to Kabat EU index). In one aspect, the heterodimerization approach described in WO 2012/058768 is used alternatively. In one aspect a first CH3 domain comprises amino acid mutations L351Y, Y407A and a second CH3 domain comprises amino acid mutations T366A, K409F. In a further aspect the second CH3 domain comprises a further amino acid mutation at position T411, D399, 5400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further aspect a first CH3 domain comprises amino acid mutations L351Y, Y407A and a second CH3 domain comprises amino acid mutations T366V, K409F. In a further aspect, a first CH3 domain comprises amino acid mutation Y407A and a second CH3 domain comprises amino acid mutations T366A, K409F. In a further aspect, the second CH3 domain further comprises amino acid mutations K392E, T411E, D399R and S400R (numberings according to Kabat EU index).

In one aspect, the heterodimerization approach described in WO 2011/143545 is used alternatively, e.g. with the amino acid modification at a position selected from the group consisting of 368 and 409 (numbering according to Kabat EU index).

In one aspect, the heterodimerization approach described in WO 2011/090762, which also uses the knobs-into-holes technology described above, is used alternatively. In one aspect a first CH3 domain comprises amino acid mutation T366W and a second CH3 domain comprises amino acid mutation Y407A. In one aspect, a first CH3 domain comprises amino acid mutation T366Y and a second CH3 domain comprises amino acid mutation Y407T (numberings according to Kabat EU index).

In one aspect, the (multispecific) antibody or its Fc domain is of IgG$_2$ subclass and the heterodimerization approach described in WO 2010/129304 is used alternatively.

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such aspect, a first CH3 domain comprises amino acid substitution of K392 or N392 with a negatively charged amino acid (e.g. glutamic acid (E), or aspartic acid (D), particularly K392D or N392D) and a second CH3 domain comprises amino acid substitution of D399, E356, D356, or E357 with a positively charged amino acid (e.g. lysine (K) or arginine (R), particularly D399K, E356K, D356K, or E357K, and more particularly D399K and E356K). In a further aspect, the first CH3 domain further comprises amino acid substitution of K409 or R409 with a negatively charged amino acid (e.g. glutamic acid (E), or aspartic acid (D), particularly K409D or R409D). In a further aspect the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further aspect, the heterodimerization approach described in WO 2007/147901 is used alternatively. In one aspect, a first CH3 domain comprises amino acid mutations K253E, D282K, and K322D and a second CH3 domain comprises amino acid mutations D239K, E240K, and K292D (numberings according to Kabat EU index).

In still another aspect, the heterodimerization approach described in WO 2007/110205 can be used alternatively.

In one aspect, the first subunit of the Fc domain comprises amino acid substitutions K392D and K409D, and the second subunit of the Fc domain comprises amino acid substitutions D356K and D399K (numbering according to Kabat EU index).

b) Fc Domain Modifications Reducing Fc Receptor Binding and/or Effector Function The Fc domain confers to the (multispecific) antibody favorable pharmacokinetic properties, including a long serum half-life which contributes to good accumulation in the target tissue and a favorable tissue-blood distribution ratio. At the same time it may, however, lead to undesirable targeting of the (multispecific) antibody to cells expressing Fc receptors rather than to the preferred antigen-bearing cells. Moreover, the co-activation of Fc receptor signaling pathways may lead to cytokine release which, in combination with the T cell activating properties and the long half-life of the (multispecific) antibody, results in excessive activation of cytokine receptors and severe side effects upon systemic administration. Activation of (Fc receptor-bearing) immune cells other than T cells may even reduce efficacy of the (multispecific) antibody due to the potential destruction of T cells e.g. by NK cells.

Accordingly, in preferred aspects, the Fc domain of the (multispecific) antibody according to the invention exhibits reduced binding affinity to an Fc receptor and/or reduced effector function, as compared to a native IgG$_1$ Fc domain. In one such aspect the Fc domain (or the (multispecific) antibody comprising said Fc domain) exhibits less than 50%, particularly less than 20%, more particularly less than 10% and most particularly less than 5% of the binding affinity to an Fc receptor, as compared to a native IgG$_1$ Fc domain (or a (multispecific) antibody comprising a native IgG$_1$ Fc domain), and/or less than 50%, particularly less than 20%, more particularly less than 10% and most particularly less than 5% of the effector function, as compared to a native IgG$_1$ Fc domain (or a (multispecific) antibody comprising a native IgG$_1$ Fc domain). In one aspect, the Fc domain (or the (multispecific) antibody comprising said Fc domain) does not substantially bind to an Fc receptor and/or induce effector function. In a preferred aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa. In one aspect the effector function is one or more selected from the group of CDC, ADCC, ADCP, and cytokine secretion. In a preferred aspect, the effector function is ADCC. In one aspect, the Fc domain exhibits substantially similar binding affinity to neonatal Fc receptor (FcRn), as compared to a native IgG$_1$ Fc domain. Substantially similar binding to FcRn is achieved when the Fc domain (or the (multispecific) antibody comprising said Fc domain) exhibits greater than about 70%, particularly greater than about 80%, more particularly greater than about 90% of the binding affinity of a native IgG$_1$ Fc domain (or the (multispecific) antibody comprising a native IgG$_1$ Fc domain) to FcRn.

In certain aspects the Fc domain is engineered to have reduced binding affinity to an Fc receptor and/or reduced effector function, as compared to a non-engineered Fc domain. In preferred aspects, the Fc domain of the (multispecific) antibody comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In one aspect, the amino acid mutation reduces the binding affinity of the Fc domain to an Fc receptor by at least 2-fold, at least 5-fold, or at least 10-fold. In aspects where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one aspect the (multispecific) antibody comprising an engineered Fc domain exhibits less than 20%, particularly less than 10%, more particularly less than 5% of the binding affinity to an Fc receptor as compared to a (multispecific) antibody comprising a non-engineered Fc domain. In a preferred aspect, the Fc receptor is an Fcγ receptor. In some aspects, the Fc receptor is a human Fc receptor. In some aspects, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the (multispecific) antibody comprising said Fc domain) exhibits greater than about 70% of the binding affinity of a non-engineered form of the Fc domain (or the (multispecific) antibody comprising said non-engineered form of the Fc domain) to FcRn. The Fc domain, or (multispecific) antibodies of the invention comprising said Fc domain, may exhibit greater than about 80% and even greater than about 90% of such affinity. In certain aspects, the Fc domain of the (multispecific) antibody is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one aspect, the reduced effector function is one or more selected from the group of reduced CDC, reduced ADCC, reduced ADCP, and reduced cytokine secretion. In a preferred aspect, the reduced effector function is reduced ADCC. In one aspect the reduced ADCC is less than 20% of the ADCC induced by a non-engineered Fc domain (or a (multispecific) antibody comprising a non-engineered Fc domain). In one aspect, the amino acid mutation that reduces the binding affinity of the Fc domain to an Fc receptor and/or effector function is an amino acid substitution. In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an IgG$_1$ Fc domain, particularly a human IgG$_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In preferred aspects, the Fc domain comprises amino acid substitutions at positions P329, L234 and L235 (numberings according to Kabat EU index). In more preferred aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such aspect, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some aspects, the Fc domain of the (multispecific) antibodies of the invention is an IgG$_4$ Fc domain, particularly a human IgG$_4$ Fc domain. In one aspect, the IgG$_4$ Fc domain comprises an amino acid substitution at position S228, specifically the amino acid substitution S228P (numberings according to Kabat EU index). To further reduce its binding affinity to an Fc receptor and/or its effector function, in one aspect, the IgG$_4$ Fc domain comprises an amino acid substitution at position L235, specifically the amino acid substitution L235E (numberings according to Kabat EU index). In another aspect, the IgG$_4$ Fc domain comprises an amino acid substitution at position P329, specifically the amino acid substitution P329G (numberings according to Kabat EU index). In a preferred aspect, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a preferred aspect, the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain aspects, N-glycosylation of the Fc domain has been eliminated. In one such aspect, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or (multispecific) antibodies comprising an Fc domain for Fc receptors may be evaluated using cell lines known to express particular Fc receptors, such as human NK cells expressing FcγIIIa receptor.

Effector function of an Fc domain, or a (multispecific) antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays may be employed (see, for example, ACTI™ non-radioactive cytotoxicity assay for flow cytometry (CellTechnology, Inc. Mountain View, CA); and CytoTox 96 ® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the Fc domain, or the (multispecific) antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)). FcRn binding and in vivo clearance/half life determinations can also be performed using methods known in the art (see, e.g., Petkova, S. B. et al., *Int'l. Immunol.* 18(12):1759-1769 (2006); WO 2013/120929).

B. Polynucleotides

The invention further provides an isolated polynucleotide encoding an antibody of the invention. Said isolated polynucleotide may be a single polynucleotide or a plurality of polynucleotides. The polynucleotides encoding (multispecific) antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the portion of the antibody comprising the heavy chain of the antibody. When co-expressed, the heavy chain polypeptides will associate with the light chain polypeptides to form the antibody. In another example, the portion of the antibody comprising one of the two Fc domain subunits and optionally (part of) one or more Fab molecules could be encoded by a separate polynucleotide from the portion of the antibody comprising the other of the two Fc domain subunits and optionally (part of) a Fab molecule. When co-expressed, the Fc domain subunits will associate to form the Fc domain.

In some aspects, the isolated polynucleotide encodes the entire antibody molecule according to the invention as described herein. In other aspects, the isolated polynucleotide encodes a polypeptide comprised in the antibody according to the invention as described herein.

In certain aspects the polynucleotide or nucleic acid is DNA. In other aspects, a polynucleotide of the present invention is RNA, for example, in the form of messenger RNA (mRNA). RNA of the present invention may be single stranded or double stranded.

C. Recombinant Methods

Antibodies of the invention may be obtained, for example, by solid-state peptide synthesis (e.g. Merrifield solid phase synthesis) or recombinant production. For recombinant production one or more polynucleotide encoding the antibody, e.g., as described above, is isolated and inserted into one or more vectors for further cloning and/or expression in a host cell. Such polynucleotide may be readily isolated and sequenced using conventional procedures. In one aspect a vector, particularly an expression vector, comprising the polynucleotide (i.a. a single polynucleotide or a plurality of polynucleotides) of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible by tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain aspects, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further aspect, a host cell comprising a polynucleotide (i.e. a single polynucleotide or a plurality of polynucleotides) of the invention is provided. In certain aspects a host cell comprising a vector of the invention is provided. The polynucleotides and vectors may incorporate any of the features, singly or in combination, described herein in relation to polynucleotides and vectors, respectively. In one such aspect a host cell comprises (e.g. has been transformed or transfected with) one or more vector comprising one or more polynucleotide that encodes (part of) an antibody of the invention. As used herein, the term "host cell" refers to any kind of cellular system which can be engineered to generate the antibody of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and F S4 cells. Other useful mammalian host cell lines include Chinese hamster ovary (CHO) cells, including dhfr$^-$ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one aspect, the host cell is a eukaryotic cell, particularly a mammalian cell, such as a Chinese Hamster Ovary (CHO) cell, a human embryonic kidney (HEK) cell or a lymphoid cell (e.g., YO, NS0, Sp20 cell). In one aspect, the host cell is not a cell within a human body. Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one aspect, a method of producing an antibody according to the invention is provided, wherein the method comprises culturing a host cell comprising a polynucleotide encoding the antibody, as provided herein, under conditions suitable for expression of the antibody, and optionally recovering the antibody from the host cell (or host cell culture medium).

The components of the (multispecific) antibody of the invention may be genetically fused to each other. The (multispecific) antibody can be designed such that its components are fused directly to each other or indirectly through a linker sequence. The composition and length of the linker may be determined in accordance with methods well known in the art and may be tested for efficacy. Examples of linker sequences between different components of (multispecific) antibodies are provided herein. Additional sequences may also be included to incorporate a cleavage site to separate the individual components of the fusion if desired, for example an endopeptidase recognition sequence.

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well-known analytical methods including gel electrophoresis, high pressure liquid chromatography, and the like.

D. Assays

Antibodies provided herein may be identified, screened for, or characterized for their physical/chemical properties and/or biological activities by various assays known in the art.

1. Binding Assays

The binding (affinity) of the antibody to an Fc receptor or a target antigen can be determined for example by surface plasmon resonance (SPR), using standard instrumentation such as a BIAcore instrument (GE Healthcare), and receptors or target proteins such as may be obtained by recombinant expression. Alternatively, binding of antibodies to different receptors or target antigens may be evaluated using cell lines expressing the particular receptor or target antigen, for example by flow cytometry (FACS). A specific illustrative and exemplary aspect for measuring binding activity to CD3 is described in the following.

In one aspect, the binding activity to CD3 is determined by SPR as follows:

SPR is performed on a Biacore T200 instrument (GE Healthcare). Anti-Fab capturing antibody (GE Healthcare, #28958325) is immobilized on a Series S Sensor Chip CM5 (GE Healthcare) using standard amine coupling chemistry, at a surface density of 4000-6000 resonance units (RU). As running and dilution buffer, EIBS-P+ (10 mM HEPES, 150 mM NaCl pH 7.4, 0.05% Surfactant P20) is used. CD3 antibodies with a concentration of 2 µg/ml (in 20 mM His, 140 mM NaCl, pH 6.0) are injected for about 60 s at a flow rate of 511.1/min. The CD3 antigen used is a heterodimer of CD3 delta and CD3 epsilon ectodomains fused to a human Fc domain with knob-into-hole modifications and a C-terminal Avi-tag (see SEQ ID NOs 41 and 42). CD3 antigen is injected at a concentration of 10 µg/ml for 120 s and dissociation is monitored at a flow rate of 5 µl/min for about 120 s. The chip surface is regenerated by two consecutive injections of 10 mM glycine pH 2.1 for about 60 s each. Bulk refractive index differences are corrected by subtracting blank injections and by subtracting the response obtained from the blank control flow cell. For evaluation, the binding response is taken 5 seconds after injection end. To normalize the binding signal, the CD3 binding is divided by the anti-Fab response (the signal (RU) obtained upon capture of the CD3 antibody on the immobilized anti-Fab antibody). The binding activity to CD3 of an antibody after a certain treatment, relative to the binding activity to CD3 of the antibody after a different treatment (also referred to as relative active concentration (RAC)) is calculated by referencing the binding activity of a sample of the antibody after the certain treatment to the binding activity of a corresponding sample of the antibody after the different treatment.

2. Activity Assays

Biological activity of the (multispecific) antibodies of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as B-cells, and the induction of tumor regression and/or the improvement of survival.

E. Compositions, Formulations, and Routes of Administration

In a further aspect, the invention provides pharmaceutical compositions comprising any of the antibodies provided herein, e.g., for use in any of the below therapeutic methods. In one aspect, a pharmaceutical composition comprises an antibody according to the invention and a pharmaceutically acceptable carrier. In another aspect, a pharmaceutical composition comprises an antibody according to the invention and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise an effective amount of antibody dissolved or dispersed in a pharmaceutically acceptable carrier. The phrase "pharmaceutically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, particularly in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular aspects, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

F. Therapeutic Methods and Compositions

Any of the antibodies provided herein may be used in therapeutic methods. Antibodies of the invention may be used as immunotherapeutic agents, for example in the treatment of cancers or autoimmune diseases.

For use in therapeutic methods, antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies of the invention for use as a medicament are provided. In further aspects, antibodies of the invention for use in treating a disease are provided. In certain aspects, antibodies of the invention for use in a method of treatment are provided. In one aspect, the invention provides an antibody of the invention for use in the treatment of a disease in an individual in need thereof. In certain aspects, the invention provides an antibody for use in a method of treating an individual having a disease comprising administering to the individual an effective amount of the antibody. In certain aspects the disease is a proliferative disorder. In certain aspects the disease is cancer, particularly a CD19-expressing cancer. In a specific aspect the cancer is a B-cell cancer. The B-cell cancer in one aspect is a B-cell lymphoma or a B-cell leukemia. In one aspect the B-cell cancer is non-Hodgkin lymphoma or acute lymphoblastic leukemia or chronic lymphocytic leukemia. In other aspects the disease is an autoimmune disease. In a specific aspect the disease is lupus, in particular systemic lupus erythematosus (SLE) or lupus nephritis (LN).

In certain aspects the method further comprises administering to the individual an effective amount of at least one additional therapeutic agent, e.g., an anti-cancer agent if the disease to be treated is cancer or an immunosuppressive agent if the disease to be treated is an autoimmune disease. In further aspects, the invention provides an antibody of the invention for use in inducing lysis of a target cell, particularly a B-cell. In certain aspects, the invention provides an antibody of the invention for use in a method of inducing lysis of a target cell, particularly a B-cell, in an individual comprising administering to the individual an effective amount of the antibody to induce lysis of a target cell. An "individual" according to any of the above aspects is a mammal, preferably a human.

In a further aspect, the invention provides for the use of an antibody of the invention in the manufacture or preparation of a medicament. In one aspect the medicament is for the treatment of a disease in an individual in need thereof. In a further aspect, the medicament is for use in a method of treating a disease comprising administering to an individual having the disease an effective amount of the medicament. In certain aspects the disease is a proliferative disorder. In certain aspects the disease is cancer, particularly a CD19-expressing cancer. In a specific aspect the cancer is a B-cell cancer. The B-cell cancer in one aspect is a B-cell lymphoma or a B-cell leukemia. In one aspect the B-cell cancer is non-Hodgkin lymphoma or acute lymphoblastic leukemia or chronic lymphocytic leukemia. In other aspects the disease is an autoimmune disease. In a specific aspect the disease is lupus, in particular systemic lupus erythematosus (SLE) or lupus nephritis (LN). In one aspect, the method further comprises administering to the individual an effective amount of at least one additional therapeutic agent, e.g., an anti-cancer agent if the disease to be treated is cancer or an immunosuppressive agent if the disease to be treated is an autoimmune disease. In a further aspect, the medicament is for inducing lysis of a target cell, particularly a B-cell. In still a further aspect, the medicament is for use in a method of inducing lysis of a target cell, particularly a B-cell, in an individual comprising administering to the individual an effective amount of the medicament to induce lysis of a target cell. An "individual" according to any of the above aspects may be a mammal, preferably a human.

In a further aspect, the invention provides a method for treating a disease. In one aspect, the method comprises administering to an individual having such disease an effective amount of an antibody of the invention. In one aspect a composition is administered to said individual, comprising the antibody of the invention in a pharmaceutically acceptable form. In certain aspects the disease is a proliferative disorder. In certain aspects the disease is cancer, particularly a CD19-expressing cancer. In a specific aspect the cancer is a B-cell cancer. The B-cell cancer in one aspect is a B-cell lymphoma or a B-cell leukemia. In one aspect the B-cell cancer is non-Hodgkin lymphoma or acute lymphoblastic leukemia or chronic lymphocytic leukemia. In other aspects the disease is an autoimmune disease. In a specific aspect the disease is lupus, in particular systemic lupus erythematosus (SLE) or lupus nephritis (LN). In certain aspects the method further comprises administering to the individual an effective amount of at least one additional therapeutic agent, e.g., an anti-cancer agent if the disease to be treated is cancer or an immunosuppressive agent if the the disease to be treated is an autoimmune disease. An "individual" according to any of the above aspects may be a mammal, preferably a human.

In a further aspect, the invention provides a method for inducing lysis of a target cell, particularly a CD19-expressing cell such as a B-cell. In one aspect the method comprises contacting a target cell with an antibody of the invention in the presence of a T cell, particularly a cytotoxic T cell. In a further aspect, a method for inducing lysis of a target cell, particularly a CD19-expressing cell such as a B-cell, in an individual is provided. In one such aspect, the method comprises administering to the individual an effective amount of an antibody of the invention to induce lysis of a target cell. In one aspect, an "individual" is a human.

A skilled artisan readily recognizes that in many cases the antibody may not provide a cure but may only provide partial benefit. In some aspects, a physiological change having some benefit is also considered therapeutically beneficial. Thus, in some aspects, an amount of antibody that provides a physiological change is considered an "effective amount". The subject, patient, or individual in need of treatment is typically a mammal, more specifically a human.

In some aspects, an effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various timepoints, bolus administration, and pulse infusion are contemplated herein. The antibody is suitably administered to the patient at one time or over a series of treatments.

Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in an effective amount. For systemic administration, an effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective dose of the antibodies of the invention will generally provide therapeutic benefit without causing substantial toxicity. Toxicity and therapeutic efficacy of an antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one aspect, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular disease being treated, preferably those with complementary activities that do not adversely affect each other. In certain aspects, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In certain aspects, the additional therapeutic agent is an anticancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In other aspects, the additional therapeutic agent is an immunosuppressive agent. In a specific aspect, the additional therapeutic agent is one or more selected from the group of corticosteroids, hydroxychloroquine, mycophenolate mofetil, mycophenolic acid, methotrexate, azathioprine, cyclophosphamide, calcineurin inhibitors, belimumab, rituximab and obinutuzumab.

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody of the invention can occur prior to, simultaneously, and/or following, administration of the additional therapeutic agent and/or adjuvant. Antibodies of the invention may also be used in combination with radiation therapy.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

H. Methods and Compositions for Diagnostics and Detection

In certain aspects, any of the antibodies provided herein is useful for detecting the presence of its target (e.g. CD3 or CD19) in a biological sample. The term "detecting" as used herein encompasses quantitative or qualitative detection. In certain aspects, a biological sample comprises a cell or tissue, such as prostate tissue.

In one aspect, an antibody according to the invention for use in a method of diagnosis or detection is provided. In a further aspect, a method of detecting the presence of CD3 or CD19 in a biological sample is provided. In certain aspects, the method comprises contacting the biological sample with an antibody of the present invention under conditions permissive for binding of the antibody to CD3 or CD19, and detecting whether a complex is formed between the antibody and CD3 or CD19. Such method may be an in vitro or in vivo method. In one aspect, an antibody of the invention is used to select subjects eligible for therapy with an antibody that binds CD3 and/or CD19, e.g. where CD3 and/or CD19 is a biomarker for selection of patients.

Exemplary disorders that may be diagnosed using an antibody of the invention include cancer, particularly B-cell cancer.

In certain aspects, an antibody according to the present invention is provided, wherein the antibody is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

| | Amino Acid Sequence | SEQ ID NO |
|---|---|---|
| CD3$_{orig}$ HCDR1 | TYAMN | 1 |
| CD3$_{opt}$ HCDR1 | SYAMN | 2 |
| CD3$_{orig}$/CD3$_{opt}$ HCDR2 | RIRSKYNNYATYYADSVKG | 3 |
| CD3$_{orig}$ HCDR3 | HGNFGNSYVSWFAY | 4 |
| CD3$_{opt}$ HCDR3 | HTTFPSSYVSYYGY | 5 |
| CD3$_{orig}$ VH | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSS | 6 |
| CD3$_{opt}$ VH | EVQLLESGGGLVQPGGSLRLSCAASGFQFSSYAMNWVRQAPGKGLEWVSRIRSKYNNYATYYADSVKGRFTISRDDSKNTLYLQMNSLRAEDTAVYYCVRHTTFPSSYVSYYGYVVGQGTLVTVSS | 7 |
| CD3$_{orig}$/CD3$_{opt}$ LCDR1 | GSSTGAVTTSNYAN | 8 |
| CD3$_{orig}$/CD3$_{opt}$ LCDR2 | GTNKRAP | 9 |
| CD3$_{orig}$/CD3$_{opt}$ LCDR3 | ALWYSNLWV | 10 |
| CD3$_{orig}$/CD3$_{opt}$ VL | QAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVL | 11 |
| CD3$_{orig}$ IgG HC | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSP | 12 |
| CD3$_{opt}$ IgG HC | EVQLLESGGGLVQPGGSLRLSCAASGFQFSSYAMNWVRQAPGKGLEWVSRIRSKYNNYATYYADSVKGRFTISRDDSKNTLYLQMNSLRAEDTAVYYCVRHTTFPSSYVSYYGYVVGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSP | 13 |
| CD3$_{orig}$/CD3$_{opt}$ IgG LC | QAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVLRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 14 |

-continued

| | Amino Acid Sequence | SEQ ID NO |
|---|---|---|
| CD19(2B11) HCDR1 | DYIMH | 15 |
| CD19(2B11) HCDR2 | YINPYNDGSKYTEKFQG | 16 |
| CD19(2B11) HCDR3 | GTYYYGPQLFDY | 17 |
| CD19(2B11) VH | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGPQLFDYWGQGTTVT VSS | 18 |
| CD19(2B11) LCDR1 | KSSQSLETSTGTTYLN | 19 |
| CD19(2B11) LCDR2 | RVSKRFS | 20 |
| CD19(2B11) LCDR3 | LQLLEDPYT | 21 |
| CD19(2B11) VL | DIVMTQTPLSLSVTPGQPASISCKSSQSLETSTGTTYLNWYL QKPGQSPQLLIYRVSKRFSGVPDRFSGSGSGTDFTLKISRVE AEDVGVYYCLQLLEDPYTFGQGTKLEIK | 22 |
| CD19(2B11) VH-CH1(EE) - CD3$_{orig}$/CD3$_{opt}$ VL-CH1 - Fc (knob, PGLALA) | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGPQLFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDGGGGSGGGGQAVVT QEPSLTVSPGGTVTLTCGSSTGAVTTSNYANWVQEKPGQA FRGLIGGTNKRAPGTPARFSGSLLGGKAALTLSGAQPEDEA EYYCALWYSNLWVFGGGTKLTVLSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVDK KVEPKSCDKTHTCPPCPAPEAAGGPSVFLFPPKPKDTLMISR TPEVTCVVVDVSHEDPEVKFNWYVDGVEVHNAKTKPREE QYNSTYRVVSVLTVLHQDWLNGKEYKCKVSNKALGAPIE KTISKAKGQPREPQVYTLPPCRDELTKNQVSLWCLVKGFY PSDIAVEWESNGQPENNYKTTPPVLDSDGSFFLYSKLTVDK SRWQQGNVFSCSVMHEALHNHYTQKSLSLSP | 23 |
| CD19(2B11) VH-CH1(EE) - Fc (hole, PGLALA) | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGPQLFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDKTHTCPPCPAPEAAGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALGAPIEKTISKAKGQPREPQVCTLPPSRDELT KNQVSLSCAVKGFYPSDIAVEWESNGQPENNYKTTPPVLD SDGSFFLVSKLTVDKSRWQQGNVFSCSVMHEALHNHYTQ KSLSLSP | 24 |
| CD19(2B11) VL-CL(RK) | DIVMTQTPLSLSVTPGQPASISCKSSQSLETSTGTTYLNWYL QKPGQSPQLLIYRVSKRFSGVPDRFSGSGSGTDFTLKISRVE AEDVGVYYCLQLLEDPYTFGQGTKLEIKRTVAAPSVFIFPPS DRKLKSGTASVVCLLNNFYPREAKVQWKVDNALQSGNSQ ESVTEQDSKDSTYSLSSTLTLSKADYEKHKVYACEVTHQG LSSPVTKSFNRGEC | 25 |
| CD3$_{orig}$ VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 26 |
| CD3$_{opt}$ VH-CL | EVQLLESGGGLVQPGGSLRLSCAASGFQFSSYAMNWVRQA PGKGLEWVSRIRSKYNNYATYYADSVKGRFTISRDDSKNT LYLQMNSLRAEDTAVYYCVRHTTFPSSYVSYYGYVVGQGT | 27 |

-continued

| | Amino Acid Sequence | SEQ ID NO |
|---|---|---|
| | LVTVSSASVAAPSVFIFPPSDEQLKSGTASVVCLLNNFYPRE AKVQWKVDNALQSGNSQESVTEQDSKDSTYSLSSTLTLSK ADYEKHKVYACEVTHQGLSSPVTKSFNRGEC | |
| CD19(018) HCDR1 | DYIMH | 28 |
| CD19(018) HCDR2 | YINPYNDGSKYTEKFQG | 29 |
| CD19(018) HCDR3 | GTYYYGSALFDY | 30 |
| CD19(018) VH | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGSALFDYWGQGTTVT VSS | 31 |
| CD19(018) LCDR1 | KSSQSLENPNGNTYLN | 32 |
| CD19(018) LCDR2 | RVSKRFS | 33 |
| CD19(018) LCDR3 | LQLTHVPYT | 34 |
| CD19(018) VL | DIVMTQTPLSLSVTPGQPASISCKSSQSLENPNGNTYLNWY LQKPGQSPQLLIYRVSKRFSGVPDRFSGSGSGTDFTLKISRV EAEDVGVYYCLQLTHVPYTFGQGTKLEIK | 35 |
| CD19(018) VH-CH1(EE) - CD3$_{orig}$/CD3$_{opt}$ VL-CH1 - Fc (knob, PGLALA) | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGSALFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDGGGGSGGGGQAVVT QEPSLTVSPGGTVTLTCGSSTGAVTTSNYANWVQEKPGQA FRGLIGGTNKRAPGTPARFSGSLLGGKAALTLSGAQPEDEA EYYCALWYSNLWVFGGGTKLTVLSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVDK KVEPKSCDKTHTCPPCPAPEAAGGPSVFLFPPKPKDTLMISR TPEVTCVVVDVSHEDPEVKFNWYVDGVEVHNAKTKPREE QYNSTYRVVSVLTVLHQDWLNGKEYKCKVSNKALGAPIE KTISKAKGQPREPQVYTLPPCRDELTKNQVSLWCLVKGFY PSDIAVEWESNGQPENNYKTTPPVLDSDGSFFLYSKLTVDK SRWQQGNVFSCSVMHEALHNHYTQKSLSLSP | 36 |
| CD19(018) VH-CH1(EE) - Fc (hole, PGLALA) | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGSALFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDKTHTCPPCPAPEAAGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALGAPIEKTISKAKGQPREPQVCTLPPSRDELT KNQVSLSCAVKGFYPSDIAVEWESNGQPENNYKTTPPVLD SDGSFFLVSKLTVDKSRWQQGNVFSCSVMHEALHNHYTQ KSLSLSP | 37 |
| CD19(018) VL-CL(RK) | DIVMTQTPLSLSVTPGQPASISCKSSQSLENPNGNTYLNWY LQKPGQSPQLLIYRVSKRFSGVPDRFSGSGSGTDFTLKISRV EAEDVGVYYCLQLTHVPYTFGQGTKLEIKRTVAAPSVFIFP PSDRKLKSGTASVVCLLNNFYPREAKVQWKVDNALQSGN SQESVTEQDSKDSTYSLSSTLTLSKADYEKHKVYACEVTH QGLSSPVTKSFNRGEC | 38 |
| CD19(2B11) VH-CH1(EE) - CD3$_{orig}$/CD3$_{opt}$ VL-CH1 - Fc (knob, PGLALA) | QVQLVQSGAEVKKPGASVKVSCKASGYTFTDYIMHWVRQ APGQGLEWMGYINPYNDGSKYTEKFQGRVTMTDTSISTA YMELSRLRSDDTAVYYCARGTYYYGPQLFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDGGGGSGGGGSQAVVT | 39 |

| Amino Acid Sequence | SEQ ID NO |
|---|---|
| QEPSLTVSPGGTVTLTCGSSTGAVTTSNYANWVQEKPGQA FRGLIGGTNKRAPGTPARFSGSLLGGKAALTLSGAQPEDEA EYYCALWYSNLWVFGGGTKLTVLSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVDK KVEPKSCDKTHTCPPCPAPEAAGGPSVFLFPPKPKDTLMISR TPEVTCVVVDVSHEDPEVKFNWYVDGVEVHNAKTKPREE QYNSTYRVVSVLTVLHQDWLNGKEYKCKVSNKALGAPIE KTISKAKGQPREPQVYTLPPCRDELTKNQVSLWCLVKGFY PSDIAVEWESNGQPENNYKTTPPVLDSDGSFFLYSKLTVDK SRWQQGNVFSCSVMHEALHNHYTQKSLSLSP | |
| CD19(018) VH-CH1(EE) - CD3$_{orig}$/CD3$_{opt}$ VL-CH1 - Fc (knob, PGLALA) | QVQLVQSGAEVKKPGASVKVSCKASGYTFTDYIMHWVRQ APGQGLEWMGYINPYNDGSKYTEKFQGRVTMTSDTSISTA YMELSRLRSDDTAVYYCARGTYYYGSALFDYWGQGTTVT VSSASTKGPSVFPLAPSSKSTSGGTAALGCLVEDYFPEPVTV SWNSGALTSGVHTFPAVLQSSGLYSLSSVVTVPSSSLGTQT YICNVNHKPSNTKVDEKVEPKSCDGGGGSGGGGSQAVVT QEPSLTVSPGGTVTLTCGSSTGAVTTSNYANWVQEKPGQA FRGLIGGTNKRAPGTPARFSGSLLGGKAALTLSGAQPEDEA EYYCALWYSNLWVFGGGTKLTVLSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVDK KVEPKSCDKTHTCPPCPAPEAAGGPSVFLFPPKPKDTLMISR TPEVTCVVVDVSHEDPEVKFNWYVDGVEVHNAKTKPREE QYNSTYRVVSVLTVLHQDWLNGKEYKCKVSNKALGAPIE KTISKAKGQPREPQVYTLPPCRDELTKNQVSLWCLVKGFY PSDIAVEWESNGQPENNYKTTPPVLDSDGSFFLYSKLTVDK SRWQQGNVFSCSVMHEALHNHYTQKSLSLSP | 40 |
| Human CD3 epsilon stalk - Fc(knob) - Avi | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVSENCVDEQLYFQGGSPKSADKTHTC PPCPAPELLGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREPQ VYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPGKSGGLNDIFEAQKIEWHE | 41 |
| Human CD3 delta stalk - Fc (hole) - Avi | FKIPIEELEDRVFVNCNTSITWVEGTVGTLLSDITRLDLGKRI LDPRGIYRCNGTDIYKDKESTVQVHYRMCRSEQLYFQGDK THTCPPCPAPELLGGPSVFLFPPKPKDTLMISRTPEVTCVVV DVSHEDPEVKFNVVYVDGVEVHNAKTKPREEQYNSTYRVV SVLTVLHQDWLNGKEYKCKVSNKALPAPIEKTISKAKGQP REPQVCTLPPSRDELTKNQVSLSCAVKGFYPSDIAVEWESN GQPENNYKTTPPVLDSDGSFFLVSKLTVDKSRWQQGNVFS CSVMHEALHNHYTQKSLSLSPGKSGGLNDIFEAQKIEWHE | 42 |
| CD19 ECD - Fc (knob) - Avi | PEEPLVVKVEEGDNAVLQCLKGTSDGPTQQLTWSRESPLK PFLKLSLGLPGLGIHMRPLAIWLFIFNVSQQMGGFYLCQPG PPSEKAWQPGWTVNVEGSGELFRWNVSDLGGLGCGLKNR SSEGPSSPSGKLMSPKLYVWAKDRPEIWEGEPPCLPPRDSL NQSLSQDLTMAPGSTLWLSCGVPPDSVSRGPLSWTHVHPK GPKSLLSLELKDDRPARDMWVMETGLLLPRATAQDAGKY YCHRGNLTMSFHLEITARPVLWHWLLRTGGWKVDASGGS PTPPTPGGGSADKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVYTLPPCRDELTKNQVSLWCLVK GFYPSDIAVEWESNGQPENNYKTTPPVLDSDGSFFLYSKLT VDKSRWQQGNVFSCSVMHEALHNHYTQKSLSLSPGKSGG LNDIFEAQKIEWHE | 43 |
| Fc (hole) | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVCTLPPSRDELTKNQVSLSCAVKGFYPSDIAVEWE SNGQPENNYKTTPPVLDSDGSFFLVSKLTVDKSRWQQGNV FSCSVMHEALHNRFTQKSLSLSP | 44 |
| Human CD3 | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGG | 45 |

| Description | Amino Acid Sequence | SEQ ID NO |
|---|---|---|
| | LLLLVYYVVSKNRKAKAKPVTRGAGAGGRQRGQNKERPPP VPNPDYEPIRKGQRDLYSGLNQRRI | |
| Cynomolgus CD3 | QDGNEEMGSITQTPYQVSISGTTVILTCSQHLGSEAQWQHN GKNKEDSGDRLFLPEFSEMEQSGYYVCYPRGSNPEDASHH LYLKARVCENCMEMDVMAVATIVIVDICITLGLLLLVYYW SKNRKAKAKPVTRGAGAGGRQRGQNKERPPPVPNPDYEPI RKGQQDLYSGLNQRRI | 46 |
| hIgG$_1$ Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 47 |
| linker | GGGGSGGGGS | 48 |
| linker | DGGGGSGGGGS | 49 |
| linker | GGGGSGGGGG | 50 |
| linker | DGGGGSGGGGG | 51 |
| Human kappa CL domain | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 52 |
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 53 |
| Human IgG$_1$ heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 54 |

III. Sequences

IV. Examples

The following are examples of methods and compositions of the invention. It is understood that various other aspects may be practiced, given the general description provided above.

Example 1—Generation of Optimized CD3 Binder

Starting from a previously described (see e.g. WO 2014/131712, incorporated herein by reference) CD3 binder, termed "CD3$_{orig}$" herein and comprising the VH and VL sequences of SEQ ID NOs 6 and 11, respectively, we aimed at optimizing properties of this binder by removal of two asparagine deamidation sequence motifs at Kabat positions 97 and 100 of the heavy chain CDR3.

To this aim, we generated an antibody library, suitable for phage display, of the heavy chain with both asparagines at Kabat position 97 and 100 removed, and in addition the CDRs H1, H2, and H3 randomized in order to compensate for loss of affinity caused by replacing Asn97 and Asn100 through an affinity-maturation process.

This library was put on a filamentous phage via fusion to minor coat protein p3 (Marks et al. (1991) *J Mol Biol* 222, 581-597) and selected for binding to recombinant CD3ε.

10 candidate clones were identified in the initial screening, showing acceptable binding on recombinant antigen as measured by SPR as Fab fragments (produced in *E. coli*).

Only one of these clones, however, showed acceptable binding activity to CD3 expressing cells as measured by flow cytometry after conversion to IgG format.

The selected clone, termed "CD3$_{opt}$" herein and comprising the VH and VL sequences of SEQ ID NOs 7 and 11, respectively, was further evaluated and converted into bispecific format as described in the following.

Example 2—Binding of Optimized CD3 Binder to CD3

Binding to Recombinant CD3

Binding to recombinant CD3 was determined by surface plasmon resonance (SPR) for the optimized CD3 binder "CD3$_{opt}$" and the original CD3 binder "CD3$_{orig}$", both in human IgG$_1$ format with P329G L234A L235A ("PGLALA", EU numbering) mutations in the Fc region (SEQ ID NOs 12 and 14 (CD3$_{orig}$) and SEQ ID NOs 13 and 14 (CD3$_{opt}$)).

In order to assess the effect of the deamidation site removal and its effect on the stability of the antibodies, binding of the original and the optimized CD3 binder to recombinant CD3 was tested after temperature stress for 14 days at 37° C. or 40° C. Samples stored at −80° C. were used as reference. The reference samples and the samples stressed at 40° C. were in 20 mM His, 140 mM NaCl, pH 6.0, and the samples stressed at 37° C. in PBS, pH 7.4, all at a concentration of 1.2-1.3 mg/ml. After the stress period (14 days) samples in PBS were dialyzed back to 20 mM His, 140 mM NaCl, pH 6.0 for further analysis.

Relative Active Concentration (RAC) of the samples was determined by SPR as follows.

SPR was performed on a Biacore T200 instrument (GE Healthcare). Anti-Fab capturing antibody (GE Healthcare, #28958325) was immobilized on a Series S Sensor Chip CM5 (GE Healthcare) using standard amine coupling chemistry, resulting in a surface density of 4000-6000 resonance units (RU). As running and dilution buffer, HBS-P+ (10 mM HEPES, 150 mM NaCl pH 7.4, 0.05% Surfactant P20) was used. CD3 antibodies with a concentration of 2 μg/ml were injected for 60 s at a flow rate of 5 μl/min. CD3 antigen (see below) was injected at a concentration of 10 μg/ml for 120 s and dissociation was monitored at a flow rate of 5 μl/min for 120 s. The chip surface was regenerated by two consecutive injections of 10 mM glycine pH 2.1 for 60 s each. Bulk refractive index differences were corrected by subtracting blank injections and by subtracting the response obtained from the blank control flow cell. For evaluation, the binding response was taken 5 seconds after injection end. To normalize the binding signal, the CD3 binding was divided by the anti-Fab response (the signal (RU) obtained upon capture of the CD3 antibody on the immobilized anti-Fab antibody). The relative active concentration was calculated by referencing each temperature stressed sample to the corresponding, non-stressed sample.

The antigen used was a heterodimer of CD3 delta and CD3 epsilon ectodomains fused to a human Fc domain with knob-into-hole modifications and a C-terminal Avi-tag (see SEQ ID NOs 41 and 42).

Figure 2:
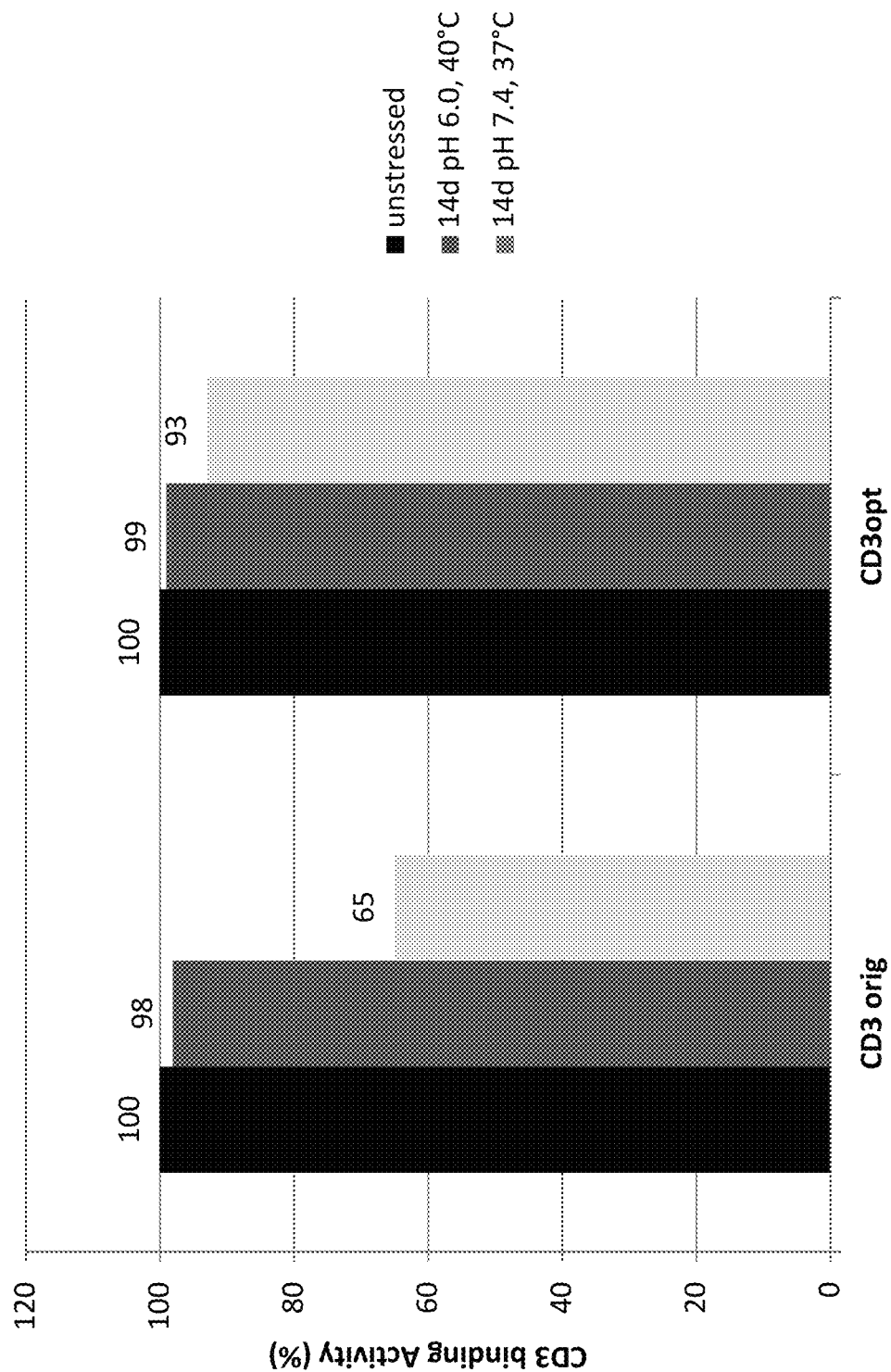
FIG. 2. Relative binding activity of original and optimized CD3 binders, $CD3_{orig}$ and $CD3_{opt}$, to recombinant CD3 as measured by SPR in unstressed condition, after 14 d at 40° C. pH 6, or after 14 d at 37° C. pH 7.4 (IgG format).

The results of this experiment are shown in FIG. 2. As can be seen, the optimized CD3 binder $CD3_{opt}$ showed strongly improved binding to CD3 after temperature stress (2 weeks at 37° C., pH 7.4) as compared to the original CD3 binder $CD3_{orig}$. This result demonstrates that the deamidation site removal was successful, and has yielded an antibody with superior stability properties, relevant for in vivo half-life, as well as formulation of the antibody at neutral pH.

Binding to CD3 on Jurkat Cells

Binding to CD3 on the human reporter T-cell line Jurkat NFAT was determined by FACS for the optimized CD3 binder "$CD3_{opt}$" and the original CD3 binder "$CD3_{orig}$", both in human $IgG_1$ format with P329G L234A L235A ("PGLALA", EU numbering) mutations in the Fc region (SEQ ID NOs 12 and 14 ($CD3_{orig}$) and SEQ ID NOs 13 and 14 ($CD3_{opt}$)).

Jurkat-NFAT reporter cells (GloResponse Jurkat NFAT-RE-luc2P; Promega #C5176501) are a human acute lymphatic leukemia reporter cell line with a NFAT promoter, expressing human CD3. The cells were cultured in RPMI1640, 2g/l glucose, 2 g/l NaHCO$_3$, 10% FCS, 25 mM HEPES, 2 mM L-glutamine, 1×NEAA, 1×sodium-pyruvate at 0.1-0.5 mio cells per ml. A final concentration of 200 μg per ml hygromycin B was added whenever cells were passaged.

For the binding assay, Jurkat NFAT cells were harvested, washed with PBS and resuspended in FACS buffer. The antibody staining was performed in a 96-well round bottom plate. Therefore 100'000 to 200'000 cells were seeded per well. The plate was centrifuged for 4 min at 400×g and the supernatant was removed. The test antibodies were diluted in FACS buffer and 20 μl of the antibody solution were added to the cells for 30 min at 4° C. To remove unbound antibody, the cells were washed twice with FACS buffer before addition of the diluted secondary antibody (PE-conjugated AffiniPure F(ab')2 Fragment goat anti-human IgG Fcγ Fragment Specific; Jackson ImmunoResearch #109-116-170). After 30 min incubation at 4° C. unbound secondary antibody was washed away. Before measurement the cells were resuspended in 200 μl FACS buffer and then analyzed by flow cytometry using a BD Canto II device.

Figure 3:
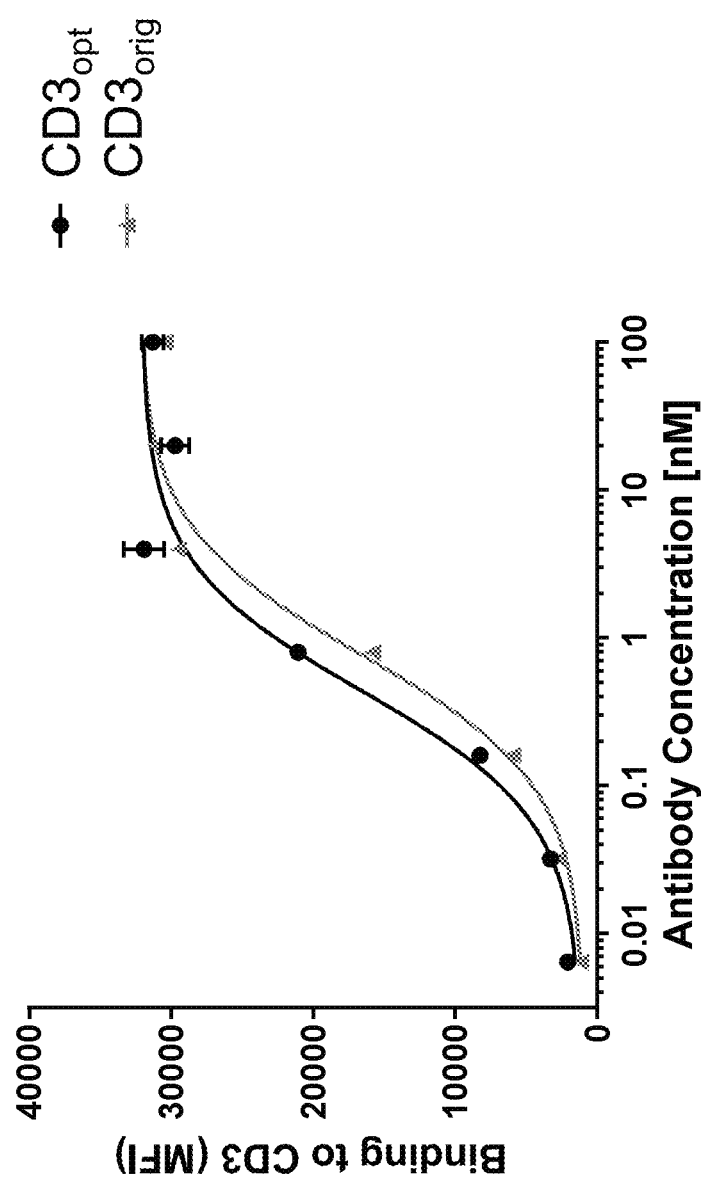
FIG. 3. Binding of original and optimized CD3 binders, $CD3_{orig}$ and $CD3_{opt}$, to Jurkat NFAT cells as measured by flow cytometry (IgG format). Antibodies bound to Jurkat NFAT cells were detected with a fluorescently labeled anti-human Fc specific secondary antibody.

As shown in FIG. 3, the optimized CD3 binder "$CD3_{opt}$" and the original CD3 binder "$CD3_{orig}$" bound comparably well to CD3 on Jurkat cells.

Example 3—Functional Activity of Optimized CD3 Binder

Figure 4:
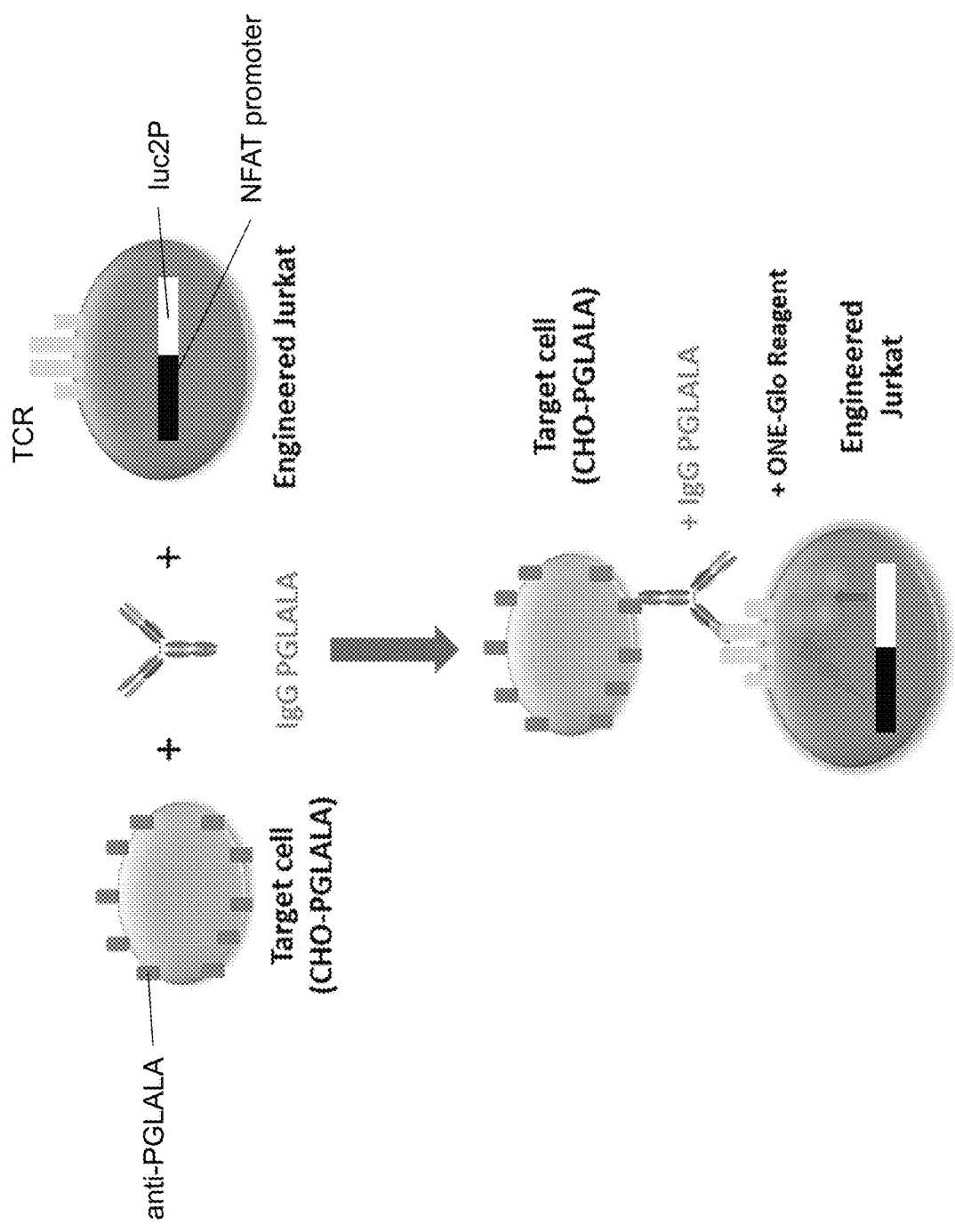
FIG. 4. Schematic illustration of the CD3 activation assay used in Example 3.

The functional activity of the optimized CD3 binder "$CD3_{opt}$" was tested in a Jurkat reporter cell assay and compared to the activity of the original CD3 binder "$CD3_{orig}$". To test the functional activity of the IgGs, anti-PGLALA expressing CHO cells were co-incubated with Jurkat NFAT reporter cells in the presence of increasing concentrations of $CD3_{opt}$ human $IgG_1$ PGLALA or $CD3_{orig}$ human $IgG_1$ PGLALA. Activation of CD3 on the Jurkat NFAT reporter cells upon T cell cross-linking induces the production of luciferase and luminescence can be measured as an activation marker. $CD3_{orig}$ human $IgG_1$ wt was included as negative control which cannot bind to anti-PGLALA expressing CHO cells and therefore cannot be crosslinked on Jurkat NFAT cells. A schematic illustration of the assay is provided in FIG. 4.

Anti-PGLALA expressing CHO cells are CHO-K1 cells engineered to express on their surface an antibody that specifically binds human $IgG_1$ Fc(PGLALA) (see WO 2017/072210, incorporated herein by reference). These cells were cultured in DMEM/F12 medium containing 5% FCS+1% GluMax. The Jurkat NFAT reporter cells are as described in Example 2.

Upon simultaneous binding of the CD3 hu$IgG_1$ PGLALA to anti-PGLALA expressed on CHO and CD3 expressed on Jurkat-NFAT reporter cells, the NFAT promoter is activated and leads to expression of active firefly luciferase. The intensity of luminescence signal (obtained upon addition of luciferase substrate) is proportional to the intensity of CD3 activation and signaling. Jurkat-NFAT reporter cells grow in suspension and were cultured in RPMI1640, 2g/l glucose, 2 g/l NaHCO3, 10% FCS, 25 mM HEPES, 2 mM L-glutamin, 1×NEAA, 1×sodium-pyruvate at 0.1-0.5 mio cells per ml, 200 μg per ml hygromycin. For the assay, CHO cells were harvested and viability determined using ViCell. 30 000 target cells/well were plated in a flat-bottom, white-walled 96-well-plate (Greiner bio-one #655098) in 100 μl medium and 50 μl/well of diluted antibodies or medium (for controls) were added to the CHO cells. Subsequently, Jurkat-NFAT reporter cells were harvested and viability assessed using ViCell. Cells were resuspended at 1.2 mio cells/ml in cell culture medium without hygromycin B and added to CHO cells at 60 000 cells/well (50 μl/well) to obtain a final effector-to-target (E:T) ratio of 2:1 and a final volume of 200 μl per well. Then, 4 μl of GloSensor (Promega #E1291) was added to each well (2% of final volume). Cells were incubated for 24 h at 37° C. in a humidified incubator. At the end of incubation time, luminescence was detected using TECAN Spark 10M.

Figure 5:
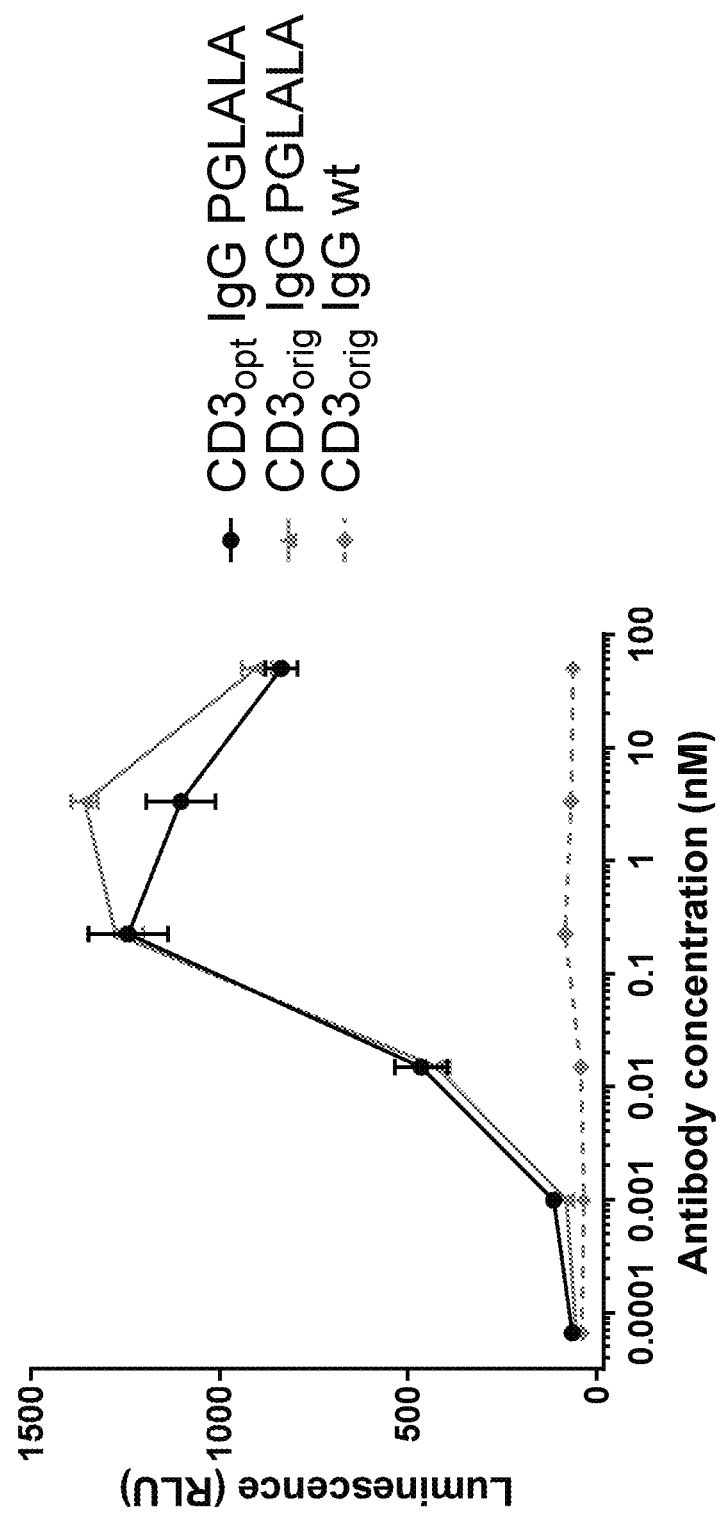
FIG. 5. Jurkat NFAT activation with original and optimized CD3 binders, $CD3_{orig}$ and $CD3_{opt}$ (IgG format). Jurkat NFAT reporter cells were co-incubated with anti-PGLALA expressing CHO (CHO-PGLALA) cells in the presence of $CD3_{orig}$ or $CD3_{opt}$ IgG PGLALA, or $CD3_{opt}$ IgG wt as negative control. CD3 activation was quantified by measuring luminescence after 24 h.

As shown in FIG. 5, the optimized CD3 binder $CD3_{opt}$ had a similar activity on Jurkat NFAT cells upon crosslinking as $CD3_{orig}$.

Example 4—Generation of T-Cell Bispecific Antibody Comprising Optimized CD3 Binder The optimized CD3 binder identified in Example 1 ("$CD3_{opt}$", SEQ ID NOs 7 (VH) and 11 (VL)) was used to generate T-cell bispecific antibodies (TCBs) targeting CD3 and CD19 ("CD19-TCB"), using anti-CD19 antibodies 2B11 or 018 as CD19 binding moiety (SEQ ID NOs 15-22 or 28-35, respectively).

A schematic illustration of the TCB molecules is provided in FIG. 6A, and their full sequences are given in SEQ ID NOs 39, 24, 25 and 27 (2B11), and SEQ ID NOs 36, 37, 38 and 27 (018).

Corresponding molecules comprising either of the above-mentioned anti-CD19 antibodies as target cell antigen binding moiety and $CD3_{orig}$ as CD3 binder were also prepared (SEQ ID NOs 39, 24, 25 and 26 (2B11), and SEQ ID NOs 40, 37, 38 and 26 (018)).

Figure 6:
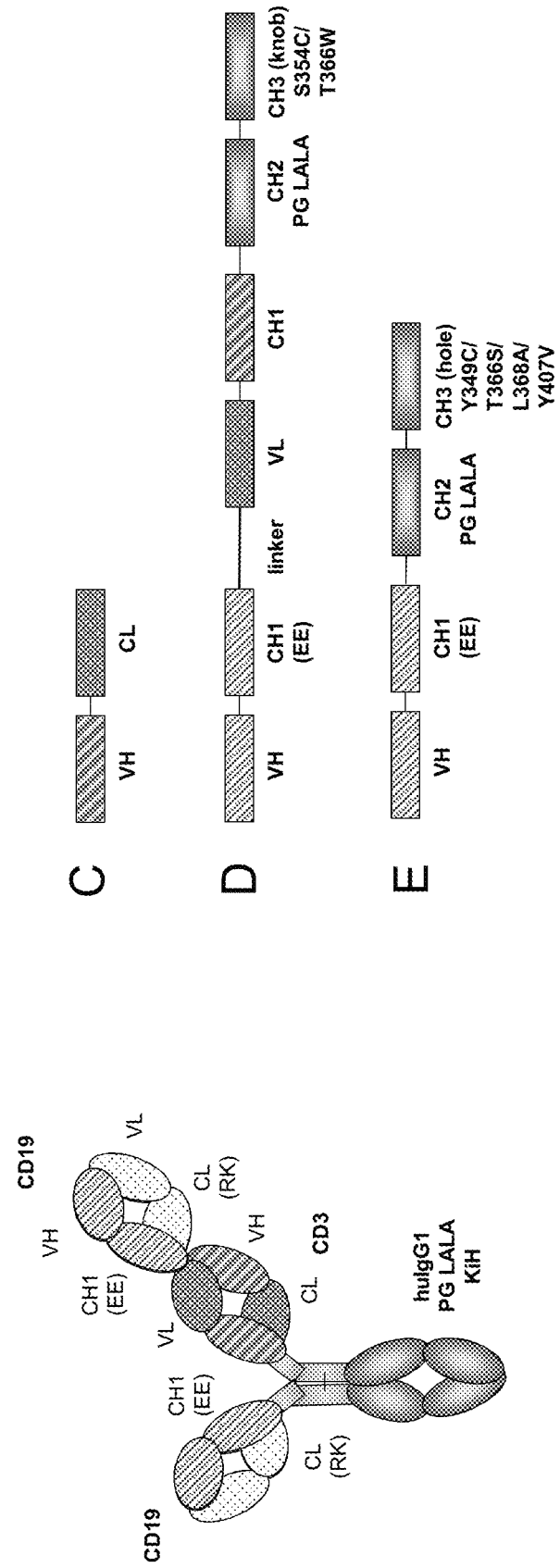
FIG. 6. (A) Schematic illustration of the T-cell bispecific antibody (TCB) molecules used in the Examples. All tested TCB antibody molecules were produced as "2+1 IgG CrossFab, inverted" with charge modifications (VH/VL exchange in CD3 binder, charge modifications in target antigen binders, EE=147E, 213E; RK=123R, 124K). (B-E) Components for the assembly of the TCB: light chain of anti-TYRP1 Fab molecule with charge modifications in CH1 and CL (B), light chain of anti-CD3 crossover Fab molecule (C), heavy chain with knob and PG LALA mutations in Fc region (D), heavy chain with hole and PG LALA mutations in Fc region (E).

The variable region of heavy and light chain DNA sequences were subcloned in frame with either the constant heavy chain or the constant light chain pre-inserted into the respective recipient mammalian expression vectors as shown in FIG. 6 B-E.

To improve correct pairing of the light chains with the corresponding heavy chains, mutations were introduced in the human CL (E123R, Q124K) and the human CH1 (K147E, K213E) of the CD19 binding Fab molecule.

For correct pairing of the heavy chains (formation of a heterodimeric molecule), knob-into-hole mutations were introduced in the constant region of the antibody heavy chains (T366W/S354C and T366S/L368A/Y407V/Y349C, respectively).

Furthermore, the P329G, L234A and L235A mutations were introduced in the constant region of the antibody heavy chains to abrogate binding to Fcγ receptors.

The TCBs were prepared by Evitria (Switzerland) using their proprietary vector system with conventional (non-PCR based) cloning techniques and using suspension-adapted CHO K1 cells (originally received from ATCC and adapted to serum-free growth in suspension culture at Evitria). For the production, Evitria used its proprietary, animal-component free and serum-free media (eviGrow and eviMake2) and its proprietary transfection reagent (eviFect). The cells were transfected with the corresponding expression vectors in a 1:1:2:1 ("vector knob heavy chain":"vector hole heavy chain":"vector CD3 light chain":"vector CD19 light chain"). Supernatant was harvested by centrifugation and subsequent filtration (0.2 μm filter).

As an alternative to the preparation at Evitria, TCB molecules were prepared in-house by transient transfection of HEK293 EBNA cells. Cells were centrifuged and, medium was replaced by pre-warmed CD CHO medium (Thermo Fisher, #10743029). Expression vectors were mixed in CD CHO medium, polyethylenimine (PEI; Polysciences Inc, #23966-1) was added, the solution vortexed and incubated for 10 minutes at room temperature. Afterwards, cells (2 mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added (W. Zhou and A. Kantardjieff, Mammalian Cell Cultures for Biologics Manufacturing, DOI: 10.1007/978-3-642-54050-9; 2014). One day after transfection, supplements (Feed, 12% of total volume) were added. Cell supernatants were harvested after 7 days by centrifugation and subsequent filtration (0.2 μm filter).

Proteins were purified from the harvested supernatant by standard methods. In brief, Fc containing proteins were purified from filtered cell culture supernatants by Protein A-affinity chromatography (equilibration buffer: 20 mM sodium citrate, 20 mM sodium phosphate, pH 7.5; elution buffer: 20 mM sodium citrate, pH 3.0). Elution was achieved at pH 3.0 followed by immediate pH neutralization of the sample. The protein was concentrated by centrifugation (Millipore Amicon® ULTRA-15, #UFC903096), and aggregated protein was separated from monomeric protein by size exclusion chromatography in 20 mM histidine, 140 mM sodium chloride, pH 6.0.

The concentrations of purified proteins were determined by measuring the absorption at 280 nm using the mass extinction coefficient calculated on the basis of the amino acid sequence according to Pace, et al., Protein Science, 1995, 4, 2411-1423. Purity and molecular weight of the proteins were analyzed by CE-SDS in the presence and absence of a reducing agent using a LabChipGXII (Perkin Elmer). Determination of the aggregate content was performed by HPLC chromatography at 25° C. using analytical size-exclusion column (TSKgel G3000 SW XL or UP-SW3000) equilibrated in running buffer (25 mM $K_2HPO_4$, 125 mM NaCl, 200 mM L-arginine monohydrocloride, pH 6.7 or 200 mM $KH_2PO_4$, 250 mM KCl pH 6.2, respectively).

Results from the biochemical and biophysical analysis of the prepared TCB molecules are given in Table 1.

All four TCB molecules could be produced in good quality.

TABLE 1

Biochemical and biophysical analysis of anti-CD3 antibody $CD3_{opt}$ in CD19-TCB format. Monomer content determined by analytical size exclusion chromatography. Purity determined by non-reducing CE-SDS.

| Molecule | Monomer [%] | Purity [%] |
|---|---|---|
| CD19(018) $CD3_{orig}$ | 91 | 97 |
| CD19(2B11) $CD3_{orig}$ | 96 | 97 |
| CD19(2B11) $CD3_{opt}$ | 98 | 99 |
| CD19(018) $CD3_{opt}$ | 98 | 99 |

Example 5—Functional Characterization of Optimized Anti-CD3 (Multispecific) Antibodies by Surface Plasmon Resonance (SPR)

SPR experiments were performed, using the CD19-TCB molecules prepared in Example 4, on a Biacore T200 instrument at 25° C. with HBS-EP+ as running buffer (0.01 M HEPES pH 7.4, 0.15 M NaCl, 0.005% Surfactant P20 (GE Healthcare, #BR-1006-69)). Anti-Fc(P329G) IgG (an antibody that specifically binds human $IgG_1$ Fc(P329G); "anti-PG antibody"—see WO 2017/072210, incorporated herein by reference) was directly immobilized by amine coupling on a C1 chip (GE Healthcare). The different TCB molecules were captured at 25 nM. Three-fold dilution series (in HBS-EP from 0.14 to 100 nM) of the CD19 antigen (human CD19 extracellular domain (ECD)—Fc fusion; see SEQ ID NOs 43 and 44) or the CD3 antigen (CD3/6— Fc fusion; see Example 2, SEQ ID NOs 41 and 42) were passed over the ligand at 30 μl/min for 240 s to record the association phase. The dissociation phase was monitored for 1500 s (CD19 antigen) or 800 s (CD3 antigen)s and triggered by switching from the sample solution to HBS-EP+. The chip surface was regenerated after every cycle using two injections of 10 mM glycine pH 2.1 for 60 sec. Bulk refractive index differences were corrected for by subtracting the response obtained on the reference flow cell (without captured TCB). The affinity constants were derived from the kinetic rate constants by fitting to a 1:1 Langmuir binding using the Biaeval software (GE Healthcare). The measurement was performed with three independent dilution series.

The kinetic constants for a 1:1 Langmuir binding were determined for the four tested TCBs to recombinant human CD19 (Table 2) and to recombinant human CD3 (Table 3).

TABLE 2

Binding to human CD19: Kinetic constants. Average and standard deviation (in parenthesis) of independent dilutions series in the same run.

| Molecule | $k_{on}$ (1/Ms) | $k_{off}$ (1/s) | $K_D$ (M) | $t_{1/2}$ (min) |
|---|---|---|---|---|
| CD19(018) CD3$_{orig}$ | 3.33E+05 (1.17E+04) | 3.16E−04 (9.54E−06) | 9.5E−10 (6E−11) | 36.6 |
| CD19(2B11) CD3$_{orig}$ | 4.34E+05 (1.20E+04) | 1.76E−04 (5.77E−07) | 4.0E−10 (1E−11) | 65.6 |
| CD19(2B11) CD3$_{opt}$ | 4.10E+05 (1.10E+04) | 1.46E−04 (1.53E−06) | 3.6E−10 (1E−11) | 79.1 |
| CD19(018) CD3$_{opt}$ | 3.35E+05 (9.64E+03) | 3.83E−04 (7.37E−06) | 1.14E−09 (6E−11) | 30.2 |

TABLE 3

Binding to human CD3: Kinetic constants. Average and standard deviation (in parenthesis) of independent dilutions series in the same run.

| Molecule | $k_{on}$ (1/Ms) | $k_{off}$ (1/s) | $K_D$ (M) | $t_{1/2}$ (min) |
|---|---|---|---|---|
| CD19(018) CD3$_{orig}$ | 9.33E+05 (2.57E+04) | 3.33E−03 (1.01E−04) | 3.57E−09 (1.7E−10) | 3.5 |
| CD19(2B11) CD3$_{orig}$ | 1.13E+06 (5.77E+03) | 3.78E−03 (1.10E−04) | 3.36E−09 (1.1E−10) | 3.1 |
| CD19(2B11) CD3$_{opt}$ | 2.37E+06 (1.93E+05) | 8.38E−03 (1.49E−04) | 3.55E−09 (2.2E−10) | 1.4 |
| CD19(018) CD3$_{opt}$ | 4.39E+06 (7.22E+05) | 1.30E−02 (1.00E−03) | 2.98E−09 (2.5E−10) | 0.9 |

The different binders show similar affinities in the different TCBs. The CD19 binder 2B11 has a $K_D$ of around 0.4 nM in the respective TCBs. The CD19 binder 018 is of slightly lower affinity with a $K_D$ around 1.1 nM in the respective TCBs. The TCBs with CD3 binder CD3$_{orig}$ or CD3$_{opt}$ have comparable affinity to CD3 with a $K_D$ around 3.4 nM. While the $K_D$ of the interaction with CD19 and CD3 antigens are similar, the kinetic is different. CD19 dissociates slower than CD3 does, but CD3 associates faster than CD19 does, thus leading to similar $K_D$ values.

Example 6—Binding of CD19-TCB Molecules with Optimized Anti-CD3 Antibody to Human CD19- and Human CD3-Expressing Cells The binding of the CD19-TCB molecules prepared in Example 4 to human CD19- and CD3-expressing target cells was tested. Two CD19-expressing cell lines with different levels of CD19 expression were used. Nalm-6, an acute lymphoblastic leukemia (ALL) cell line with high CD 19 expression and Z-138 (Mantle cell lymphoma) with average expression levels. CD3-binding was assessed using immortalized T lymphocyte line (Jurkat cell line). Briefly, cells were harvested, counted, checked for viability and resuspended at 1×10 6 cells/ml in FACS buffer (PBS+2% FCS+5 mM EDTA+0.25% sodium azide). 10011.1 of cell suspension (containing 0.1×10 6 cells) were incubated in round-bottom 96-well plate for 30 min at 4° C. with increasing concentrations of CD19-TCB molecules (200 nM-0.05 nM on Jurkat cells; 200 nM-0.0002 nM on Z-128 and Nalm-6 cells), washed twice with cold FACS buffer, re-incubated for further 30 min at 4° C. with the PE-conjugated AffiniPure F(ab')2 Fragment goat anti-human IgG Fcγ fragment specific secondary antibody (Jackson Immuno Research Lab PE #109-116-170), washed twice with cold FACS buffer and immediately analyzed by FACS using a FACS CantoII (software FlowJo 10.5.3). Binding curves and the EC50 values related to binding were calculated using GraphPad Prism 7.

Figure 7:
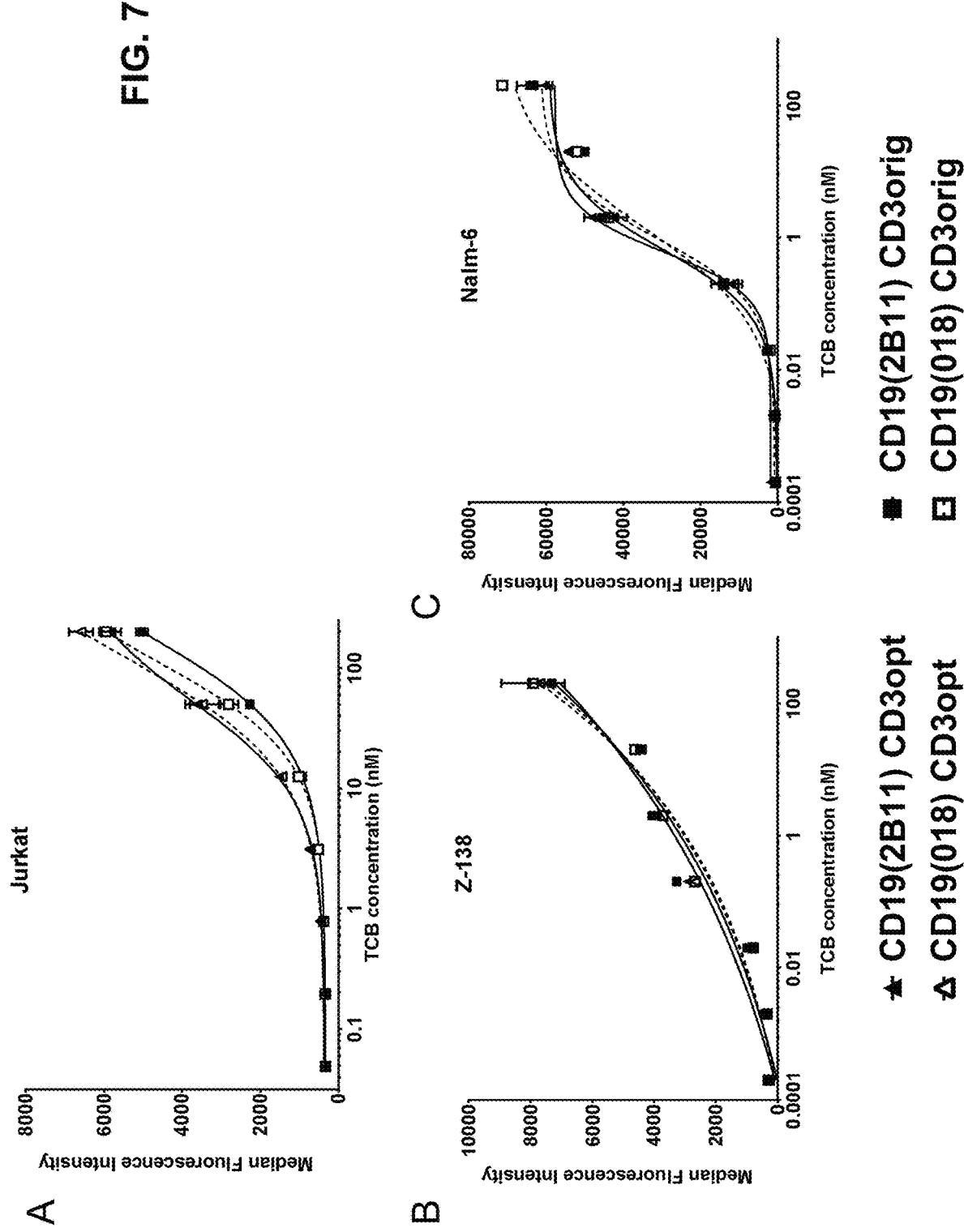
FIG. 7. Binding of CD19-TCB antibodies to CD3-expressing Jurkat cells (A) and to CD19-expressing Z-138 (B) and Nalm-6 (C) cells, as measured by flow cytometry.

The results are shown in FIG. 7 and Table 4 and 5. The CD19-TCB molecules comprising CD3$_{opt}$ as CD3 binder show comparable (or slightly better) CD3 binding to molecules comprising the CD3 binder CD3$_{orig}$ (FIG. 7A and Table 4).

The CD19-TCB molecules (comprising either 2B11 or 018 as CD19 binders) show comparable binding to CD19-expressing cells (FIG. 7B, C and Table 5). For Z-138 cells, the EC50 values could not be calculated since the binding curve did not reach saturation.

TABLE 4

EC50 values (nM) of binding of CD19-TCBs to human CD3-expressing Jurkat cells.

| Antibodies | EC50 [nM] |
|---|---|
| CD19(2B11) CD3$_{opt}$ | 53.45 |
| CD19(018) CD3$_{opt}$ | 126.5 |
| CD19(2B11) CD3$_{orig}$ | 203.4 |
| CD19(018) CD3$_{orig}$ | 115.1 |

TABLE 5

EC50 values (nM) of binding of CD19-TCBs to human CD19-expressing target Nalm-6 cells.

| Antibodies | EC50 [nM] |
|---|---|
| CD19(2B11) CD3$_{opt}$ | 0.6 |
| CD19(018) CD3$_{opt}$ | 1 |
| CD19(2B11) CD3$_{orig}$ | 0.7 |
| CD19(018) CD3$_{orig}$ | 1.5 |

Example 7—Tumor Cell Lysis and T Cell Activation, Induced by CD19-TCB Molecules with Optimized Anti-CD3 Antibody The lysis of CD19-expressing tumor cells and subsequent T cell activation mediated by the CD19-TCB molecules prepared in Example 4 was assessed on Nalm-6 cells (ALL) and Z-138 cells (Mantle cell lymphoma). Human PBMCs were used as effectors and tumor lysis was detected at 20 h of incubation with the different TCB molecules.

Peripheral blood mononuclear cells (PBMCs) were prepared by Histopaque density centrifugation of enriched lymphocyte preparations (buffy coats) obtained from a healthy human donor. Fresh blood was diluted with sterile PBS and layered over Histopaque gradient (Sigma,

H8889). After centrifugation (450×g, 30 minutes, no brake, room temperature), the plasma above the PBMC-containing interphase was discarded and PBMCs transferred in a new falcon tube subsequently filled with 50 ml of PBS. The mixture was centrifuged (350×g, 10 minutes, room temperature), the supernatant discarded and the PBMC pellet incubated in erythrocyte lysing solution for 5 min at 37° C. before washing with sterile PBS (centrifugation 300×g, 10 minutes). The resulting PBMC population was resuspended in PBS and counted automatically (ViCell). 50 mio PBMCs per cyrovial were frozen in RPMI1640 medium (Gibco, #21870076) containing 10% FCS and 1% GlutaMAX (Gibco) containing 10% DMSO (Sigma, #D2650). PBMCs were thawed the day of the assay and counted again automatically (ViCell). The amount needed was washed once with sterile PBS. B cell depletion was performed using CD20 microbeads (Miltenyi, #130-091-104) according to the manufacturer's instructions. B cell depleted PBMCs were counted (ViCell) and resuspended at 5×10 6 cells/ml in RPMI1640 medium containing 10% FCS and 1% GlutaMAX.

For the killing assay, 0.25 mio B cell-depleted PBMCs were added to the U-bottom 96-well plates. Briefly, target cells were harvested, washed, and plated at density of 50 000 cells/well resulting in an final effector-to-target (E:T) ratio of 5:1. The TCB molecules were added at the indicated concentrations (range of 0.02 pM-1000 pM, in triplicates). CD107a (LAMP-1) was directly stained already in the assay (PE anti-human CD107a; Biolegend, #328608).

Tumor cell lysis was assessed after 20 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

For the assessment of T cell activation occurring upon tumor cell lysis, PBMCs were centrifuged at 400×g for 4 min and washed twice with FACS buffer. Briefly, cells were washed twice with PBS, followed by live/dead staining (Zombie Aqua Fixable Viability kit; Biolegend, #423102, 20 min at RT). After repeated washing first with PBS followed by FACS Buffer the surface staining for CD3 (PE-Cy5 anti-human CD3; BD Pharmigen, #555341), CD4 (BV605 anti-human CD4; Biolegend, #317438), CD8 (BV711 anti-human CD8; Biolegend, #301044), CD25 (PE-Cy7 anti-human CD25; Biolegend, #302612) and CD69 (BV421 anti-human CD69; Biolegend, #310930) was performed according to the suppliers' indications. Cells were washed twice with 150 μl/well FACS buffer and fixed with 120 μl/well 1× lysing solution (BD Biosciences #349202). Samples were analyzed at BD FACS Fortessa (Software FlowJo 10.5.3).

Figure 8:
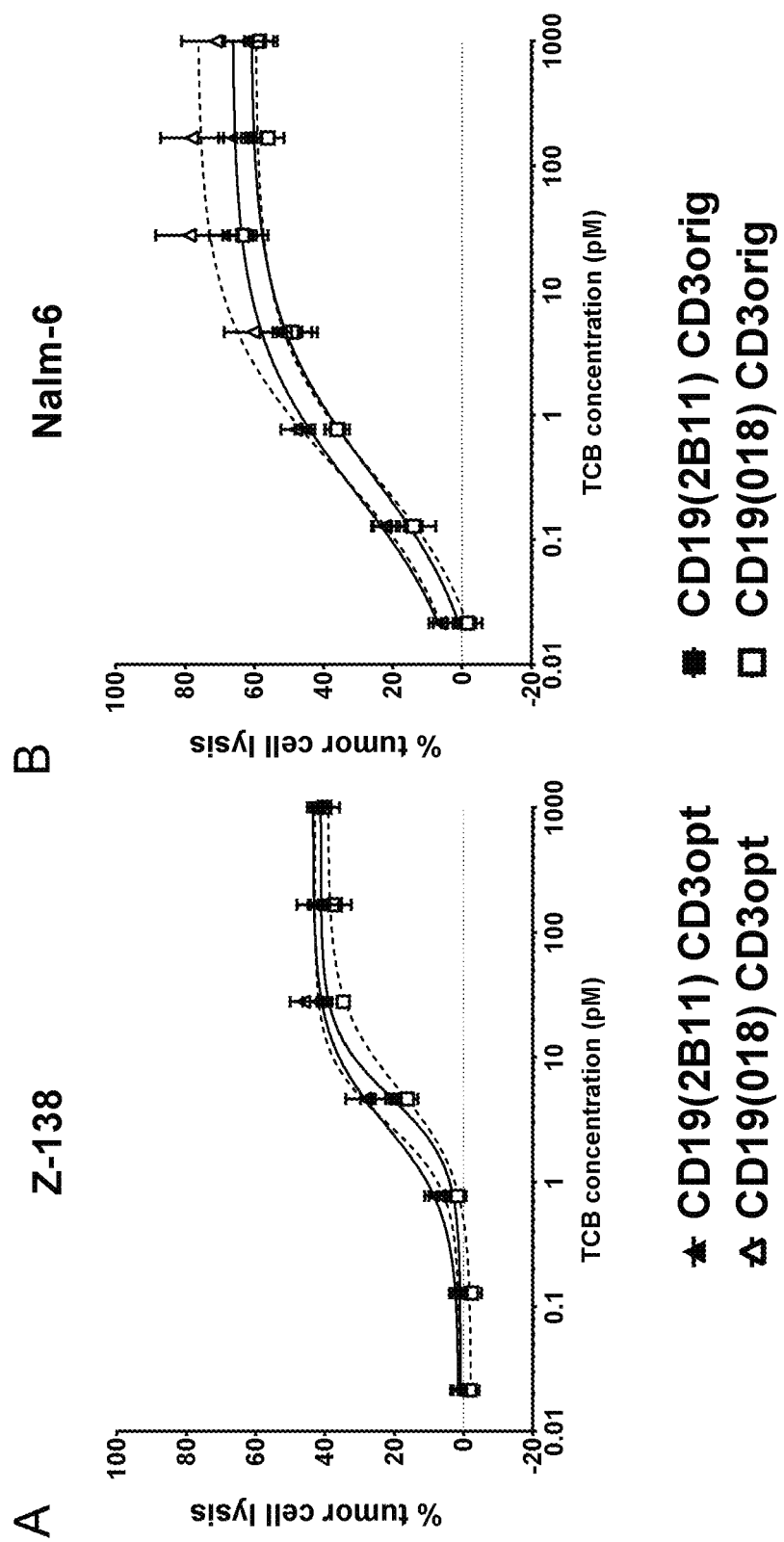
FIG. 8. Target-specific killing of CD19+ target cells induced by CD19-TCB antibodies. (A) Z-138 target cells, (B) Nalm-6 target cells.
Figure 9:
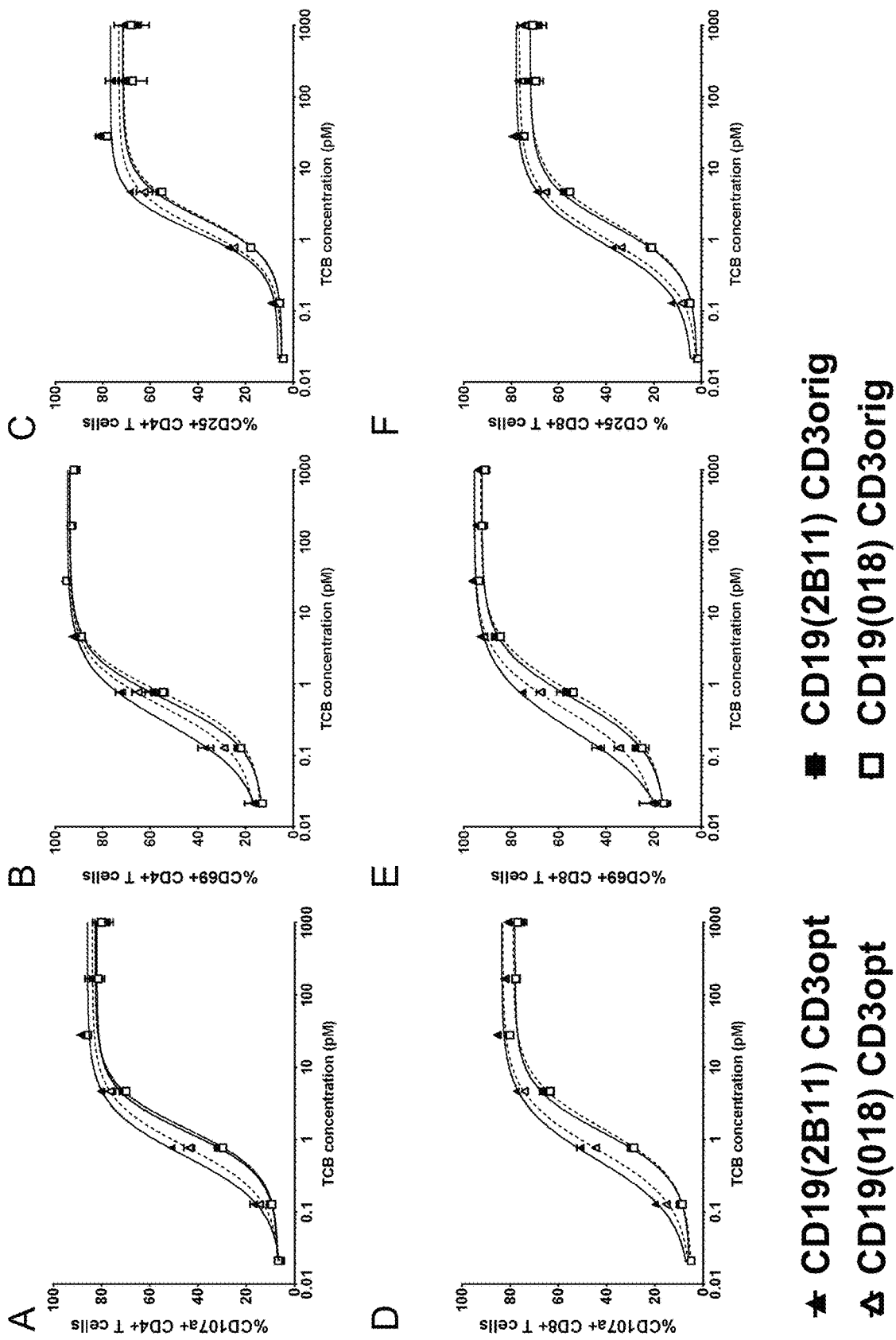
FIG. 9. T cell activation induced by CD19-TCB antibodies after killing of Z-138 target cells. (A) CD25 expression on CD4 T cells, (B) CD69 expression on CD4 T cells, (C) CD107 expression on CD4 T cells, (D) CD25 expression on CD8 T cells, (E) CD69 expression on CD8 T cells, (F) CD107 expression on CD8 T cells.
Figure 10:
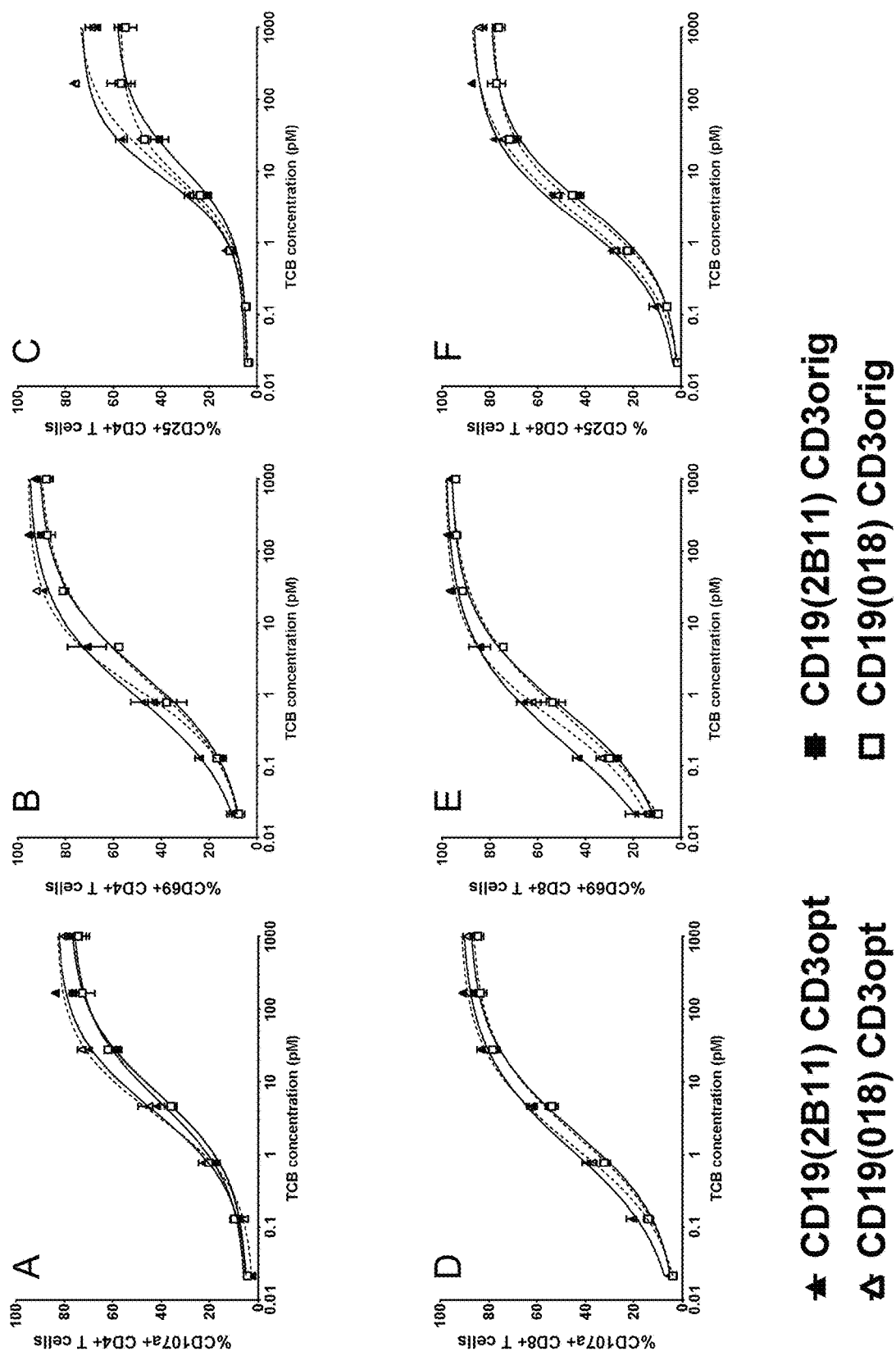
FIG. 10. T cell activation induced by CD19-TCB antibodies after killing of Nalm-6 target cells. (A) CD25 expression on CD4 T cells, (B) CD69 expression on CD4 T cells, (C) CD107 expression on CD4 T cells, (D) CD25 expression on CD8 T cells, (E) CD69 expression on CD8 T cells, (F) CD107 expression on CD8 T cells.

FIG. 8 shows that CD19-TCB molecules induced target-specific killing of CD19+ target cells. The four different CD19-TCB molecules were overall comparable in inducing lysis of CD19-expressing tumor cells. FIGS. 9 and 10 show that the CD19-TCBs containing the $CD3_{opt}$ binder show slightly superior induction of T cell activation after tumor killing (CD25, CD69 and CD107 expression on CD8 and CD4 T cells upon killing of Nalm-6 or Z-138 target cells) compared to molecules containing the $CD3_{orig}$ binder. No effect on T cell activation of the CD19 binders 2B11 and 018 was observed.

TABLE 6

EC50 values (pM) of tumor cell lysis mediated by CD19-TCB molecules evaluated on CD19-expressing tumor target cells.

| EC50 (pM) | Nalm-6 | Z-138 |
|---|---|---|
| CD19(2B11) $CD3_{opt}$ | 0.24 | 2.9 |
| CD19(018) $CD3_{opt}$ | 0.4 | 3 |
| CD19(2B11) $CD3_{orig}$ | 0.3 | 4.8 |
| CD19(018) $CD3_{orig}$ | 0.3 | 5.4 |

TABLE 7

EC50 values (pM) of T cell activation upon tumor cell lysis mediated by CD19-TCB molecules using Z-138 as target cells.

| Activation marker | CD19(2B11) $CD3_{opt}$ | CD19(018) $CD3_{opt}$ | CD19(2B11) $CD3_{orig}$ | CD19(018) $CD3_{orig}$ |
|---|---|---|---|---|
| CD25/CD4 | 1.3 | 1.4 | 2 | 2 |
| CD69/CD4 | 0.3 | 0.5 | 0.6 | 0.7 |
| CD107a/CD4 | 0.6 | 0.8 | 1.3 | 1.4 |
| CD25/CD8 | 0.9 | 1 | 1.5 | 1.7 |
| CD69/CD8 | 0.2 | 0.4 | 0.6 | 0.8 |
| CD107a/CD8 | 0.5 | 0.7 | 1.3 | 1.4 |

TABLE 8

EC50 values (pM) of T cell activation upon tumor cell lysis mediated by CD19-TCB molecules using Nalm-6 as target cells.

| Activation marker | CD19(2B11) $CD3_{opt}$ | CD19(018) $CD3_{opt}$ | CD19(2B11) $CD3_{orig}$ | CD19(018) $CD3_{orig}$ |
|---|---|---|---|---|
| CD25/CD4 | 8 | 11 | 12 | 7 |
| CD69/CD4 | 0.9 | 1.2 | 1.9 | 1.7 |
| CD107a/CD4 | 4.1 | 3.6 | 6.9 | 5.5 |
| CD25/CD8 | 2.1 | 2.4 | 3.4 | 2.8 |
| CD69/CD8 | 0.2 | 0.4 | 0.7 | 0.4 |
| CD107a/CD8 | 1.2 | 1.4 | 2.1 | 1.9 |

Example 8—Determination of Thermal Stability of CD19-TCB Molecule with Optimized Anti-CD3 Antibody Thermal stability of the CD19-TCB molecule comprising the optimized anti-CD3 antibody $CD3_{opt}$ (and the CD19 binder 2B11, see Example 4) was monitored by Static Light Scattering (SLS) by applying a temperature ramp using an Uncle system (Unchained Labs, USA).

9 μl of filtered protein sample with a protein concentration of 1 mg/ml was applied to the Uncle device. The temperature was ramped from 30 to 90° C. at 0.1° C./min, with scattering intensity at 266 nm being collected.

The result is shown in Table 9.

TABLE 9

Thermal stability of CD19-TCB molecule as measured by static light scattering.

| anti-CD3 antibody | $T_{agg}$ [° C.] |
|---|---|
| $CD3_{opt}$ | 64.8 |

Example 9—Characterization of CD19-TCB Molecule with Optimized Anti-CD3 Antibody by Surface Plasmon Resonance (SPR) after Stress In order to confirm the effect of the deamidation site removal and its effect on the stability of the antibody, the CD19-TCB molecule comprising the optimized anti-CD3 antibody CD3$_{opt}$ (and the CD19 binder 2B11, see Example 4) was incubated for 14 days at 37° C., pH 7.4 and at 40° C., pH 6 and further analyzed by SPR for their binding capability to human CD3ɛ/δ. Samples stored at −80° C. pH 6 were used as reference. The reference samples and the samples stressed at 40° C. were in 20 mM His, 140 mM NaCl, pH 6.0, and the samples stressed at 37° C. in PBS, pH 7.4, all at a concentration of 1.0 mg/ml. After the stress period (14 days) samples in PBS were dialyzed back to 20 mM His, 140 mM NaCl, pH 6.0 for further analysis.

All SPR experiments were performed on a Biacore T200 instrument (GE Healthcare) at 25° C. with EIBS-P+(10 mM HEPES, 150 mM NaCl pH 7.4, 0.05% Surfactant P20) as running and dilution buffer. Biotinylated human CD3ɛ/δ (see Examples 2, SEQ ID NOs 41 and 42) as well as biotinylated anti-huIgG (Capture Select, Thermo Scientific, #7103262100) were immobilized on a Series S Sensor Chip SA (GE Healthcare, #29104992), resulting in surface densities of at least 1000 resonance units (RU). TCBs with a concentration of 2 μg/ml were injected for 30 s at a flow rate of 5 μl/min, and dissociation was monitored for 120 s. The surface was regenerated by injecting 10 mM glycine pH 1.5 for 60 s. Bulk refractive index differences were corrected by subtracting blank injections and by subtracting the response obtained from a blank control flow cell. For evaluation, the binding response 5 seconds after injection end was taken. To normalize the binding signal, the CD3 binding was divided by the anti-huIgG response (the signal (RU) obtained upon capture of the TCB on the immobilized anti-huIgG antibody). The relative binding activity was calculated by referencing each temperature stressed sample to the corresponding, non-stressed sample.

As shown in Table 10, binding of the CD19-TCB comprising the optimized anti-CD3 binder CD3$_{opt}$ to CD3ɛ/δ is essentially unaffected upon stress, in line with the results for the CD3 binder as such (Example 2).

TABLE 10

Binding activity of CD19-TCB molecule to human CD3ɛ/δ after incubation at pH 6/40° C. or pH 7.4/37° C. for 2 weeks.

| anti-CD3 antibody | binding activity [%] | |
| --- | --- | --- |
| | 2 weeks at pH 6.0/40° C. | 2 weeks at pH 7.4/37° C. |
| CD3$_{opt}$ | 98 | 98 |

Example 10—In Vivo B Cell Depletion and Cytokine Release Induced by CD19-TCB Molecule with Optimized Anti-CD3 Antibody To understand the potency and safety profile of the CD19-TCB molecule comprising the optimized anti-CD3 antibody CD3$_{opt}$ and the 2B11 CD19 binder, an in vivo mode of action study was conducted assessing peripheral B cell depletion and cytokine release in humanized NSG mice.

Female NSG mice, age 4-5 weeks at start of the experiment (Jackson Laboratory), were maintained under specific-pathogen-free condition with daily cycles of 12 h light/12 h darkness according to committed guidelines (GV-Solas; Felasa; TierschG). The experimental study protocol was reviewed and approved by local government (ZH223-17). After arrival, animals were maintained for one week to get accustomed to the new environment and for observation. Continuous health monitoring was carried out on a regular basis.

Female NSG mice were injected i.p. with 15 mg/kg of Busulfan followed one day later by an i.v. injection of $1 \times 10^5$ human hematopoietic stem cells isolated from cord blood. At week 14-16 after stem cell injection, mice were bled sublingual and blood was analyzed by flow cytometry for successful humanization. Efficiently engrafted mice were randomized according to their human T cell frequencies into the different treatment groups. Following randomization, mice from three groups were pre-treated once with obinutuzumab (Gazyva®) (30 mg/kg), as a measure to prevent excessive cytokine release.

7 days after this pre-treatment, on day 0, all groups received the CD19-TCB at different doses, CD20-TCB (a TCB targeting CD20 and comprising the CD3 binder CD3$_{orig}$), or vehicle. Three different doses (0.5, 0.15 and 0.05 mg/kg) of CD19-TCB were injected. CD20-TCB (0.15 mg/kg) with and without Gazyva® pre-treatment was used as comparison agent. All mice were injected i.v. with 200 μl of the appropriate solution. Three mice per group were bled at 4 h, 24 h and 72 h after therapy (day 0).

Figure 11:
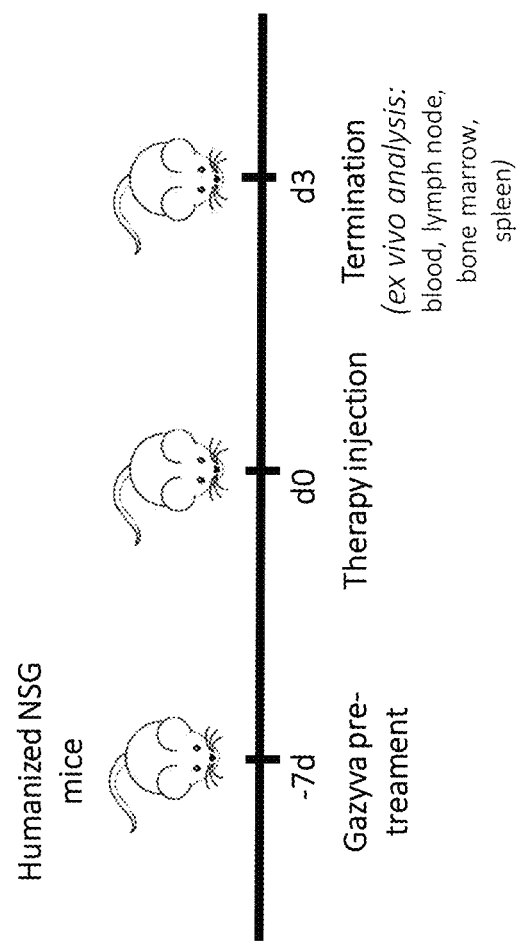
FIG. 11. Design of the in vivo study of Example 10.

The study design is shown in FIG. 11, and the study groups are summarized in Table 11.

TABLE 11

Study groups (number of animals per group = 3, treatment administration = i.v.)

| Group | Treatment | Dose (mg/kg) |
| --- | --- | --- |
| A | Vehicle | — |
| B | CD19-TCB | 0.5 |
| C | CD19-TCB | 0.15 |
| D | CD19-TCB | 0.05 |
| E | Obinutuzumab (Gazyva ®) | 30 |
| | CD19-TCB | 0.5 |
| F | CD20-TCB | 0.15 |
| G | Obinutuzumab (Gazyva ®) | 30 |
| | CD20-TCB | 0.15 |

At termination (day 3), mice were sacrificed and spleen, lymph nodes (LN) and bone marrow (BM) were harvested, weighed, and single cell suspensions were prepared through an enzymatic digestion with Liberase and DNAse for subsequent FACS analysis. Spleen single cells as well as all blood samples were stained for human CD45, CD19, CD20 and analyzed at the BD Fortessa flow cytometer. Additionally, serum from the three bleeding time points were analyzed for cytokine content by Multiplex analysis.

Figure 12:
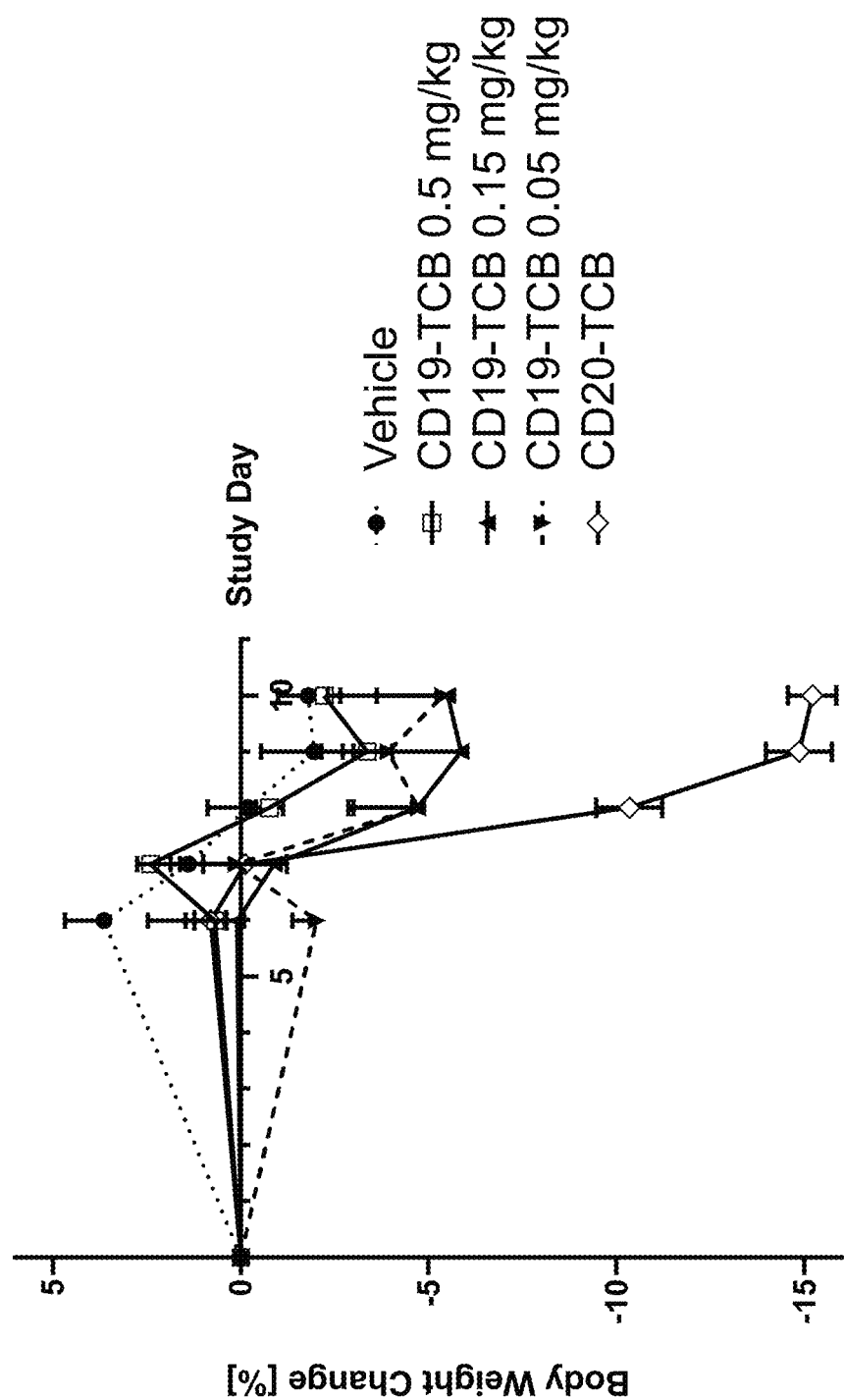
FIG. 12. Body weight change upon treatment with different doses of CD19-TCB or CD20-TCB, in the study of Example 10. n=3 mice per group. Mean+/−SEM.
Figure 13:
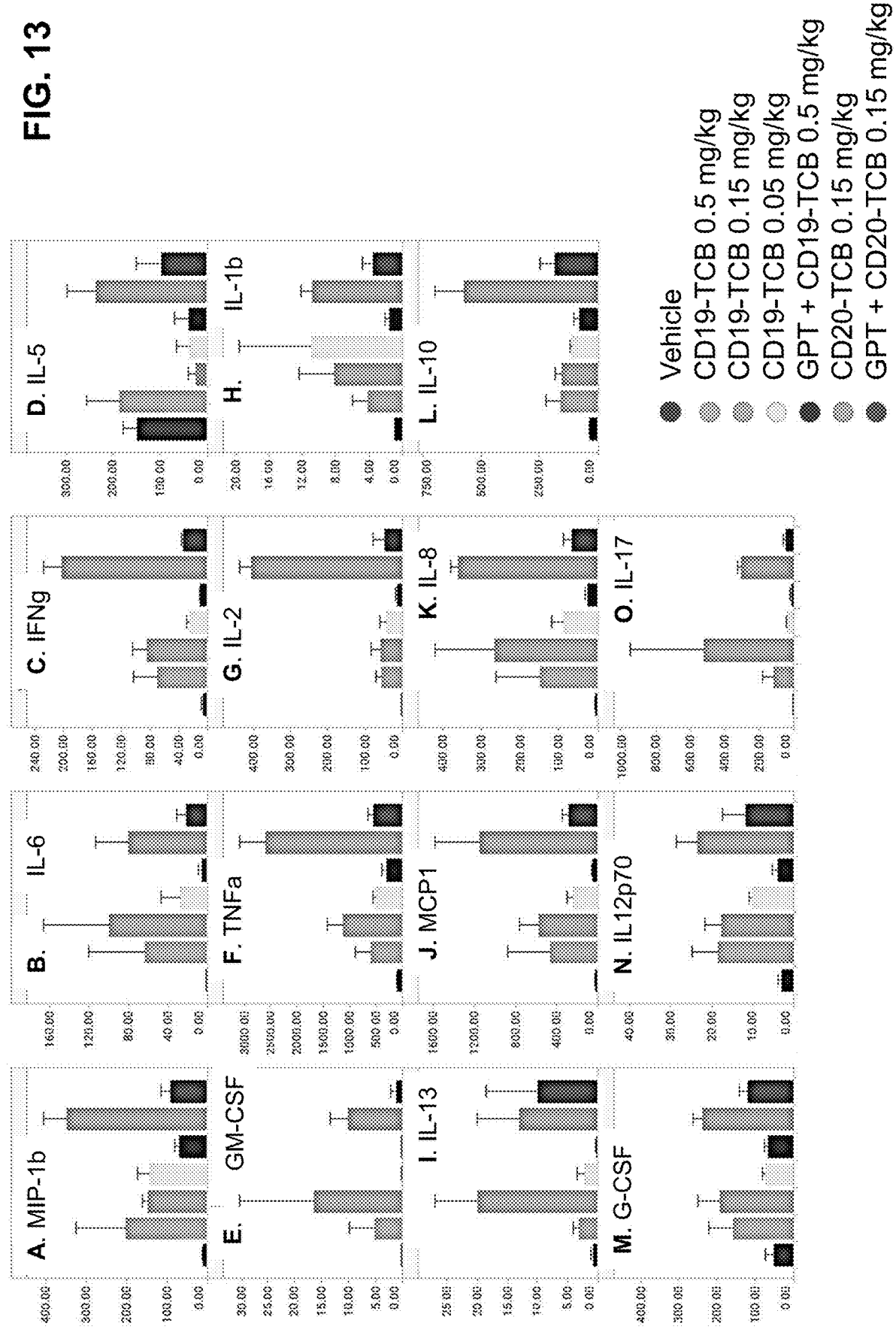
FIG. 13. Cytokine release in serum at 4 hours after treatment with CD19-TCB or CD20-TCB, with or without obinituzumab (Gazyva®) pre-treatment (GPT), in the study of Example 10. (A) MIP-1β, (B) IL-6, (C) IFN-γ, (D) IL-5, (E) GM-CSF, (F) TNF-α, (G) IL-2, (H) IL-10, (I) IL-13, (J) MCP1, (K) IL-8, (L) IL-10, (M) G-CSF, (N) IL-12p70, (O) IL-17. Bars in each panel from left to right: CD19-TCB 0.5 mg/kg, CD19-TCB 0.15 mg/kg, CD19-TCB 0.05 mg/kg, GPT+CD19-TCB 0.5 mg/kg, CD20-TCB 0.15 mg/kg, GPT+CD20-TCB 0.15 mg/kg. Mean+SEM.

FIG. 12 shows the body weight change (%) in the treatment groups. The CD19-TCB molecule induced less body weight drop compared to CD20-TCB treatment. This body weight drop was independent of the dose used. Furthermore, cytokine analysis in the sera of treated animals revealed a peak of elevated cytokine levels at 4 h after treatment with the CD20-TCB molecule (which could be reduced by pre-treatment with Gazyva® (GPT)), whereas only low levels of cytokines were detected for the CD19-TCB molecule (FIG. 13).

Figure 14:
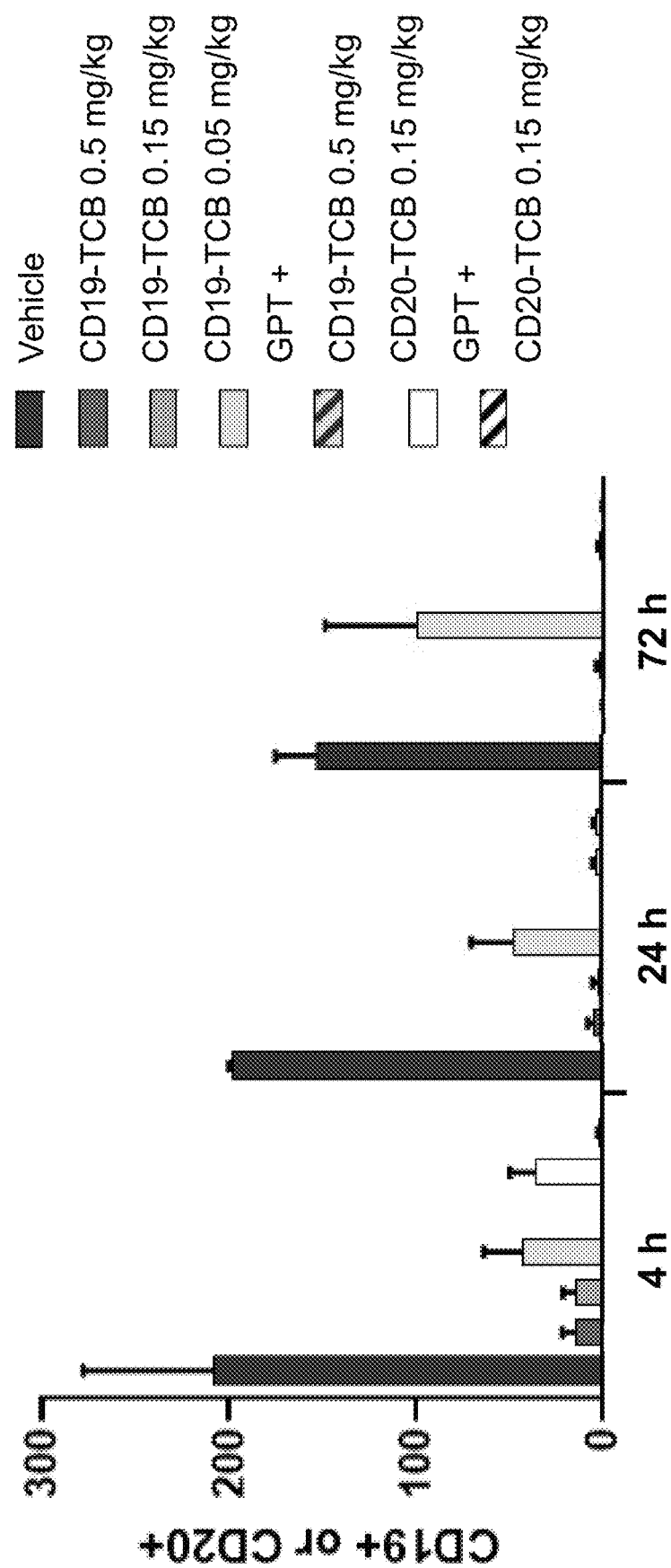
FIG. 14. B cell counts in blood at 4 hours, 24 hours and 72 hours after treatment CD19-TCB or CD20-TCB, with or without obinituzumab (Gazyva®) pre-treatment (GPT), in the study of Example 10. Mean+SEM.

The Immuno-PD data (FIG. 14) on the kinetics of B cell depletion in blood revealed strong depletion of CD19+ CD20+B cells (mean counts of CD19+ or CD20+ cells/μl blood+/−SEM) over time by CD19-TCB and suggested a dose-dependency. This B cell depletion effect was also seen in all lymphatic organs analyzed at 72 h upon treatment with CD19-TCB being as potent as CD20-TCB (data not shown).

Figure 15:
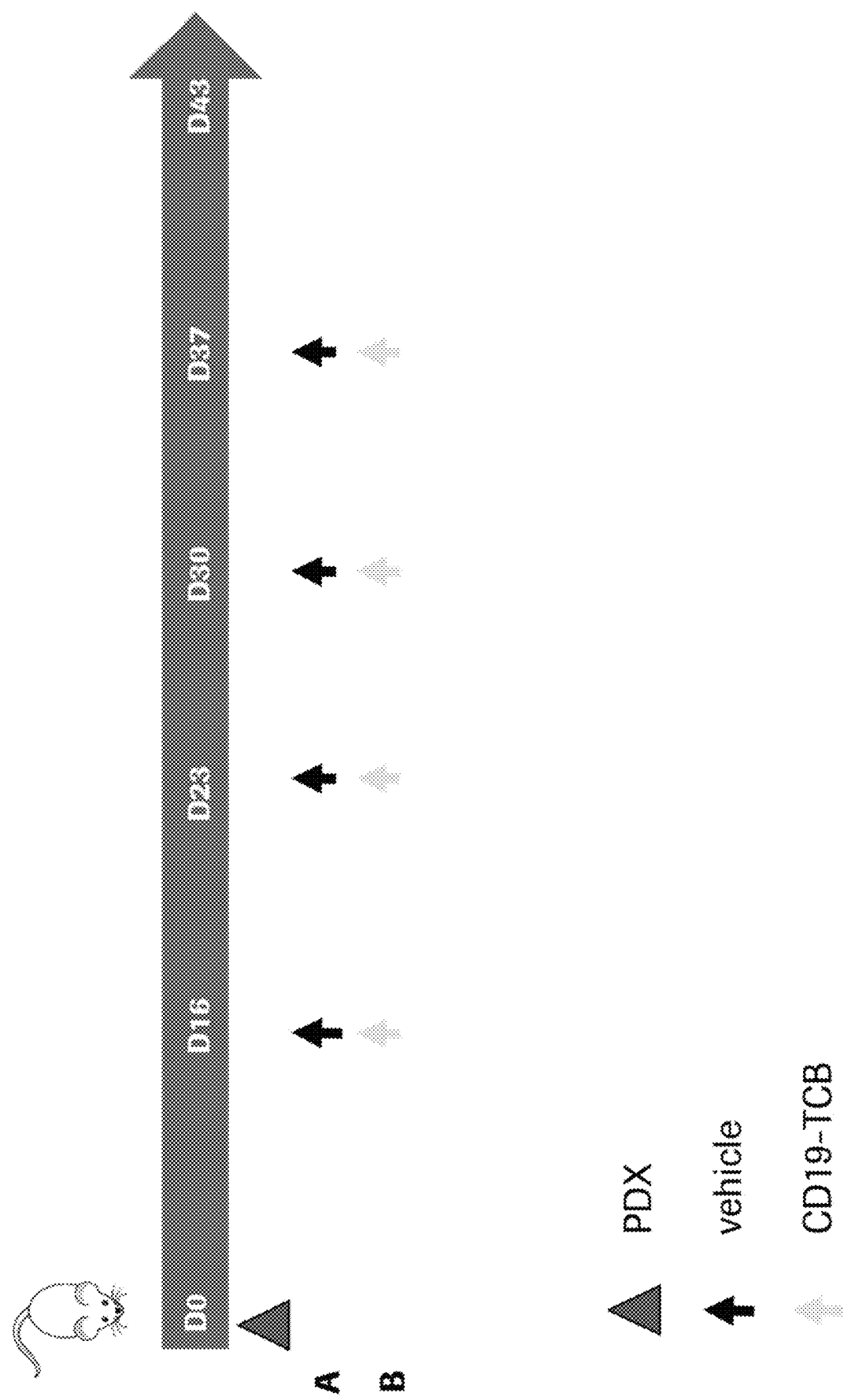
FIG. 15. Treatment schedule and experimental set-up. Humanized NSG mice were subcutaneously engrafted with a lymphoma patient-derived xenograft (PDX) (5 million cells). Tumor volumes were calculated from caliper measurements. When they reached 200 mm$^3$, mice were randomized in groups of 8 based on their tumor size. Mice were then weekly injected (i.v.) with vehicle or 0.5 mg/kg CD19-TCB.

Example 11—Tumor Growth Control in Mouse Xenograft Experiment by CD19-TCB Molecule with Optimized Anti-CD3 Antibody To evaluate the anti-tumor efficacy of CD19-TCB molecule comprising the optimized anti-CD3 antibody $CD3_{opt}$ and the 2B11 CD19 binder in vivo, humanized NSG mice were engrafted with CD19+ lymphoma patient derived xenograft (PDX) cells from a patient who relapsed R-CHOP treatment. When the tumor volume reached 200 mm³, mice were randomized in groups of 8 based on their tumor size. They were then weekly injected with 0.5 mg/kg CD19-TCB or vehicle (i.v.) as illustrated in FIG. 15. To assess the effect of CD19-TCB on tumor growth, tumor volumes were calculated from caliper measurements twice or three times per week.

Figure 16:
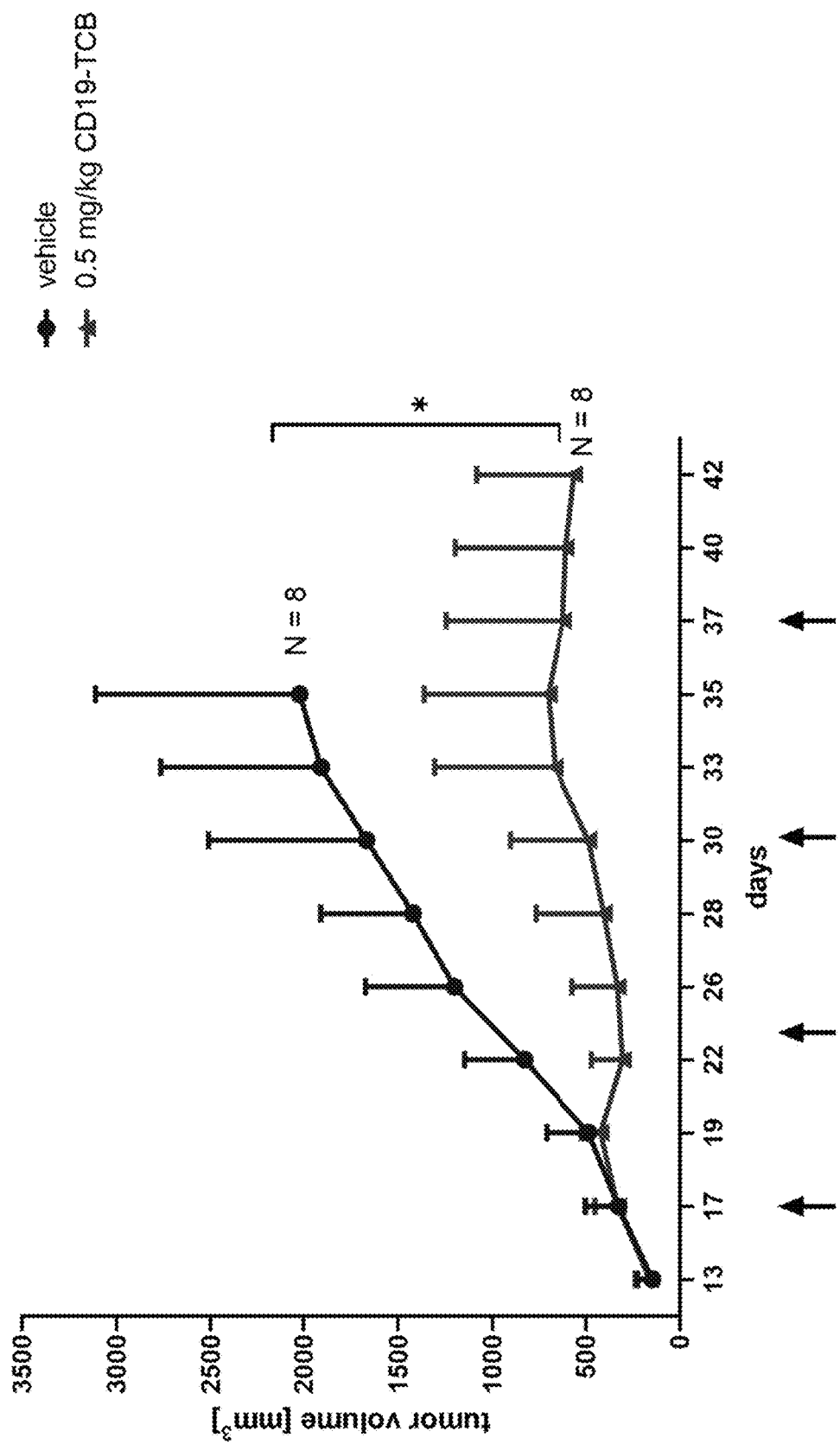
FIG. 16. Effect of CD19-TCB treatment on tumor growth. Tumor volumes were calculated from caliper measurements two (volume <1000 mm$^3$) or three times (volume ≥1000 mm$^3$) per week for n=7 mice in group B and n=8 mice in group A, as described in FIG. 15. Mean+SD with *p≤0.05, p≤0.01, *p≤0.001 by Mann-Whitney test. Arrows indicate each of the 4 treatments with CD19-TCB or vehicle.

As a result, weekly treatment CD19-TCB exerted a significant tumor growth control as compared to treatment with vehicle (FIG. 16). This data demonstrate that the weekly dosing with 0.5 mg/kg CD19-TCB is efficacious in lymphoma PDX-bearing huNSG mice, and suggest that lymphoma patients relapsing R-CHOP treatment could benefit from CD19-TCB treatment.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating an autoimmune disease in an individual, comprising administering to said individual an effective amount of an antibody that binds to CD3 and CD19, wherein the antibody comprises:
   (a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10;
   (b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21; and
   (c) an Fc domain composed of a first subunit and a second subunit;
   wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

2. The method of claim 1, wherein:
   (a) the first antigen binding domain comprises a VH comprising an amino acid sequence that is at least 95% identical to the amino acid sequence of SEQ ID NO: 7 and a VL comprising an amino acid sequence that is at least 95% identical to the amino acid sequence of SEQ ID NO: 11; and
   (b) each of the second antigen binding domain and the third antigen binding domain comprises a VH comprising an amino acid sequence that is at least 95% identical to the amino acid sequence of SEQ ID NO: 18 and a VL comprising an amino acid sequence that is at least 95% identical to the amino acid sequence of SEQ ID NO: 22.

3. The method of claim 1, wherein in the constant domain CL of each of the second antigen binding domain and the third antigen binding domain the amino acid at position 124 is substituted by lysine (K) (numbering according to Kabat) and the amino acid at position 123 is substituted by lysine (K) or arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index).

4. The method of claim 1, wherein the Fc domain is an IgG Fc domain.

5. The method of claim 1, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

6. The method of claim 1, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

7. The method of claim 1, wherein the autoimmune disease is lupus.

8. The method of claim 7, wherein the lupus is systemic lupus erythematosus (SLE) or lupus nephritis (LN).

9. A method of treating an autoimmune disease in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the VH comprises the amino acid sequence of SEQ ID NO: 7 and the VL comprises the amino acid sequence of SEQ ID NO: 11;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising the amino acid sequence of SEQ ID NO: 18 and a VL comprising the amino acid sequence of SEQ ID NO: 22; and
(c) an Fc domain composed of a first subunit and a second subunit;
wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

10. The method of claim 9, wherein
in the constant domain CL of each of the second antigen binding domain and the third antigen binding domain the amino acid at position 124 is substituted by lysine (K) (numbering according to Kabat) and the amino acid at position 123 is substituted by lysine (K) or arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index).

11. The method of claim 9, wherein the Fc domain is an IgG Fc domain.

12. The method of claim 9, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

13. The method of claim 9, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

14. The method of claim 9, wherein the autoimmune disease is lupus.

15. The method of claim 14, wherein the lupus is SLE or LN.

16. A method of treating an autoimmune disease in an individual, comprising administering to said individual an effective amount of an antibody that binds to CD3 and CD19, wherein the antibody comprises a polypeptide comprising the amino acid sequence of SEQ ID NO: 39, a polypeptide comprising the amino acid sequence of SEQ ID NO: 24, two polypeptides each comprising the amino acid sequence of SEQ ID NO: 25, and a polypeptide comprising the amino acid sequence of SEQ ID NO: 27.

17. The method of claim 16, wherein the autoimmune disease is lupus.

18. The method of claim 17, wherein the lupus is SLE or LN.

19. A method of treating an autoimmune disease in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21; and
(c) an Fc domain composed of a first subunit and a second subunit;
wherein in the constant domain CL of each of the second antigen binding domain and the third antigen binding domain the amino acid at position 124 is substituted by lysine (K) (numbering according to Kabat) and the amino acid at position 123 is substituted by arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index);
and wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

20. The method of claim 19, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

21. The method of claim 20, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

22. A method of treating lupus in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21; and
(c) an Fc domain composed of a first subunit and a second subunit;
wherein in the constant domain CL of each of the second antigen binding domain and the third antigen binding domain the amino acid at position 124 is substituted by lysine (K) (numbering according to Kabat) and the amino acid at position 123 is substituted by arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index);
and wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

23. The method of claim 22, wherein the Fc domain is a human IgG₁ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

24. The method of claim 22, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

25. A method of treating SLE in an individual, comprising administering to said individual an effective amount of an antibody that binds to CD3 and CD19, wherein the antibody comprises:
  (a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10;
  (b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21; and
  (c) an Fc domain composed of a first subunit and a second subunit;
  wherein in the constant domain CL of each of the second antigen binding domain and the third antigen binding domain the amino acid at position 124 is substituted by lysine (K) (numbering according to Kabat) and the amino acid at position 123 is substituted by arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index);
  and wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

26. The method of claim 25, wherein the Fc domain is a human IgG₁ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

27. The method of claim 25, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

28. A method of treating LN in an individual, comprising administering to said individual an effective amount of an antibody that binds to CD3 and CD19, wherein the antibody comprises:
  (a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10;

(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21; and (c) an Fc domain composed of a first subunit and a second subunit;

wherein in the constant domain CL of each of the second antigen binding domain and the third antigen binding domain the amino acid at position 124 is substituted by lysine (K) (numbering according to Kabat) and the amino acid at position 123 is substituted by arginine (R) (numbering according to Kabat), and wherein in the constant domain CH1 of each of the second antigen binding domain and the third antigen binding domain the amino acid at position 147 is substituted by glutamic acid (E) (numbering according to Kabat EU index) and the amino acid at position 213 is substituted by glutamic acid (E) (numbering according to Kabat EU index);

and wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

29. The method of claim 28, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

30. The method of claim 28, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

31. A method of treating an autoimmune disease in an individual, comprising administering to said individual an effective amount of an antibody that binds to CD3 and CD19, wherein the antibody comprises:

(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain (i) comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, and/or (ii) comprises a VH comprising the amino acid sequence of SEQ ID NO: 7 and a VL comprising the amino acid sequence of SEQ ID NO: 11;

(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain (i) comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21, and/or (ii) comprises a VH comprising the amino acid sequence of SEQ ID NO: 18 and a VL comprising the amino acid sequence of SEQ ID NO: 22; and (c) an Fc domain composed of a first subunit and a second subunit, wherein the Fc domain is an IgG Fc domain;

wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

32. The method of claim 31, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

33. The method of claim 31, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

34. A method of treating lupus in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain (i) comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, and/or (ii) comprises a VH comprising the amino acid sequence of SEQ ID NO: 7 and a VL comprising the amino acid sequence of SEQ ID NO: 11;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain (i) comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21, and/or (ii) comprises a VH comprising the amino acid sequence of SEQ ID NO: 18 and a VL comprising the amino acid sequence of SEQ ID NO: 22; and
(c) an Fc domain composed of a first subunit and a second subunit, wherein the Fc domain is an IgG Fc domain; wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

35. The method of claim 34, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

36. The method of claim 34, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

37. A method of treating SLE in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain (i) comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, and/or (ii) comprises a VH comprising the amino acid sequence of SEQ ID NO: 7 and a VL comprising the amino acid sequence of SEQ ID NO: 11;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain (i) comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21, and/or (ii) comprises a VH comprising the amino acid sequence of SEQ ID NO: 18 and a VL comprising the amino acid sequence of SEQ ID NO: 22; and
(c) an Fc domain composed of a first subunit and a second subunit, wherein the Fc domain is an IgG Fc domain; wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

38. The method of claim 37, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

39. The method of claim 37, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

40. A method of treating LN in an individual, comprising administering to said individual an effective amount of an antibody that binds to CD3 and CD19, wherein the antibody comprises:
(a) a first antigen binding domain that binds to CD3, wherein the first antigen binding domain is a Fab molecule wherein the variable domains VL and VH of the Fab light chain and the Fab heavy chain are replaced by each other, and wherein the first antigen binding domain (i) comprises a VH comprising an HCDR 1 comprising the amino acid sequence of SEQ ID NO: 2, an HCDR 2 comprising the amino acid sequence of SEQ ID NO: 3, and an HCDR 3 comprising the amino acid sequence of SEQ ID NO: 5, and a VL comprising an LCDR 1 comprising the amino acid sequence of SEQ ID NO: 8, an LCDR 2 comprising the amino acid sequence of SEQ ID NO: 9, and an LCDR 3 comprising the amino acid sequence of SEQ ID NO: 10, and/or (ii) comprises a VH comprising the amino acid sequence of SEQ ID NO: 7 and a VL comprising the amino acid sequence of SEQ ID NO: 11;
(b) a second antigen binding domain and a third antigen binding domain that bind to CD19, wherein the second antigen binding domain and the third antigen binding domain are each a conventional Fab molecule, and wherein each of the second antigen binding domain and the third antigen binding domain (i) comprises a VH comprising an HCDR 1 comprising the amino acid sequence of SEQ ID NO: 15, an HCDR 2 comprising the amino acid sequence of SEQ ID NO: 16, and an HCDR 3 comprising the amino acid sequence of SEQ ID NO: 17, and a VL comprising an LCDR 1 comprising the amino acid sequence of SEQ ID NO: 19, an LCDR 2 comprising the amino acid sequence of SEQ ID NO: 20, and an LCDR 3 comprising the amino acid sequence of SEQ ID NO: 21, and/or (ii) comprises a VH comprising the amino acid sequence of SEQ ID NO: 18 and a VL comprising the amino acid sequence of SEQ ID NO: 22; and
(c) an Fc domain composed of a first subunit and a second subunit, wherein the Fc domain is an IgG Fc domain; wherein the second antigen binding domain is fused at the C-terminus of the Fab heavy chain to the N-terminus of the Fab heavy chain of the first antigen binding domain, and the first antigen binding domain and the third antigen binding domain are each fused at the C-terminus of the Fab heavy chain to the N-terminus of one of the subunits of the Fc domain.

41. The method of claim 40, wherein the Fc domain is a human IgG$_1$ Fc domain, and wherein in the first subunit of the Fc domain the threonine residue at position 366 is replaced with a tryptophan residue (T366W) and the serine residue at position 354 is replaced with a cysteine residue (S354C), and in the second subunit of the Fc domain the tyrosine residue at position 407 is replaced with a valine residue (Y407V), the threonine residue at position 366 is replaced with a serine residue (T366S), the leucine residue at position 368 is replaced with an alanine residue (L368A), and the tyrosine residue at position 349 is replaced with a cysteine residue (Y349C) (numbering according to Kabat EU index), and wherein further in each of the first subunit and the second subunit of the Fc domain the leucine residue at position 234 is replaced with an alanine residue (L234A), the leucine residue at position 235 is replaced with an alanine residue (L235A), and the proline residue at position 329 is replaced by a glycine residue (P329G) (numbering according to Kabat EU index).

42. The method of claim 40, wherein the antibody comprises a polypeptide comprising an amino acid sequence that is at least 95% identical to the amino acid sequence of SEQ ID NO: 39, a polypeptide comprising an amino acid sequence that is at least 95% identical to the amino acid sequence of SEQ ID NO: 24, two polypeptides each comprising an amino acid sequence that is at least 95% identical to the amino acid sequence of SEQ ID NO: 25, and a polypeptide comprising an amino acid sequence that is at least 95% identical to the amino acid sequence of SEQ ID NO: 27.

43. The method of claim 1, wherein the second antigen binding domain is fused at the C-terminus of the Fab heavy chain to the N-terminus of the Fab heavy chain of the first antigen binding domain via a peptide linker.

44. The method of claim 43, wherein the peptide linker comprises the amino acid sequence GGGGSGGGGS (SEQ ID NO: 48).

45. The method of claim 9, wherein the second antigen binding domain is fused at the C-terminus of the Fab heavy chain to the N-terminus of the Fab heavy chain of the first antigen binding domain via a peptide linker.

46. The method of claim 45, wherein the peptide linker comprises the amino acid sequence GGGGSGGGGS (SEQ ID NO: 48).

47. The method of claim 16, wherein the second antigen binding domain is fused at the C-terminus of the Fab heavy chain to the N-terminus of the Fab heavy chain of the first antigen binding domain via a peptide linker.

48. The method of claim 47, wherein the peptide linker comprises the amino acid sequence GGGGSGGGGS (SEQ ID NO: 48).

49. The method of claim 19, wherein the second antigen binding domain is fused at the C-terminus of the Fab heavy chain to the N-terminus of the Fab heavy chain of the first antigen binding domain via a peptide linker.

50. The method of claim 49, wherein the peptide linker comprises the amino acid sequence GGGGSGGGGS (SEQ ID NO: 48).

51. The method of claim 22, wherein the second antigen binding domain is fused at the C-terminus of the Fab heavy chain to the N-terminus of the Fab heavy chain of the first antigen binding domain via a peptide linker.

52. The method of claim 51, wherein the peptide linker comprises the amino acid sequence GGGGSGGGGS (SEQ ID NO: 48).

53. The method of claim 25, wherein the second antigen binding domain is fused at the C-terminus of the Fab heavy chain to the N-terminus of the Fab heavy chain of the first antigen binding domain via a peptide linker.

54. The method of claim 53, wherein the peptide linker comprises the amino acid sequence GGGGSGGGGS (SEQ ID NO: 48).

55. The method of claim 28, wherein the second antigen binding domain is fused at the C-terminus of the Fab heavy chain to the N-terminus of the Fab heavy chain of the first antigen binding domain via a peptide linker.

56. The method of claim 55, wherein the peptide linker comprises the amino acid sequence GGGGSGGGGS (SEQ ID NO: 48).

57. The method of claim 31, wherein the second antigen binding domain is fused at the C-terminus of the Fab heavy chain to the N-terminus of the Fab heavy chain of the first antigen binding domain via a peptide linker.

58. The method of claim 57, wherein the peptide linker comprises the amino acid sequence GGGGSGGGGS (SEQ ID NO: 48).

59. The method of claim 34, wherein the second antigen binding domain is fused at the C-terminus of the Fab heavy chain to the N-terminus of the Fab heavy chain of the first antigen binding domain via a peptide linker.

60. The method of claim 59, wherein the peptide linker comprises the amino acid sequence GGGGSGGGGS (SEQ ID NO: 48).

61. The method of claim 37, wherein the second antigen binding domain is fused at the C-terminus of the Fab heavy chain to the N-terminus of the Fab heavy chain of the first antigen binding domain via a peptide linker.

62. The method of claim 61, wherein the peptide linker comprises the amino acid sequence GGGGSGGGGS (SEQ ID NO: 48).

63. The method of claim 40, wherein the second antigen binding domain is fused at the C-terminus of the Fab heavy chain to the N-terminus of the Fab heavy chain of the first antigen binding domain via a peptide linker.

64. The method of claim 63, wherein the peptide linker comprises the amino acid sequence GGGGSGGGGS (SEQ ID NO: 48).

* * * * *

```
                              SEQUENCE LISTING

Sequence total quantity: 54
SEQ ID NO: 1            moltype = AA  length = 5
FEATURE                 Location/Qualifiers
source                  1..5
                        mol_type = protein
                        organism = synthetic construct
SEQUENCE: 1
TYAMN                                                                      5

SEQ ID NO: 2            moltype = AA  length = 5
FEATURE                 Location/Qualifiers
source                  1..5
                        mol_type = protein
                        organism = synthetic construct
SEQUENCE: 2
SYAMN                                                                      5

SEQ ID NO: 3            moltype = AA  length = 19
FEATURE                 Location/Qualifiers
source                  1..19
                        mol_type = protein
                        organism = synthetic construct
SEQUENCE: 3
RIRSKYNNYA TYYADSVKG                                                      19

SEQ ID NO: 4            moltype = AA  length = 14
FEATURE                 Location/Qualifiers
source                  1..14
                        mol_type = protein
                        organism = synthetic construct
SEQUENCE: 4
HGNFGNSYVS WFAY                                                           14

SEQ ID NO: 5            moltype = AA  length = 14
FEATURE                 Location/Qualifiers
source                  1..14
                        mol_type = protein
                        organism = synthetic construct
SEQUENCE: 5
HTTFPSSYVS YYGY                                                           14

SEQ ID NO: 6            moltype = AA  length = 125
FEATURE                 Location/Qualifiers
source                  1..125
                        mol_type = protein
                        organism = synthetic construct
SEQUENCE: 6
EVQLLESGGG LVQPGGSLRL SCAASGFTFS TYAMNWVRQA PGKGLEWVSR IRSKYNNYAT          60
YYADSVKGRF TISRDDSKNT LYLQMNSLRA EDTAVYYCVR HGNFGNSYVS WFAYWGQGTL         120
VTVSS                                                                    125

SEQ ID NO: 7            moltype = AA  length = 125
FEATURE                 Location/Qualifiers
source                  1..125
                        mol_type = protein
                        organism = synthetic construct
SEQUENCE: 7
EVQLLESGGG LVQPGGSLRL SCAASGFQFS SYAMNWVRQA PGKGLEWVSR IRSKYNNYAT          60
```

```
YYADSVKGRF TISRDDSKNT LYLQMNSLRA EDTAVYYCVR HTTFPSSYVS YYGYWGQGTL    120
VTVSS                                                               125

SEQ ID NO: 8           moltype = AA  length = 14
FEATURE                Location/Qualifiers
source                 1..14
                       mol_type = protein
                       organism = synthetic construct
SEQUENCE: 8
GSSTGAVTTS NYAN                                                     14

SEQ ID NO: 9           moltype = AA  length = 7
FEATURE                Location/Qualifiers
source                 1..7
                       mol_type = protein
                       organism = synthetic construct
SEQUENCE: 9
GTNKRAP                                                             7

SEQ ID NO: 10          moltype = AA  length = 9
FEATURE                Location/Qualifiers
source                 1..9
                       mol_type = protein
                       organism = synthetic construct
SEQUENCE: 10
ALWYSNLWV                                                           9

SEQ ID NO: 11          moltype = AA  length = 109
FEATURE                Location/Qualifiers
source                 1..109
                       mol_type = protein
                       organism = synthetic construct
SEQUENCE: 11
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVL                109

SEQ ID NO: 12          moltype = AA  length = 453
FEATURE                Location/Qualifiers
source                 1..453
                       mol_type = protein
                       organism = synthetic construct
SEQUENCE: 12
EVQLLESGGG LVQPGGSLRL SCAASGFTFS TYAMNWVRQA PGKGLEWVSR IRSKYNNYAT    60
YYADSVKGRF TISRDDSKNT LYLQMNSLRA EDTAVYYCVR HGNFGNSYVS WFAYWGQGTL    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
ELLGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALPAPI EKTISKAKGQ PREPQVYTLP    360
PSRDELTKNQ VSLTCLVKGF YPSDIAVEWE SNGQPENNYK TTPPVLDSDG SFFLYSKLTV    420
DKSRWQQGNV FSCSVMHEAL HNHYTQKSLS LSP                                453

SEQ ID NO: 13          moltype = AA  length = 453
FEATURE                Location/Qualifiers
source                 1..453
                       mol_type = protein
                       organism = synthetic construct
SEQUENCE: 13
EVQLLESGGG LVQPGGSLRL SCAASGFQFS SYAMNWVRQA PGKGLEWVSR IRSKYNNYAT    60
YYADSVKGRF TISRDDSKNT LYLQMNSLRA EDTAVYYCVR HTTFPSSYVS YYGYWGQGTL    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
EAAGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALPAPI EKTISKAKGQ PREPQVYTLP    360
PSRDELTKNQ VSLTCLVKGF YPSDIAVEWE SNGQPENNYK TTPPVLDSDG SFFLYSKLTV    420
DKSRWQQGNV FSCSVMHEAL HNHYTQKSLS LSP                                453

SEQ ID NO: 14          moltype = AA  length = 216
FEATURE                Location/Qualifiers
source                 1..216
                       mol_type = protein
                       organism = synthetic construct
SEQUENCE: 14
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVLR TVAAPSVFIF    120
PPSDEQLKSG TASVVCLLNN FYPREAKVQW KVDNALQSGN SQESVTEQDS KDSTYSLSST    180
LTLSKADYEK HKVYACEVTH QGLSSPVTKS FNRGEC                             216

SEQ ID NO: 15          moltype = AA  length = 5
FEATURE                Location/Qualifiers
```

```
source                          1..5
                                mol_type = protein
                                organism = synthetic construct
SEQUENCE: 15
DYIMH                                                                     5

SEQ ID NO: 16                   moltype = AA   length = 17
FEATURE                         Location/Qualifiers
source                          1..17
                                mol_type = protein
                                organism = synthetic construct
SEQUENCE: 16
YINPYNDGSK YTEKFQG                                                       17

SEQ ID NO: 17                   moltype = AA   length = 12
FEATURE                         Location/Qualifiers
source                          1..12
                                mol_type = protein
                                organism = synthetic construct
SEQUENCE: 17
GTYYYGPQLF DY                                                            12

SEQ ID NO: 18                   moltype = AA   length = 121
FEATURE                         Location/Qualifiers
source                          1..121
                                mol_type = protein
                                organism = synthetic construct
SEQUENCE: 18
QVQLVQSGAE VKKPGASVKV SCKASGYTFT DYIMHWVRQA PGQGLEWMGY INPYNDGSKY         60
TEKFQGRVTM TSDTSISTAY MELSRLRSDD TAVYYCARGT YYYGPQLFDY WGQGTTVTVS        120
S                                                                       121

SEQ ID NO: 19                   moltype = AA   length = 16
FEATURE                         Location/Qualifiers
source                          1..16
                                mol_type = protein
                                organism = synthetic construct
SEQUENCE: 19
KSSQSLETST GTTYLN                                                        16

SEQ ID NO: 20                   moltype = AA   length = 7
FEATURE                         Location/Qualifiers
source                          1..7
                                mol_type = protein
                                organism = synthetic construct
SEQUENCE: 20
RVSKRFS                                                                   7

SEQ ID NO: 21                   moltype = AA   length = 9
FEATURE                         Location/Qualifiers
source                          1..9
                                mol_type = protein
                                organism = synthetic construct
SEQUENCE: 21
LQLLEDPYT                                                                 9

SEQ ID NO: 22                   moltype = AA   length = 112
FEATURE                         Location/Qualifiers
source                          1..112
                                mol_type = protein
                                organism = synthetic construct
SEQUENCE: 22
DIVMTQTPLS LSVTPGQPAS ISCKSSQSLE TSTGTTYLNW YLQKPGQSPQ LLIYRVSKRF         60
SGVPDRFSGS GSGTDFTLKI SRVEAEDVGV YYCLQLLEDP YTFGQGTKLE IK                112

SEQ ID NO: 23                   moltype = AA   length = 674
FEATURE                         Location/Qualifiers
source                          1..674
                                mol_type = protein
                                organism = synthetic construct
SEQUENCE: 23
QVQLVQSGAE VKKPGASVKV SCKASGYTFT DYIMHWVRQA PGQGLEWMGY INPYNDGSKY         60
TEKFQGRVTM TSDTSISTAY MELSRLRSDD TAVYYCARGT YYYGPQLFDY WGQGTTVTVS        120
SASTKGPSVF PLAPSSKSTS GGTAALGCLV KDYFPEPVTV SWNSGALTSG VHTFPAVLQS        180
SGLYSLSSVV TVPSSSLGTQ TYICNVNHKP SNTKVDEKVE PKSCDGGGGS GGGGGQAVVT        240
QEPSLTVSPG GTVTLTCGSS TGAVTTSNYA NWVQEKPGQA FRGLIGGTNK RAPGTPARFS        300
GSLLGGKAAL TLSGAQPEDE AEYYCALWYS NLWVFGGGTK LTVLSSASTK GPSVFPLAPS        360
SKSTSGGTAA LGCLVKDYFP EPVTVSWNSG ALTSGVHTFP AVLQSSGLYS LSSVVTVPSS        420
SLGTQTYIC N VNHKPSNTKV DKKVEPKSCD KTHTCPPCPA PEAGGPSVF LFPPKPKDTL        480
```

```
MISRTPEVTC VVVDVSHEDP EVKFNWYVDG VEVHNAKTKP REEQYNSTYR VVSVLTVLHQ    540
DWLNGKEYKC KVSNKALGAP IEKTISKAKG QPREPQVYTL PPCRDELTKN QVSLWCLVKG    600
FYPSDIAVEW ESNGQPENNY KTTPPVLDSD GSFFLYSKLT VDKSRWQQGN VFSCSVMHEA    660
LHNHYTQKSL SLSP                                                     674

SEQ ID NO: 24         moltype = AA  length = 449
FEATURE               Location/Qualifiers
source                1..449
                      mol_type = protein
                      organism = synthetic construct
SEQUENCE: 24
QVQLVQSGAE VKKPGASVKV SCKASGYTFT DYIMHWVRQA PGQGLEWMGY INPYNDGSKY    60
TEKFQGRVTM TSDTSISTAY MELSRLRSDD TAVYYCARGT YYYGPQLFDY WGQGTTVTVS    120
SASTKGPSVF PLAPSSKSTS GGTAALGCLV EDYFPEPVTV SWNSGALTSG VHTFPAVLQS    180
SGLYSLSSVV TVPSSSLGTQ TYICNVNHKP SNTKVDEKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALGAPIEKTI SKAKGQPREP QVCTLPPSRD    360
ELTKNQVSLS CAVKGFYPSD IAVEWESNGQ PENNYKTTPP VLDSDGSFFL VSKLTVDKSR    420
WQQGNVFSCS VMHEALHNHY TQKSLSLSP                                     449

SEQ ID NO: 25         moltype = AA  length = 219
FEATURE               Location/Qualifiers
source                1..219
                      mol_type = protein
                      organism = synthetic construct
SEQUENCE: 25
DIVMTQTPLS LSVTPGQPAS ISCKSSQSLE TSTGTTYLNW YLQKPGQSPQ LLIYRVSKRF    60
SGVPDRFSGS GSGTDFTLKI SRVEAEDVGV YYCLQLLEDP YTFGQGTKLE IKRTVAAPSV    120
FIFPPSDRKL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                          219

SEQ ID NO: 26         moltype = AA  length = 232
FEATURE               Location/Qualifiers
source                1..232
                      mol_type = protein
                      organism = synthetic construct
SEQUENCE: 26
EVQLLESGGG LVQPGGSLRL SCAASGFTFS TYAMNWVRQA PGKGLEWVSR IRSKYNNYAT    60
YYADSVKGRF TISRDDSKNT LYLQMNSLRA EDTAVYYCVR HGNFGNSYVS WFAYWGQGTL    120
VTVSSASVAA PSVFIFPPSD EQLKSGTASV VCLLNNFYPR EAKVQWKVDN ALQSGNSQES    180
VTEQDSKDST YSLSSTLTLS KADYEKHKVY ACEVTHQGLS SPVTKSFNRG EC            232

SEQ ID NO: 27         moltype = AA  length = 232
FEATURE               Location/Qualifiers
source                1..232
                      mol_type = protein
                      organism = synthetic construct
SEQUENCE: 27
EVQLLESGGG LVQPGGSLRL SCAASGFQFS SYAMNWVRQA PGKGLEWVSR IRSKYNNYAT    60
YYADSVKGRF TISRDDSKNT LYLQMNSLRA EDTAVYYCVR HTTFPSSYVS YYGYWGQGTL    120
VTVSSASVAA PSVFIFPPSD EQLKSGTASV VCLLNNFYPR EAKVQWKVDN ALQSGNSQES    180
VTEQDSKDST YSLSSTLTLS KADYEKHKVY ACEVTHQGLS SPVTKSFNRG EC            232

SEQ ID NO: 28         moltype = AA  length = 5
FEATURE               Location/Qualifiers
source                1..5
                      mol_type = protein
                      organism = synthetic construct
SEQUENCE: 28
DYIMH                                                               5

SEQ ID NO: 29         moltype = AA  length = 17
FEATURE               Location/Qualifiers
source                1..17
                      mol_type = protein
                      organism = synthetic construct
SEQUENCE: 29
YINPYNDGSK YTEKFQG                                                  17

SEQ ID NO: 30         moltype = AA  length = 12
FEATURE               Location/Qualifiers
source                1..12
                      mol_type = protein
                      organism = synthetic construct
SEQUENCE: 30
GTYYYGSALF DY                                                       12

SEQ ID NO: 31         moltype = AA  length = 121
FEATURE               Location/Qualifiers
```

```
                         source          1..121
                                         mol_type = protein
                                         organism = synthetic construct
SEQUENCE: 31
QVQLVQSGAE VKKPGASVKV SCKASGYTFT DYIMHWVRQA PGQGLEWMGY INPYNDGSKY      60
TEKFQGRVTM TSDTSISTAY MELSRLRSDD TAVYYCARGT YYYGSALFDY WGQGTTVTVS     120
S                                                                    121

SEQ ID NO: 32           moltype = AA  length = 16
FEATURE                 Location/Qualifiers
source                  1..16
                        mol_type = protein
                        organism = synthetic construct
SEQUENCE: 32
KSSQSLENPN GNTYLN                                                     16

SEQ ID NO: 33           moltype = AA  length = 7
FEATURE                 Location/Qualifiers
source                  1..7
                        mol_type = protein
                        organism = synthetic construct
SEQUENCE: 33
RVSKRFS                                                                7

SEQ ID NO: 34           moltype = AA  length = 9
FEATURE                 Location/Qualifiers
source                  1..9
                        mol_type = protein
                        organism = synthetic construct
SEQUENCE: 34
LQLTHVPYT                                                              9

SEQ ID NO: 35           moltype = AA  length = 112
FEATURE                 Location/Qualifiers
source                  1..112
                        mol_type = protein
                        organism = synthetic construct
SEQUENCE: 35
DIVMTQTPLS LSVTPGQPAS ISCKSSQSLE NPNGNTYLNW YLQKPGQSPQ LLIYRVSKRF     60
SGVPDRFSGS GSGTDFTLKI SRVEAEDVGV YYCLQLTHVP YTFGQGTKLE IK             112

SEQ ID NO: 36           moltype = AA  length = 674
FEATURE                 Location/Qualifiers
source                  1..674
                        mol_type = protein
                        organism = synthetic construct
SEQUENCE: 36
QVQLVQSGAE VKKPGASVKV SCKASGYTFT DYIMHWVRQA PGQGLEWMGY INPYNDGSKY      60
TEKFQGRVTM TSDTSISTAY MELSRLRSDD TAVYYCARGT YYYGSALFDY WGQGTTVTVS     120
SASTKGPSVF PLAPSSKSTS GGTAALGCLV EDYFPEPVTV SWNSGALTSG VHTFPAVLQS     180
SGLYSLSSVV TVPSSSLGTQ TYICNVNHKP SNTKVDEKVE PKSCDGGGGS GGGGGQAVVT     240
QEPSLTVSPG GTVTLTCGSS TGAVTTSNYA NWVQEKPGQA FRGLIGGTNK RAPGTPARFS     300
GSLLGGKAAL TLSGAQPEDE AEYYCALWYS NLWVFGGGTK LTVLSSASTK GPSVFPLAPS     360
SKSTSGGTAA LGCLVKDYFP EPVTVSWNSG ALTSGVHTFP AVLQSSGLYS LSSVVTVPSS     420
SLGTQTYICN VNHKPSNTKV DKKVEPKSCD KTHTCPPCPA PEAAGGPSVF LFPPKPKDTL     480
MISRTPEVTC VVVDVSHEDP EVKFNWYVDG VEVHNAKTKP REEQYNSTYR VVSVLTVLHQ     540
DWLNGKEYKC KVSNKALGAP IEKTISKAKG QPREPQVYTL PPCRDELTKN QVSLWCLVKG     600
FYPSDIAVEW ESNGQPENNY KTTPPVLDSD GSFFLYSKLT VDKSRWQQGN VFSCSVMHEA     660
LHNHYTQKSL SLSP                                                      674

SEQ ID NO: 37           moltype = AA  length = 449
FEATURE                 Location/Qualifiers
source                  1..449
                        mol_type = protein
                        organism = synthetic construct
SEQUENCE: 37
QVQLVQSGAE VKKPGASVKV SCKASGYTFT DYIMHWVRQA PGQGLEWMGY INPYNDGSKY      60
TEKFQGRVTM TSDTSISTAY MELSRLRSDD TAVYYCARGT YYYGSALFDY WGQGTTVTVS     120
SASTKGPSVF PLAPSSKSTS GGTAALGCLV EDYFPEPVTV SWNSGALTSG VHTFPAVLQS     180
SGLYSLSSVV TVPSSSLGTQ TYICNVNHKP SNTKVDEKVE PKSCDKTHTC PPCPAPEAAG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALGAPIEKTI SKAKGQPREP QVCTLPPSRD     360
ELTKNQVSLS CAVKGFYPSD IAVEWESNGQ PENNYKTTPP VLDSDGSFFL VSKLTVDKSR     420
WQQGNVFSCS VMHEALHNHY TQKSLSLSP                                       449

SEQ ID NO: 38           moltype = AA  length = 219
FEATURE                 Location/Qualifiers
source                  1..219
                        mol_type = protein
```

```
                        organism = synthetic construct
SEQUENCE: 38
DIVMTQTPLS LSVTPGQPAS ISCKSSQSLE NPNGNTYLNW YLQKPGQSPQ LLIYRVSKRF    60
SGVPDRFSGS GSGTDFTLKI SRVEAEDVGV YYCLQLTHVP YTFGQGTKLE IKRTVAAPSV   120
FIFPPSDRKL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 39           moltype = AA  length = 674
FEATURE                 Location/Qualifiers
source                  1..674
                        mol_type = protein
                        organism = synthetic construct
SEQUENCE: 39
QVQLVQSGAE VKKPGASVKV SCKASGYTFT DYIMHWVRQA PGQGLEWMGY INPYNDGSKY    60
TEKFQGRVTM TSDTSISTAY MELSRLRSDD TAVYYCARGT YYYGPQLFDY WGQGTTVTVS   120
SASTKGPSVF PLAPSSKSTS GGTAALGCLV EDYFPEPVTV SWNSGALTSG VHTFPAVLQS   180
SGLYSLSSVV TVPSSSLGTQ TYICNVNHKP SNTKVDEKVE PKSCDGGGGS GGGGSQAVVT   240
QEPSLTVSPG GTVTLTCGSS TGAVTTSNYA NWVQEKPGQA FRGLIGGTNK RAPGTPARFS   300
GSLLGGKAAL TLSGAQPEDE AEYYCALWYS NLWVFGGGTK LTVLSSASTK GPSVFPLAPS   360
SKSTSGGTAA LGCLVKDYFP EPVTVSWNSG ALTSGVHTFP AVLQSSGLYS LSSVVTVPSS   420
SLGTQTYICN VNHKPSNTKV DKKVEPKSCD KTHTCPPCPA PEAAGGPSVF LFPPKPKDTL   480
MISRTPEVTC VVVDVSHEDP EVKFNWYVDG VEVHNAKTKP REEQYNSTYR VVSVLTVLHQ   540
DWLNGKEYKC KVSNKALGAP IEKTISKAKG QPREPQVYTL PPCRDELTKN QVSLWCLVKG   600
FYPSDIAVEW ESNGQPENNY KTTPPVLDSD GSFFLYSKLT VDKSRWQQGN VFSCSVMHEA   660
LHNHYTQKSL SLSP                                                    674

SEQ ID NO: 40           moltype = AA  length = 674
FEATURE                 Location/Qualifiers
source                  1..674
                        mol_type = protein
                        organism = synthetic construct
SEQUENCE: 40
QVQLVQSGAE VKKPGASVKV SCKASGYTFT DYIMHWVRQA PGQGLEWMGY INPYNDGSKY    60
TEKFQGRVTM TSDTSISTAY MELSRLRSDD TAVYYCARGT YYYGSALFDY WGQGTTVTVS   120
SASTKGPSVF PLAPSSKSTS GGTAALGCLV EDYFPEPVTV SWNSGALTSG VHTFPAVLQS   180
SGLYSLSSVV TVPSSSLGTQ TYICNVNHKP SNTKVDEKVE PKSCDGGGGS GGGGSQAVVT   240
QEPSLTVSPG GTVTLTCGSS TGAVTTSNYA NWVQEKPGQA FRGLIGGTNK RAPGTPARFS   300
GSLLGGKAAL TLSGAQPEDE AEYYCALWYS NLWVFGGGTK LTVLSSASTK GPSVFPLAPS   360
SKSTSGGTAA LGCLVKDYFP EPVTVSWNSG ALTSGVHTFP AVLQSSGLYS LSSVVTVPSS   420
SLGTQTYICN VNHKPSNTKV DKKVEPKSCD KTHTCPPCPA PEAAGGPSVF LFPPKPKDTL   480
MISRTPEVTC VVVDVSHEDP EVKFNWYVDG VEVHNAKTKP REEQYNSTYR VVSVLTVLHQ   540
DWLNGKEYKC KVSNKALGAP IEKTISKAKG QPREPQVYTL PPCRDELTKN QVSLWCLVKG   600
FYPSDIAVEW ESNGQPENNY KTTPPVLDSD GSFFLYSKLT VDKSRWQQGN VFSCSVMHEA   660
LHNHYTQKSL SLSP                                                    674

SEQ ID NO: 41           moltype = AA  length = 360
FEATURE                 Location/Qualifiers
source                  1..360
                        mol_type = protein
                        organism = synthetic construct
SEQUENCE: 41
QDGNEEMGGI TQTPYKVSIS GTTVILTCPQ YPGSEILWQH NDKNIGGDED DKNIGSDEDH    60
LSLKEFSELE QSGYYVCYPR GSKPEDANFY LYLRARVSEN CVDEQLYFQG GSPKSADKTH   120
TCPPCPAPEL LGGPSVFLFP PKPKDTLMIS RTPEVTCVVV DVSHEDPEVK FNWYVDGVEV   180
HNAKTKPREE QYNSTYRVVS VLTVLHQDWL NGKEYKCKVS NKALPAPIEK TISKAKGQPR   240
EPQVYTLPPC RDELTKNQVS LWCLVKGFYP SDIAVEWESN GQPENNYKTT PPVLDSDGSF   300
FLYSKLTVDK SRWQQGNVFS CSVMHEALHN HYTQKSLSLS PGKSGGLNDI FEAQKIEWHE   360

SEQ ID NO: 42           moltype = AA  length = 325
FEATURE                 Location/Qualifiers
source                  1..325
                        mol_type = protein
                        organism = synthetic construct
SEQUENCE: 42
FKIPIEELED RVFVNCNTSI TWVEGTVGTL LSDITRLDLG KRILDPRGIY RCNGTDIYKD    60
KESTVQHYR MCRSEQLYFQ GDKTHTCPPC PAPELLGGPS VFLFPPKPKD TLMISRTPEV   120
TCVVVDVSHE DPEVKFNWYV DGVEVHNAKT KPREEQYNST YRVVSVLTVL HQDWLNGKEY   180
KCKVSNKALP APIEKTISKA KGQPREPQVC TLPPSRDELT KNQVSLSCAV KGFYPSDIAV   240
EWESNGQPEN NYKTTPPVLD SDGSFFLVSK LTVDKSRWQQ GNVFSCSVMH EALHNHYTQK   300
SLSLSPGKSG GLNDIFEAQK IEWHE                                        325

SEQ ID NO: 43           moltype = AA  length = 534
FEATURE                 Location/Qualifiers
source                  1..534
                        mol_type = protein
                        organism = synthetic construct
SEQUENCE: 43
PEEPLVVKVE EGDNAVLQCL KGTSDGPTQQ LTWSRESPLK PFLKLSLGLP GLGIHMRPLA    60
IWLFIFNVSQ QMGGFYLCQP GPPSEKAWQP GWTVNVEGSG ELFRWNVSDL GGLGCGLKNR   120
```

```
SSEGPSSPSG KLMSPKLYVW AKDRPEIWEG EPPCLPPRDS LNQSLSQDLT MAPGSTLWLS    180
CGVPPDSVSR GPLSWTHVHP KGPKSLLSLE LKDDRPARDM WVMETGLLLP RATAQDAGKY    240
YCHRGNLTMS FHLEITARPV LWHWLLRTGG WKVDASGGSP TPPTPGGGSA DKTHTCPPCP    300
APELLGGPSV FLFPPKPKDT LMISRTPEVT CVVVDVSHED PEVKFNWYVD GVEVHNAKTK    360
PREEQYNSTY RVVSVLTVLH QDWLNGKEYK CKVSNKALPA PIEKTISKAK GQPREPQVYT    420
LPPCRDELTK NQVSLWCLVK GFYPSDIAVE WESNGQPENN YKTTPPVLDS DGSFFLYSKL    480
TVDKSRWQQG NVFSCSVMHE ALHNHYTQKS LSLSPGKSGG LNDIFEAQKI EWHE          534

SEQ ID NO: 44              moltype = AA   length = 225
FEATURE                    Location/Qualifiers
source                     1..225
                           mol_type = protein
                           organism = synthetic construct
SEQUENCE: 44
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVCT LPPSRDELTK NQVSLSCAVK GFYPSDIAVE WESNGQPENN YKTTPPVLDS    180
DGSFFLVSKL TVDKSRWQQG NVFSCSVMHE ALHNRFTQKS LSLSP                    225

SEQ ID NO: 45              moltype = AA   length = 186
FEATURE                    Location/Qualifiers
source                     1..186
                           mol_type = protein
                           organism = Homo sapiens
SEQUENCE: 45
QDGNEEMGGI TQTPYKVSIS GTTVILTCPQ YPGSEILWQH NDKNIGGDED DKNIGSDEDH     60
LSLKEFSELE QSGYYVCYPR GSKPEDANFY LYLRARVCEN CMEMDVMSVA TIVIVDICIT    120
GGLLLLVYYW SKNRKAKAKP VTRGAGAGGR QRGQNKERPP PVPNPDYEPI RKGQRDLYSG    180
LNQRRI                                                               186

SEQ ID NO: 46              moltype = AA   length = 177
FEATURE                    Location/Qualifiers
source                     1..177
                           mol_type = protein
                           organism = Macaca fascicularis
SEQUENCE: 46
QDGNEEMGSI TQTPYQVSIS GTTVILTCSQ HLGSEAWQH NGKNKEDSGD RLFLPEFSEM      60
EQSGYYVCYP RGSNPEDASH HLYLKARVCE NCMEMDVMAV ATIVIVDICI TLGLLLLVYY    120
WSKNRKAKAK PVTRGAGAGG RQRGQNKERP PPVPNPDYEP IRKGQQDLYS GLNQRRI       177

SEQ ID NO: 47              moltype = AA   length = 225
FEATURE                    Location/Qualifiers
source                     1..225
                           mol_type = protein
                           organism = Homo sapiens
SEQUENCE: 47
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSP                    225

SEQ ID NO: 48              moltype = AA   length = 10
FEATURE                    Location/Qualifiers
source                     1..10
                           mol_type = protein
                           organism = synthetic construct
SEQUENCE: 48
GGGGSGGGGS                                                            10

SEQ ID NO: 49              moltype = AA   length = 11
FEATURE                    Location/Qualifiers
source                     1..11
                           mol_type = protein
                           organism = synthetic construct
SEQUENCE: 49
DGGGGSGGGG S                                                          11

SEQ ID NO: 50              moltype = AA   length = 10
FEATURE                    Location/Qualifiers
source                     1..10
                           mol_type = protein
                           organism = synthetic construct
SEQUENCE: 50
GGGGSGGGGG                                                            10

SEQ ID NO: 51              moltype = AA   length = 11
FEATURE                    Location/Qualifiers
source                     1..11
                           mol_type = protein
```

```
                    organism = synthetic construct
SEQUENCE: 51
DGGGGSGGGG G                                                                11

SEQ ID NO: 52           moltype = AA  length = 107
FEATURE                 Location/Qualifiers
source                  1..107
                        mol_type = protein
                        organism = Homo sapiens
SEQUENCE: 52
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 53           moltype = AA  length = 105
FEATURE                 Location/Qualifiers
source                  1..105
                        mol_type = protein
                        organism = Homo sapiens
SEQUENCE: 53
QPKAAPSVTL FPPSSEELQA NKATLVCLIS DFYPGAVTVA WKADSSPVKA GVETTTPSKQ    60
SNNKYAASSY LSLTPEQWKS HRSYSCQVTH EGSTVEKTVA PTECS                   105

SEQ ID NO: 54           moltype = AA  length = 328
FEATURE                 Location/Qualifiers
source                  1..328
                        mol_type = protein
                        organism = Homo sapiens
SEQUENCE: 54
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                      328
```